US007842298B2

(12) United States Patent
Meng et al.

(10) Patent No.: US 7,842,298 B2
(45) Date of Patent: Nov. 30, 2010

(54) AVIAN HEPATITIS E VIRUS, VACCINES AND METHODS OF PROTECTING AGAINST AVIAN HEPATITIS-SPLENOMEGALY SYNDROME AND MAMMALIAN HEPATITIS E

(75) Inventors: Xiang-Jin Meng, Blacksburg, VA (US); Gholamreza Haqshenas, Tehran (IR); Fang-Fang Huang, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 12/507,576

(22) Filed: Jul. 22, 2009

(65) Prior Publication Data

US 2010/0034845 A1 Feb. 11, 2010

Related U.S. Application Data

(62) Division of application No. 11/184,574, filed on Jul. 19, 2005, now Pat. No. 7,582,303.

(51) Int. Cl.
*A16K 39/12* (2006.01)
*A61K 39/29* (2006.01)
*C12Q 1/70* (2006.01)
*C12Q 1/68* (2006.01)

(52) U.S. Cl. ............... 424/204.1; 424/225.1; 435/235.1; 435/5; 435/6

(58) Field of Classification Search ........................ None
See application file for complete search history.

(56) References Cited

U.S. PATENT DOCUMENTS

| | | | |
|---|---|---|---|
| 5,686,239 A | 11/1997 | Reyes et al. | 435/5 |
| 5,741,490 A | 4/1998 | Reyes et al. | 424/189.1 |
| 5,770,689 A | 6/1998 | Reyes et al. | 530/324 |
| 5,885,768 A | 3/1999 | Reyes et al. | 435/5 |
| 6,022,685 A | 2/2000 | Fields et al. | 435/5 |
| 6,054,567 A | 4/2000 | Emerson et al. | |
| 7,005,130 B2 | 2/2006 | Meng et al. | |

FOREIGN PATENT DOCUMENTS

WO 99/04029 A2 1/1999

OTHER PUBLICATIONS

Fields et al., Eds., Fields Virology, Third Edition, Lippincott Williams & Wilkins, 1996, pp. 480-490.
Payne et al., "Sequence data suggests big liver and spleen disease virus (BLSV) is genetically related to hepatitis E virus," Veterinary Microbiol. 68:119-125, 1999.
Shivaprasad et al., "Necrohemorrhagic Hepatitis in Broiler Breeders," Proceedings, Western Poultry Disease Conference, p. 6, Sacramento, CA, 1995.
Meng et al., "A novel virus in swine is closely related to the human hepatitis E virus," Proc. Natl. Acad. Sci. USA 94:9860-9865, Sep. 1997.
McAlinden et al., "The Identification of an 18,000-Molecular-Weight Antigen Specific to Big Liver and Spleen Disease," Avian Diseases 39:788-795, 1995.
Ellis et al., "An antigen detection immunoassay for big liver and spleen disease agent," Veterinary Microbiol. 46:315-326, 1995.
Crerar et al., "The experimental production of big liver and spleen disease in broiler breeder hens," Australian Veterinary J. 71(12):414-417, Dec. 1994.
Crerar et al., "Epidemiological and clinical investigations into big liver and spleen disease of broiler breeder hens," Australian Veterinary J. 71(12):410-413, Dec. 1994.
Todd et al., "Development of an Enzyme-Linked Immunosorbent Assay for the Serological Diagnosis of Big Liver and Spleen Disease," Avian Diseases 37:811-816, 1993.
Handlinger et al., "An Egg Drop Associated with Splenomegaly in Broiler Breeders," Avian Diseases 32:773-778, 1988.
Larski, "Some new data concerning virology," Medycyna Weterynaryjna 56(7):415-419, 2000 (English abstract).
Williams et al., "A New Disease of Broiler Breeders—Big Liver and Spleen Disease," pp. 563-568, in Virus Infections of Birds, eds. McFerran & McNulty, Elsevier Science, 1993.
Payne et al., "The detection of the big liver and spleen agent in infected tissues via intravenous chick embryo inoculation," Avian Pathology 22:245-256, 1993.
Payne et al., "The detection of big liver and spleen disease-associated antigen in tissues from infected birds," Poultry Science 72(supp. 1):130, 1993 (abstract 390).
Payne et al., "Big liver and spleen disease of broiler breeders," Poultry Science 72(supp. 1):67, 1993 (abstract 200).

(Continued)

*Primary Examiner*—Bo Peng
(74) *Attorney, Agent, or Firm*—Anne M. Rosenblum

(57) ABSTRACT

The present invention relates to a novel isolated avian hepatitis E virus having a nucleotide sequence set forth in SEQ ID NO:1 or its complementary strand. The invention further concerns immunogenic compositions comprising this new virus or recombinant products such as the nucleic acid and vaccines that protect an avian or mammalian species from viral infection or hepatitis-splenomegaly syndrome caused by the hepatitis E virus. Also included in the scope of the invention is a method for propagating, inactivating or attenuating a hepatitis E virus comprising inoculating an embryonated chicken egg with a live, pathogenic hepatitis E virus and recovering the virus or serially passing the pathogenic virus through additional embryonated chicken eggs until the virus is rendered inactivated or attenuated. Further, this invention concerns diagnostic reagents for detecting an avian hepatitis E viral infection or diagnosing hepatitis-splenomegaly syndrome in an avian or mammalian species comprising an antibody raised or produced against the immunogenic compositions and antigens such as ORF2 proteins expressed in a baculovirus vector, *E. coli*, etc. The invention additionally encompasses methods for detecting avian HEV nucleic acid sequences using nucleic acid hybridization probes or oligonucleotide primers for polymerase chain reaction (PCR).

8 Claims, 35 Drawing Sheets

OTHER PUBLICATIONS

Clarke et al., "Big Liver and Spleen Disease of Broiler Breeders," Avian Pathology 19:41-50, 1990.

Barnes, "Big Liver and Spleen Disease," pp. 1038-1040, in Diseases of Poultry, eds. Calnek et al., pub. Iowa State University Press, 1997.

Ran et al., "Location and distribution of BLS antigen in the immune organs of big liver and spleen (BLS) disease in broiler breeders," Journal of Nanjing Agricultural Univ. 23(1):77-80, 2000 (English abstract).

Xu et al., "The ultrastructural studies of big liver and spleen (BLS) disease on [sic] broiler breeders," Journal of Nanjing Agricultural Univ. 22(1):87-90, 1999 (English abstract).

Yang et al., "Serological investigation of big liver and spleen disease in chickens on some farms," Chinese J. Vet. Sci. & Technol. 27(6):13-14, 1997 (English abstract supplied).

Tan et al., "Preliminary epidemiological investigation of big liver and spleen disease in chickens," Chinese J. Vet. Sci. & Technol. 26(1):16-17, 1996 (English abstract supplied).

G. Haqshenas et al., "Genetic identification and characterization of a novel virus related to human hepatitis E virus from chickens with hepatitis-splenomegaly syndrome in the United States," J. of General Virology 82:2449-2462, 2001.

Xiang-Jin Meng, "Novel strains of hepatitis E virus identified from humans and other animal species: is hepatitis E a zoonosis?" J. Hepatology 33(5):842-845, Nov. 2000.

Guo et al., "Immunodominant epitopes mapped by synthetic peptides on the capsid protein of avian hepatitis E virus are non-protective," Viral Immunol. 21(1):61-67, Mar. 2008.

F.F. Huang et al., "Determination and analysis of the complete genomic sequence of avian hepatitis E virus (avian HEV) and attempts to infect rhesus monkeys with avian HEV," J. Gen. Virol. 85 (Pt. 6):1609-1618, Jun. 2004.

M.A. Riddell et al., "Identification of immunodominant and conformational epitopes in the capsid protein of hepatitis E virus by using monoclonal antibodies," J. Virol. 74(17):8011-8017, Sep. 2000.

```
Avian HEV USA     TGTCGTGGTTTTGGGGTTTTAGGTTGATTTTCTGTATCTGGGCGTAAATTGCCCCTATGTTTAATTTA 70
Burma             -------------------------..T....G..------..T..---------....CT.C...C-.--G29
D11092 China      -------------------------..T....G..------..T..---------....CT.C...C-.--G29
D11093 China      -------------------------..T....G..------..T..---------....CT.C...C-.--G29
HEV-T1 China      -------------------------..T....G..------..T..---------....CT.C.GCC..--G30
Hetian China      -------------------------..T....G..------..T..---------....CT.C...C-.--G29
Hyderabad India   -------------------------..T....G..------..T..---------....CT.C.C.C-.--G29
L25547 China      -------------------------..T....G..------..T..---------....CT.T...C-.--G29
Mexico            -------------------------..T....GGC------..T..---------..A.CTAC..AT..C.G32
Myanmar           -------------------------..T..C.G..------..T..---------....CT.C...C-.--G29
Nepal             -------------------------..T....G..------..T..---------....CT.C.C.C-.--G29
SAR-55 Pakistan   -------------------------..T....G..------..T..---------....CT.C...C-.--G29
Swine HEV USA     -------------------------..A....C-..------TT.T--------G...CC.TCA..GC..C31
US1 USA           -------------------------..A....C-..------..T.T--------G...CC.TCGC.G..CT31
US2 USA           -------------------------..A....C-..------CT.T--------G...CC.TCG..G..CT31
X98292 India      -------------------------..T....G..------..T..---------....CT.C...C-.--G29

Avian HEV USA     TTGTGATTTTTATAACTGTTCATTTGATTATTTATGAAATCCTCCCATCTCGGGCATAGT         127
Burma             ...------C----------.T.....C-.C.....C..CGT...G.G.TC.CT.                65
D11092 China      ...------C----------.T.....C-.CT....C..CGT...G.G.TC.CT.                65
D11093 China      ...------C----------.T.....C-.CT....C..CGT...G.G.TC.CT.                65
HEV-T1 China      ..T------.C---------..T....C-CCT....C..CGTC..G.G.TC.CT.                68
Hetian China      ...------C----------.T.....C-.C.....C..CGT...G.G.TC.CT.                65
Hyderabad India   ...------C----------.T.....C-.C.....C..CGT...G.G.TC.CT.                65
L25547 China      ...------C----------.T.....C-.CT....C..CGT.T.G.G.TC.CT.                65
Mexico            C..--....CC---------.T.....C-C.T....C.CGGTC..G.G.TC.CT.                74
Myanmar           ...------C----------.T.....C-........C..CGT...G.G.TC.CT.               65
Nepal             ...------C----------.T.....C-.CT....C..CGT...G.G.TC.CT.                65
SAR-55 Pakistan   ...------C----------.T.....                                            39
Swine HEV USA     C.----..GG.---------..T....C-........C..CTT...G.G.TC.CT..              72
US1 USA           C.----..GGC---------..T....C-.C.....C..CTT...G.G.TC.CT..               72
US2 USA           ..----..CGC---------..T....C-........C..CTT...G.G.TC.CT..              72
X98292 India      C..------C----------.T.....C-.CT....C..CGT.T.G.G.TC.CT.                65
```

ACCAGCATTGGATTTCGATGGACGCTGTTTAACGAGCGCCGTTGATCTTGGG
TTGCAGCCTACCAGCTGGCGCACCGTATCCCACCGTTGCCCTTGGGACGTTT
GTATATTTTGCGTACTGATTATCCGACTATCACCACAACCAGTAGGGTGCT
GCGGTCTGTTGTGTTTACCGGTGAAACCATTGGTCAGAAGATAGTGTTTACC
CAGGTGGCCAAGCAGTCGAACCCCGGGTCCATAACGGTCCATGAGGCGCAG
GGCAGTACTTTTGATCAGACTACTATAATCGCCACGTTAGATGCTCGTGGCC
TTATAGCTTCATCTCGCGCGCATGCCATAGTTGCGCTAACCCGCCACCGGGA
GCGCTGTAGTGTGATTGATGTTGGTGGGGTGCTGGTCGAGATTGGAGTTACT
GATGCCATGTTTAACAATATCGAAATGCAGCTTGTGCGACCTGATGCTGCAG
CCCCTGCCGGGGTGCTACGAGCCCCAGACGACACCGTGGATGGCTTGTTGGA
CATACCCCCGGCCCACACTGATGTAGCGGCGGTGTTAACAGCTGAGGCGATT
GGGCATGCGCCCCTTGAATTGGCCGCCATAAATCCACCCGGGCCTGTATTGG
AGCAGGGCCTATTATACATGCCGGCCAGGCTTGATGGGCGTGATGAGGTTGT
TAAGCTCCAGCTGTCGGATACTGTACACTGCCGCCTGGCTGCACCCACTAGC
CGTCTTGCGGTGATTAACACATTGGTTGGGCGGTACGGTAAAGCCACTAAGC
TGCCTGAGGTTGAATATGACTTAATGGACACTATTGCGCAGTTCTGGCATCA
TATCGGACCAATCAACCCCTCAACACTGGAGTATGCAGAGATGTGCGAGGC
CATGCTTAGTAAGGGCCAGGATGGGTCCTTGATTGTACATCTGGATTTACAG
GATGCTGATTGTTCTCGCATAACATTCTTCCAGAAGGACTGCGCTAAATTTA
CGCTGGATGACCCTGTTGCACACGGTAAAGTGGGACAGGGGATATCTGCGT
GGCCGAAAACTTTGTGTGCACTTTTCGGCCCCTGGTTCCGGGCTATAGAGAA
GCACCTTGTGGCTGGGTTACCCCAGGTTATTATGGGGACCTGTACACG
GAAGCCGATCTGCATCGTTCTGTGCTTTGCGCGCCTGCTGGTCACCTTGTTTT
TGAGAATGATTTCTCAGAGTTTGACTCAACGCAGAATAATGTGTCCCTTGAT
CTCGAATGTGAATTGATGCGCAGGTTTGGGATGCCCGATTGGATGGTAGCCT
TGTACCATCTTGTTCGATCATACTGGCTCTTGGTTGCCCCGAAAGAAGCCCTT
CGTGGCTGTTGGAAAAAACACTCTGGTGAGCCGGGCACCCTTTTGTGGAATA
CAGTTTGGAACATGACTGTGTTGCATCATGTTTATGAGTTTGATCGACCAAG
TGTGTTGTGTTTCAAAGGTGATGATAGTGTCGTTGTCTGTGAATCGGTGCGC

Fig. 9B

GCCCGTCCAGAGGGCGTTAGTCTCGTGGCAGACTGCGGGCTAAAAATGAAG
GACAAGACCGGCCCGTGTGGCGCCTTTTCCAACCTGCTGATCTTCCCGGGAG
CTGGTGTTGTCTGCGACCTGTTACGGCAGTGGGGCCGCTTGACTGACAAGAA
CTGGGGGCCCGACATTCAGCGGATGCAGGACCTTGAGCAAGCGTGTAAGGA
TTTTGTTGCACGTGTTGTAACTCAGGGTAAAGAGATGTTGACCATCCAGCTT
GTGGCGGGTTATTATGGTGTGGAAGTTGGTATGGTTGAGGTGGTTTGGGGGG
CTTTGAAGGCCTGCGCCGCAGCCCGCGAGACCCTAGTGACCAACAGGTTGCC
GGTACTAAACTTATCTAAGGAGGACTGAACAAATAACAATCATTATGCAGT
CTGCGCGTCCATGTGCCTTAGCTGCCAGTTCTGGTGTTTGGAGTGCCAGGAA
AGTGGGGTGGGATGTCGCTGTGTAGATTGTTGCTCATGCTTGCAATGTGCTG
CGGGGTGTCAAGGGGCTCCCAAACGCTCCCAGCCGGAGGCAGGCGTGGCCA
GCGCCGCCGTGACAATTCAGCCCAGTGGAGCACTCAACAACGCCCCGAGGG
AGCCGTCGGCCCCGCCCTCTCACAGACGTTGTCACCGCGGCAGGTACTCGC
ACGGTACCAGATGTAGATCAAGCCGGTGCCGTGCTGGTGCGCCAGTATAATC
TAGTGACCAGCCCGTTAGGCCTGGCCACCCTTGGTAGCACCAATGCCTTGCT
TTATGCCGCACCGGTGTCACCGTTAATGCCGCTTCAGGACGGCACGACGTCT
AATATCATGAGCACGGAGTCTAGCAACTATGCTCAATACCGTGTACAGGGCC
TAACTGTCCGCTGGCGCCCAGTTGTGCCAAATGCGGTGGGCGGCTTCTCTAT
AAGCATGGCCTATTGGCCCCAGACAACATCCACCCCTACAAGCATTGACATG
AATTCCATCACGTCCACTGACGTCCGTGTGGTGCTTCAGCCGGGCTCTGCTG
GTTTGCTGACTATACCACATGAGCGTTTGGCGTATAAGAACAATGGTTGGCG
GTCCGTCGAAACGGTATCCGTCCCACAGGAGGATGCCACGTCCGGCATGCTC
ATGGTTTGTGTCCACGGGACCCCCTGGAATAGTTATACCAATAGTGTTTACA
CCGGGCCGCTTGGTATGGTTGATTTTGCCATAAAGTTACAGCTAAGGAACTT
GTCGCCCGGTAATACAAATGCCAGGGTCACCCGTGTGAAGGTGACGGCCCC
ACATACCATCAAGGCTGACCCATCTGGTGCTACCATAACAACAGCAGCTGCG
GCCAGGTTTATGGCGGATGTGCGTTGGGGCTTGGGCACTGCTGAGGATGGCG
AAATTGGTCACGGCATCCTTGGTGTTCTGTTTAACCTGGCGGACACAGTTTT
AGGTGGCTTGCCCTCGACACTGCTGCGGGCGGCGAGTGGTCAGTACATGTAC

Fig. 9C

GGCCGGCCTGTGGGGAACGCGAACGGCGAGCCTGAGGTGAAACTGTATATG
TCGGTTGAGGATGCCGTTAACGATAAACCTATTATGGTCCCCCATGACATCG
ACCTCGGGACCAGCACTGTCACCTGCCAGGACTATGGGAATCAGCATGTGG
ATGACCGCCCATCCCCGGCCCCGGCCCCTAAGCGAGCTTTGGGCACCCTAAG
GTCAGGGGATGTGTTGCGTATTACTGGCTCCATGCAGTATGTGACTAACGCC
GAGTTGTTACCGCAGAGTGTGTCACAGGGGTACTTTGGGGCCGGCAGCACC
ATGATGGTGCATAATTTGATCACTGGTGTGCGCGCCCCGCCAGTTCAGTCG
ACTGGACGAAGGCAACAGTGGATGGGGTCCAGGTGAAGACTGTCGATGCTA
GTTCTGGGAGTAATAGGTTTGCAGCGTTACCTGCATTTGGAAAGCCAGCTGT
GTGGGGGCCCCAGGGCGCTGGGTATTTCTACCAGTATAACAGCACCCACCA
GGAGTGGATTTATTTTCTTCAGAATGGTAGCTCCGTGGTTTGGTATGCATATA
CTAATATGTTGGGCCAGAAGTCAGATACATCCATTCTTTTGAGGTCCGGCC
AATCCAAGCTAGTGATCAGCCTTGGTTTTTGGCACACCACACTGGCGGCGA
TGACTGTACCACCTGTCTGCCTCTGGGGTTAAGAACATGTTGCCGCCAGGCG
CCAGAAGACCAGTCACCTGAGACGCGCCGGCTCCTAGACCGGCTTAGTAGG
ACATTCCCCTCACCACCCTAATGTCGTGGTTTTGGGGTTTTAGGTTGATTTTC
TGTATCTGGGCGTAATTGCCCCTATGTTTAATTTATTGTGATTTTTATAACTG
TTCATTTGATTATTTATGAAATCCTCCCATCTCGGGCATAGTAAAAAAAAAA
AAAAA

Fig. 10

PALDFDGRCLTSAVDLGLQPTSWRTVSHRCPWDVCIFLRTDYPTITTTSRVLRSV
VFTGETIGQKIVFTQVAKQSNPGSITVHEAQGSTFDQTTIIATLDARGLIASSRAH
AIVALTRHRERCSVIDVGGVLVEIGVTDAMFNNIE

Fig. 11

ACCAGCATTGGATTTCGATGGACGCTGTTTAACGAGCGCCGTTGATCTTGGG
TTGCAGCCTACCAGCTGGCGCACCGTATCCCACCGTTGCCCTTGGGACGTTT
GTATATTTTGCGTACTGATTATCCGACTATCACCACAACCAGTAGGGTGCT
GCGGTCTGTTGTGTTTACCGGTGAAACCATTGGTCAGAAGATAGTGTTTACC
CAGGTGGCCAAGCAGTCGAACCCCGGGTCCATAACGGTCCATGAGGCGCAG
GGCAGTACTTTTGATCAGACTACTATAATCGCCACGTTAGATGCTCGTGGCC
TTATAGCTTCATCTCGCGCGCATGCCATAGTTGCGCTAACCCGCCACCGGGA
GCGCTGTAGTGTGATTGATGTTGGTGGGGTGCTGGTCGAGATTGGAGTTACT
GATGCCATGTTTAACAATATCGAA

Fig. 12

LVRPDAAAPAGVLRAPDDTVDGLLDIPPAHTDVAAVLTAEAIGHAPLELAAINP
PGPVLEQGLLYMPARLDGRDEVVKLQLSDTVHCRLAAPTSRLAVINTLVGRYG
KATKLPEVEYDLMDTIAQFWHHIGPINPSTLEYAEMCEAMLSKGQDGSLIVHLD
LQDADCSRITFFQKDCAKFTLDDPVAHGKVGQGISAWPKTLCALFGPWFRAIEK
HLVAGLPPGYYYGDLYTEADLHRSVLCAPAGHLVFENDFSEFDSTQNNVSLDL
ECELMRRFGMPDWMVALYHLVRSYWLLVAPKEALRGCWKKHSGEPGTLLWN
TVWNMTVLHHVYEFDRPSVLCFKGDDSVVVCESVRARPEGVSLVADCGLKMK
DKTGPCGAFSNLLIFPGAGVVCDLLRQWGRLTDKNWGPDIQRMQDLEQACKDF
VARVVTQGKEMLTIQLVAGYYGVEVGMVEVVWGALKACAAARETLVTNRLP
VLNLSKED

Fig. 13 gcttgtgcgacctgatgctgcagcccctgccggggtgctacgagccccagacgacaccgtggatggcttgttggacataccc
ccggcccacactgatgtagcggcggtgttaacagctgaggcgattgggcatgcgccccttgaattggccgccataaatccacc
cggggcctgtattggagcagggcctattatacatgccggccaggcttgatgggcgtgatgaggttgttaagctccagctgtcgga
tactgtacactgccgcctggctgcacccactagccgtcttgcggtgattaacacattggttgggcggtacggtaaagccactaa
gctgcctgaggttgaatatgacttaatggacactattgcgcagttctggcatcatatcggaccaatcaacccctcaacactggagt
atgcagagatgtgcgaggccatgcttagtaagggccaggatgggtccttgattgtacatctggatttacaggatgctgattgttct
cgcataacattcttccagaaggactgcgctaaatttacgctggatgaccctgttgcacacggtaaagtgggacaggggatatct
gcgtggccgaaaactttgtgtgcacttttcggcccctggttccgggctatagagaagcaccttgtggctgggttaccccaggtt
attactatggggacctgtacacggaagccgatctgcatcgttctgtgctttgcgcgcctgctggtcaccttgttttgagaatgattt
ctcagagtttgactcaacgcagaataatgtgtcccttgatctcgaatgtgaattgatgcgcaggtttgggatgcccgattggatgg
tagccttgtaccatcttgttcgatcatactggctcttggttgccccgaaagaagcccttcgtggctgttggaaaaaaacactctggtg
agccgggcacccttttgtggaatacagtttggaacatgactgtgttgcatcatgtttatgagtttgatcgaccaagtgtgttgtgtttc
aaaggtgatgatagtgtcgttgtctgtgaatcggtgcgcgcccgtccagagggcgttagtctcgtggcagactgcgggctaaa
aatgaaggacaagaccggcccgtgtggcgccttttccaacctgctgatcttcccggggagctggtgttgtctgcgacctgttacg
gcagtggggccgcttgactgacaagaactgggggcccgacattcagcggatgcaggaccttgagcaagcgtgtaaggatttt
gttgcacgtgttgtaactcagggtaaagagatgttgaccatccagcttgtggcgggttattatggtgtggaagttggtatggttg
aggtggtttggggggctttgaaggcctgcgccgcagcccgcgagaccctagtgaccaacaggttgccggtactaaacttatc
taaggaggac

Fig. 14

MSLCRLLLMLAMCCGVSRGSQTLPAGGRRGQRRRDNSAQWSTQQRPEGAVGP
APLTDVVTAAGTRTVPDVDQAGAVLVRQYNLVTSPLGLATLGSTNALLYAAPV
SPLMPLQDGTTSNIMSTESSNYAQYRVQGLTVRWRPVVPNAVGGFSISMAYWP
QTTSTPTSIDMNSITSTDVRVVLQPGSAGLLTIPHERLAYKNNGWRSVETVSVPQ
EDATSGMLMVCVHGTPWNSYTNSVYTGPLGMVDFAIKLQLRNLSPGNTNARV
TRVKVTAPHTIKADPSGATITTAAAARFMADVRWGLGTAEDGEIGHGILGVLF
NLADTVLGGLPSTLLRAASGQYMYGRPVGNANGEPEVKLYMSVEDAVNDKPI
MVPHDIDLGTSTVTCQDYGNQHVDDRPSPAPAPKRALGTLRSGDVLRITGSMQ
YVTNAELLPQSVSQGYFGAGSTMMVHNLITGVRAPASSVDWTKATVDGVQVK
TVDASSGSNRFAALPAFGKPAVWGPQGAGYFYQYNSTHQEWIYFLQNGSSVV
WYAYTNMLGQKSDTSILFEVRPIQASDQPWFLAHHTGGDDCTTCLPLGLRTCC
RQAPEDQSPETRRLLDRLSRTFPSPP

Fig. 15 atgtcgctgtgtagattgttgctcatgcttgcaatgtgctgcggggtgtcaaggggctcccaaacgctcccagccggaggcagg
cgtggccagcgccgccgtgacaattcagcccagtggagcactcaacaacgccccgagggagccgtcggccccgcccctct
cacagacgttgtcaccgcggcaggtactcgcacggtaccagatgtagatcaagccggtgccgtgctggtgcgccagtataatc
tagtgaccagcccgttaggcctggccacccttggtagcaccaatgccttgctttatgccgcaccggtgtcaccgttaatgccgct
tcaggacggcacgacgtctaatatcatgagcacggagtctagcaactatgctcaataccgtgtacagggcctaactgtccgctg
gcgcccagttgtgccaaatgcggtgggcggcttctctataagcatggcctattggccccagacaacatccacccctacaagcat
tgacatgaattccatcacgtccactgacgtccgtgtggtgcttcagccgggctctgctggtttgctgactataccacatgagcgttt
ggcgtataagaacaatggttggcggtccgtcgaaacggtatccgtcccacaggaggatgccacgtccggcatgctcatggttt
gtgtccacgggacccctggaatagttataccaatagtgtttacaccgggccgcttggtatggttgattttgccataaagttacag
ctaaggaacttgtcgcccggtaatacaaatgccagggtcacccgtgtgaaggtgacggccccacataccatcaaggctgacc
catctggtgctaccataacaacagcagctgcggccaggtttatggcggatgtgcgttggggcttgggcactgctgaggatggc
gaaattggtcacggcatccttggtgttctgtttaacctggcggacacagttttaggtggcttgccctcgacactgctgcgggcgg
cgagtggtcagtacatgtacggccggcctgtggggaacgcgaacggcgagcctgaggtgaaactgtatatgtcggttgagga
tgccgttaacgataaacctattatggtcccccatgacatcgacctcgggaccagcactgtcacctgccaggactatgggaatca
gcatgtggatgaccgcccatccccggccccggcccctaagcgagctttgggcaccctaaggtcaggggatgtgttgcgtatta
ctggctccatgcagtatgtgactaacgccgagttgttaccgcagagtgtgtcacaggggtactttggggccggcagcaccatg
atggtgcataatttgatcactggtgtgcgcgccccgccagttcagtcgactggacgaaggcaacagtggatggggtccaggt
gaagactgtcgatgctagttctgggagtaataggtttgcagcgttacctgcatttggaaagccagctgtgtgggggccccaggg
cgctgggtatttctaccagtataacagcacccaccaggagtggatttatttcttcagaatggtagctccgtggtttggtatgcatat
actaatatgttgggccagaagtcagatacatccattcttttgaggtccggccaatccaagctagtgatcagccttggttttggca
caccacactggcggcgatgactgtaccacctgtctgcctctggggttaagaacatgttgccgccaggcgccagaagaccagtc
acctgagacgcgccggctcctagaccggcttagtaggacattcccctcaccaccctaa

Fig. 16

MCLSCQFWCLECQESGVGCRCVDCCSCLQCAAGCQGAPKRSQPEAGVASAAV
TIQPSGALNNAPREPSAPPLSQTLSPRQVLARYQM

Fig. 17 atgtgccttagctgccagttctggtgtttggagtgccaggaaagtggggtgggatgtcgctgtgtagattgttgctcatgcttgca
atgtgctgcggggtgtcaaggggctcccaaacgctcccagccggaggcaggcgtggccagcgccgccgtgacaattcagc
ccagtggagcactcaacaacgccccgagggagccgtcggccccgcccctctcacagacgttgtcaccgcggcaggtactcg
cacggtaccagatgtag Fig. 18A
Fig. 18B

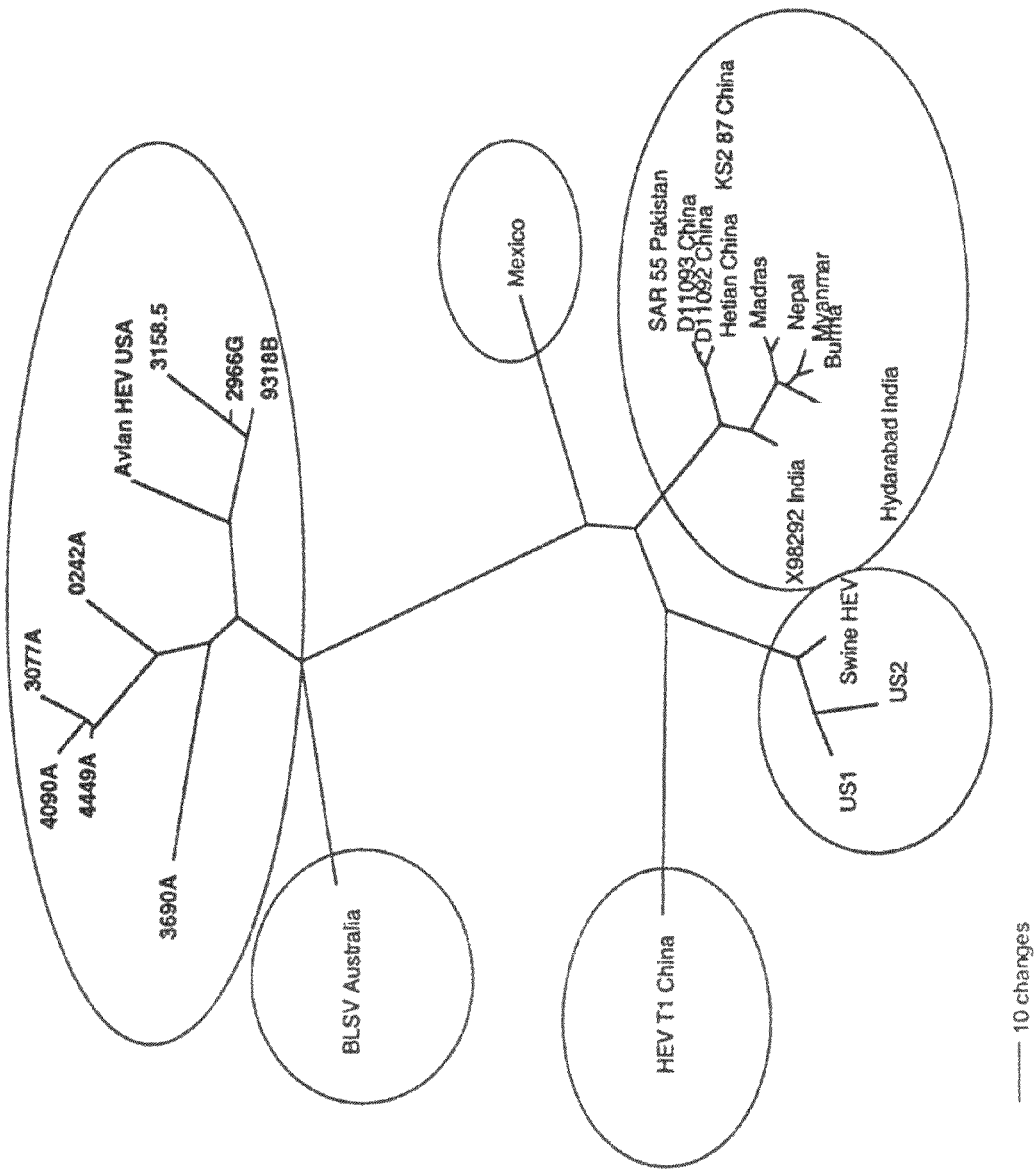

Fig. 21A
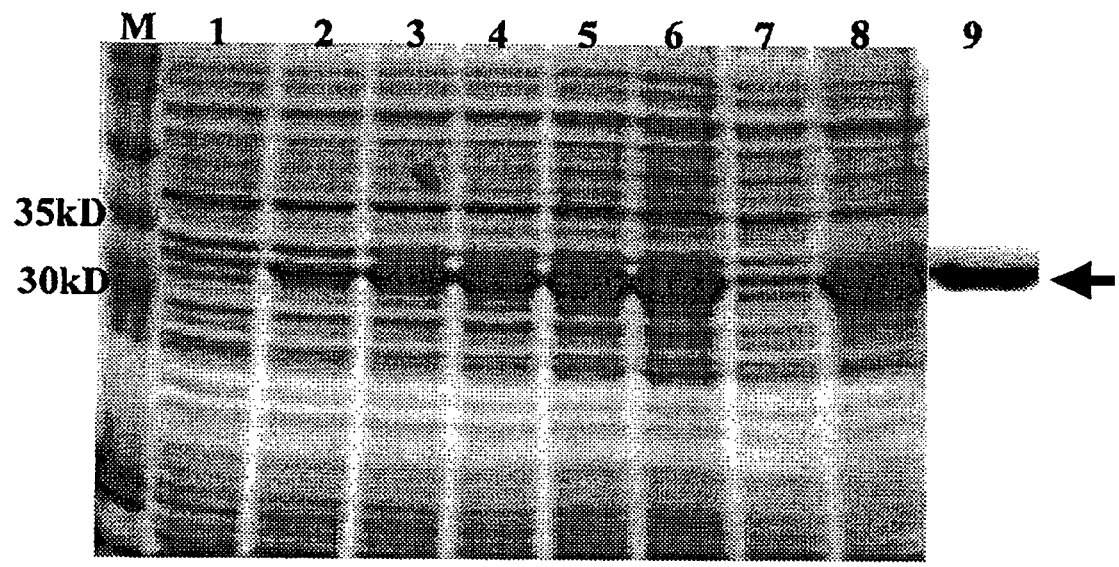
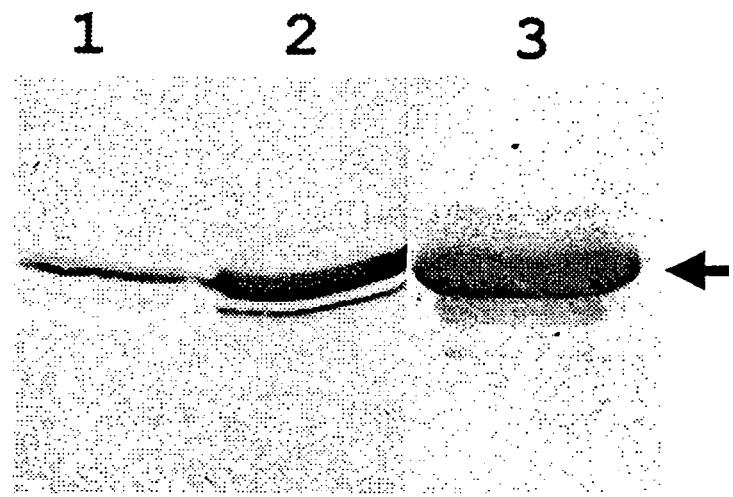
Fig. 21B

Fig. 24

```
Avian HEV   QYMYGRPVGNANGEPEVKLYMSVEDAVNDKPIMVPHDIDLGTSTVTCQDY
Swine HEV   .LF.S...VS.....T....T...N.QQ..G.TI.......D.R.VI...
US-2        .LF.S...VS.....T....T...N.QQ..G.TI.......D.R.VI...
Sar-55      .LF.S...VS.....T....T...N.QQ..G.AI.......E.R.VI...

Avian HEV   GNQHVDDRPSPAPAPKRALGTLRSGDVLRITGSMQYVTNAELLPQSVSQG
Swine HEV   D...EQ...T.S...S.PFSV..AN...WLSLTA---AEYDQTTYGS.TN
US-2        D...EQ...T.S...S.PFSV..AN...WLSLTA---AEYDQTTYGS.TN
Sar-55      D...EQ...T.S...S.PFSV..AN...WLSLTA---AEYDQS TYGS.T Avian HEV   YFGAGSTMMVHNLITGVRAPASSVDWTKATVDGVQVKTVDASSGSNRFAAL
Swine HEV   PMYVSD.VTLV.VA..AQ.V.R.L..S.V.L..RPLT.IQQY.KT--.YV.
US-2        PMYVSD.VTLV.VA..AQ.V.R.L..S.V.L..RPLT.IQQY.KT--.YV.
Sar-55      PVYVSDSVTLV.VA..AQ.V.R.L....V.L..RPLS.IQQY.KT--.FV.

Avian HEV   PAFGKPAVWGP--QGAGYFYQYNSTHQEWIYFLQN-GSSVVWYAYTNMLGQ
Swine HEV   .LR..LSF.EAGTTK...PYN..T.ASDQ.LIENAA.HRVAIST..TS..A
US-2        .LR..LSF.EAGTTK...PYN..T.ASDQ.LIENAA.HRVAIST..TS..A
Sar-55      .LR..LSF.EAGTTK...PYN..T.ASDQLLIENAA.HRVAIST..TS..A Avian HEV   K----SDTSILFEVRPIQASDQ--PWFLAHHTGGDDCTTCLPLGLRTCCRQ
Swine HEV   GPTSI.AVGV.APHSALAVLEDTVDYPARA..FD.F.PE.RT...QG.AF.
US-2        GPTSI.AVGV.APHSALAVLEDTIDYPARA..FD.F.PE.RT...QG.AF.
Sar-55      GPVSI.AVAV.APHSVLALLEDTMDYPARA..FD.F.PE.RP...QG.AF.

Avian HEV   APEDQSPETRRLLDRLSRTFPSPP
Swine HEV   S---TIA.LQ..KMKVGK.RE.--
US-2        S---TIA.LQ..KMKVGK.RE.--
Sar-55      S---TVA.LQ..KMKVGK.REL--
```

Fig. 25A
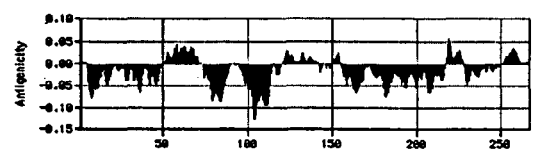 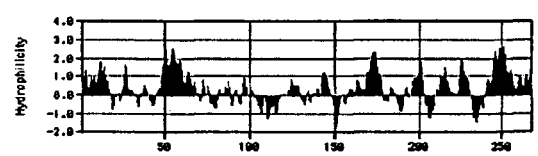
Fig. 25B
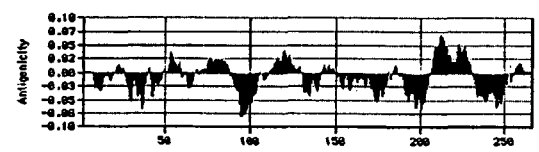 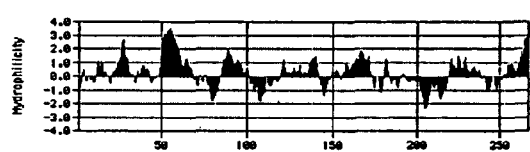
Fig. 25C
 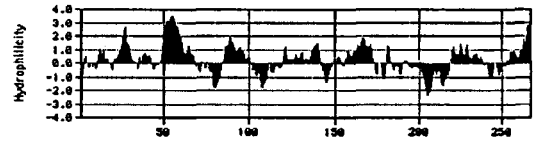
Fig. 25D
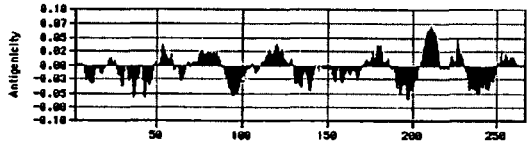 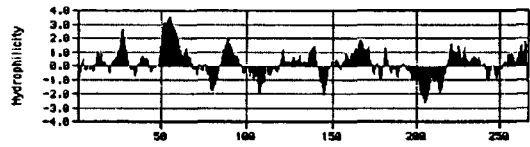

AVIAN HEPATITIS E VIRUS, VACCINES AND METHODS OF PROTECTING AGAINST AVIAN HEPATITIS-SPLENOMEGALY SYNDROME AND MAMMALIAN HEPATITIS E

CROSS-REFERENCE TO RELATED U.S. APPLICATIONS

This application is a division of U.S. application Ser. No. 11/184,574, now U.S. Pat. No. 7,582,303, filed on Jul. 19, 2005, which, in turn, claims the benefit under 35 U.S.C. §120 of the prior U.S. application Ser. No. 10/029,840, filed on Dec. 31, 2001, now U.S. Pat. No. 7,005,130, which claims the benefit under 35 U.S.C. §119(e) of U.S. Provisional Application No. 60/259,846, filed Jan. 5, 2001, abandoned.

STATEMENT REGARDING FEDERALLY SPONSORED RESEARCH OR DEVELOPMENT

The project resulting in the present invention has been supported in part by grants from the National Institutes of Health (AI01653-01, AI46505-01).

REFERENCE TO A "Sequence Listing"

The material on a single compact disc containing a Sequence Listing file provided in this application is incorporated by reference. The date of creation is Sep. 9, 2002 and the size is approximately 21.4 KB.

BACKGROUND OF THE INVENTION

1. Field of the Invention

The present invention concerns a novel avian hepatitis E virus, immunogenic compositions, diagnostic reagents, vaccines and methods of detecting or protecting against avian hepatitis-splenomegaly syndrome and mammalian hepatitis E.

2. Description of the Related Art

Human hepatitis E is an important public health disease in many developing countries, and is also endemic in some industrialized countries. Hepatitis E virus (hereinafter referred to as "HEV"), the causative agent of human hepatitis E, is a single positive-stranded RNA virus without an envelope (R. H. Purcell, "Hepatitis E virus," FIELDS VIROLOGY, Vol. 2, pp. 2831-2843, B. N. Fields et al. eds, Lippincott-Raven Publishers, Philadelphia (3d ed. 1996)). The main route of transmission is fecal-oral, and the disease reportedly has a high mortality rate, up to 20%, in infected pregnant women. The existence of a population of individuals who are positive for HEV antibodies (anti-HEV) in industrialized countries and the recent identification of numerous genetically distinct strains of HEV have led to a hypothesis that an animal reservoir for HEV exists (X. J. Meng, "Zoonotic and xenozoonotic risks of hepatitis E virus," Infect. Dis. Rev. 2:35-41 (2000); X. J. Meng, "Novel strains of hepatitis E virus identified from humans and other animal species: Is hepatitis E a zoonosis?" J. Hepatol. 33:842-845 (2000)). In 1997, the first animal strain of HEV, swine hepatitis E virus (hereinafter referred to as "swine HEV"), was identified and characterized from a pig in the U.S. (X. J. Meng et al., "A novel virus in swine is closely related to the human hepatitis E virus," Proc. Natl. Acad. Sci. USA 94:9860-9865 (1997)). Swine HEV was shown to be very closely related genetically to human HEV. Interspecies transmission of HEV has been documented: swine HEV infects non-human primates and a U.S. strain of human HEV infects pigs. These data lend further credence to the hypothesis of an animal reservoir for HEV.

Numerous genetically distinct strains of HEV have been identified from patients with acute hepatitis in both developing and industrialized countries. The two U.S. strains of human HEV recently identified from hepatitis E patients (US-1 and US-2) are genetically distinct from other known HEV strains worldwide but are closely related to each other and to the U.S. strain of swine HEV (J. C. Erker et al., "A hepatitis E virus variant from the United States: molecular characterization and transmission in cynomolgus macaques," J. Gen. Virol. 80:681-690 (1999); X. J. Meng et al., "Genetic and experimental evidence for cross-species infection by the swine hepatitis E virus," J. Virol. 72:9714-9721 (1998); G. G. Schlauder et al., "The sequence and phylogenetic analysis of a novel hepatitis E virus isolated from a patient with acute hepatitis reported in the United States," J. Gen. Virol. 79:447-456 (1998)). Similarly, several isolates of HEV have been identified from patients in Taiwan with no history of travel to endemic region. An Italian strain of human HEV was found to share only about 79.5 to 85.8% nucleotide sequence identity with other known strains of HEV. Schlauder et al. recently identified another Italian and two Greek strains of HEV (G. G. Schlauder et al., "Novel hepatitis E virus (HEV) isolates from Europe: evidence for additional genotypes of HEV," J. Med. Virol. 57:243-51 (1999)). The sequences of the Greek and Italian strains of HEV differed significantly from other known strains of HEV. In endemic regions, strains of HEV, which are distinct from the previously known epidemic strains, have also been identified in Pakistan (H. Van Cuyck-Gandre et al., "Short report: phylogenetically distinct hepatitis E viruses in Pakistan," Am. J. Trop. Med. Hyg. 62:187-189 (2000)), Nigeria (Y. Buisson et al., "Identification of a novel hepatitis E virus in Nigeria," J. Gen. Virol. 81:903-909 (2000)) and China (Y. Wang et al., "A divergent genotype of hepatitis E virus in Chinese patients with acute hepatitis," J. Gen. Virol. 80:169-77 (1999); Y. Wang et al., "The complete sequence of hepatitis E virus genotype 4 reveals an alternative strategy for translation of open reading frames 2 and 3," J. Gen. Virol. 81:1675-1686 (2000)). Six isolates of HEV were identified from Chinese hepatitis E patients that were negative for anti-HEV assayed by the serological test used (Y. Wang et al., 1999, supra). The intriguing fact is that these recently identified strains of HEV are genetically distinct from each other and from other known strains of HEV. Although the source of these human HEV strains is not clear, it is plausible that they may be of animal origins.

Recently, several U.S. patents have issued which concern the human hepatitis E virus. U.S. Pat. No. 6,022,685 describes methods and compositions for detecting anti-hepatitis E virus activity via antigenic peptides and polypeptides. U.S. Pat. No. 5,885,768 discloses immunogenic peptides which are derived from the ORF1, ORF2 and ORF3 regions of hepatitis E virus, diagnostic reagents containing the peptide antigens, vaccines and immunoreactive antibodies. U.S. Pat. No. 5,770,689 relates to certain ORF Z peptides of the human HEV genome. U.S. Pat. No. 5,741,490 deals with a vaccine and vaccination method for preventing hepatitis E viral infections. U.S. Pat. No. 5,686,239 provides a method of detecting HEV antibodies in an individual using a peptide antigen obtained from the human HEV sequence.

Evidence of HEV infection of domestic and farm animals has been well documented (X. J. Meng, "Zoonotic and xenozoonotic risks of hepatitis E virus," Infect. Dis. Rev. 2:35-41 (2000); X. J. Meng, "Novel strains of hepatitis E virus identified from humans and other animal species: Is hepatitis E a zoonosis?" J. Hepatol., 33:842-845 (2000); R. H. Purcell, "Hepatitis E virus," FIELDS VIROLOGY, Vol. 2, pp. 2831-2843, B. N. Fields et al. eds, Lippincott-Raven Publishers, Philadelphia (3d ed. 1996)). Anti-HEV was detected in pigs from developing countries such as Nepal (E. T. Clayson et al., "Detection of hepatitis E virus infections among domestic swine in the Kathmandu Valley of Nepal," Am. J. Trop. Med. Hyg. 53:228-232 (1995)), China (X. J. Meng et al., "Prevalence of antibodies to the hepatitis E virus in pigs from countries where hepatitis E is common or is rare in the human population," J. Med. Virol. 58:297-302 (1999)) and Thailand (id), and from industrialized countries such as U.S. (X. J. Meng et al., "A novel virus in swine is closely related to the human hepatitis E virus," Proc. Natl. Acad. Sci. USA 94:9860-9865 (1997)), Canada (X. J. Meng et al., 1999, supra), Korea (X. J. Meng et al., 1999, id.), Taiwan (S. Y. Hsieh et al., "Identity of a novel swine hepatitis E virus in Taiwan forming a monophyletic group with Taiwan isolates of human hepatitis E virus," J. Clin. Microbiol. 37:3828-3834 (1999)), Spain (S. Pina et al., "HEV identified in serum from humans with acute hepatitis and in sewage of animal origin in Spain," J. Hepatol. 33:826-833 (2000)) and Australia (J. D. Chandler et al., "Serological evidence for swine hepatitis E virus infection in Australian pig herds," Vet. Microbiol. 68:95-105 (1999)). In addition to pigs, Kabrane-Lazizi et al. reported that about 77% of the rats from Maryland, 90% from Hawaii and 44% from Louisiana are positive for anti-HEV (Y. Kabrane-Lazizi et al., "Evidence for wide-spread infection of wild rats with hepatitis E virus in the United States," Am. J. Trop. Med. Hyg. 61:331-335 (1999)). Favorov et al. also reported the detection of IgG anti-HEV among rodents in the U.S. (M. O. Favorov et al., "Prevalence of antibody to hepatitis E virus among rodents in the United States," J. Infect. Dis. 181:449-455 (2000)). In Vietnam where HEV is endemic, anti-HEV was reportedly detected in 44% of chickens, 36% of pigs, 27% of dogs and 9% of rats (N. T. Tien et al., "Detection of immunoglobulin G to the hepatitis E virus among several animal species in Vietnam," Am. J. Trop. Med. Hyg. 57:211 (1997)). About 29 to 62% of cows from Somali, Tajikistan and Turkmenistan (HEV endemic regions), and about 42 to 67% of the sheep and goats from Turkmenistan and 12% of cows from Ukraine (a non-endemic region) are positive for anti-HEV (M. O. Favorov et al., "Is hepatitis E an emerging zoonotic disease?" Am. J. Trop. Med. Hyg. 59:242 (1998)). Naturally acquired anti-HEV has also been reported in rhesus monkeys (S. A. Tsarev et al., "Experimental hepatitis E in pregnant rhesus monkeys: failure to transmit hepatitis E virus (HEV) to offspring and evidence of naturally acquired antibodies to HEV," J. Infect. Dis. 172:31-37 (1995)). These serological data strongly suggest that these animal species are infected with HEV or a related agent. Until recently, the source of seropositivity in these animals could not be definitively demonstrated since the virus was either not recovered from these animal species or the recovered virus was not genetically characterized to confirm its identity. The first and only animal strain of HEV that has been identified and extensively characterized thus far is swine HEV (X. J. Meng et al., "A novel virus in swine is closely related to the human hepatitis E virus," Proc. Natl. Acad. Sci. USA 94:9860-9865 (1997); X. J. Meng et al., "Experimental infection of pigs with the newly identified swine hepatitis E virus (swine HEV), but not with human strains of HEV," Arch. Virol. 143:1405-1415 (1998); X. J. Meng et al., "Genetic and experimental evidence for cross-species infection by the swine hepatitis E virus," J. Virol. 72:9714-9721 (1998); X. J. Meng et al., "Prevalence of antibodies to the hepatitis E virus in pigs from countries where hepatitis E is common or is rare in the human population," J. Med. Virol. 58:297-302 (1999)). However, because swine HEV causes only subclinical infection and mild microscopic liver lesions in pigs, it does not provide a good, adaptable animal model to study human HEV replication and pathogenesis.

Since the identification and characterization of the first animal strain of HEV (swine HEV) in the U.S. in 1997, several other HEV strains of animal origins were genetically identified. Hsieh et al. identified a second strain of swine HEV from a pig in Taiwan (S. Y. Hsieh et al., "Identity of a novel swine hepatitis E virus in Taiwan forming a monophyletic group with Taiwan isolates of human hepatitis E virus," J. Clin. Microbiol. 37:3828-3834 (1999)). This Taiwanese strain of swine HEV shared 97.3% nucleotide sequence identity with a human strain of HEV identified from a retired Taiwanese farmer but is genetically distinct from other known strains of HEV including the U.S. strain of swine HEV. Recently, Pina et al. identified a strain of HEV (E11 strain) from sewage samples of animal origin from a slaughterhouse that primarily processed pigs in Spain (S. Pina et al., "HEV identified in serum from humans with acute hepatitis and in sewage of animal origin in Spain," J. Hepatol. 33:826-833 (2000)). The E11 strain of possible animal origin is most closely related to two Spanish strains of human HEV, and is more closely related to the U.S. swine and human strains compared to other HEV strains worldwide (id.). In addition to pigs, a strain of HEV was reportedly identified from tissue and fecal samples of wild-trapped rodents from Kathmandu Valley, Nepal (S. A. Tsarev et al., "Naturally acquired hepatitis E virus (HEV) infection in Nepalese rodents," Am. J. Trop. Med. Hyg. 59:242 (1998)). Sequence analyses revealed that the HEV sequence recovered from Nepalese rodents is most closely related to the HEV isolates from patients in Nepal (id.).

Hepatitis-splenomegaly syndrome (hereinafter referred to as "HS syndrome") is an emerging disease in chickens in North America. HS syndrome in chickens was first described in 1991 in western Canada, and the disease has since been recognized in eastern Canada and the U.S. HS syndrome is characterized by increased mortality in broiler breeder hens and laying hens of 30-72 weeks of age. The highest incidence usually occurs in birds between 40 to 50 weeks of age, and the weekly mortality rate can exceed 1%. Prior to sudden death, diseased chickens usually are clinically normal, with pale combs and wattles although some birds are in poor condition. In some outbreaks, up to 20% drop in egg production was observed. Affected chickens usually show regressive ovaries, red fluid in the abdomen, and enlarged liver and spleen. The enlarged livers are mottled and stippled with red, yellow and tan foci. Similar to the microscopic lesions found in the livers of humans infected with HEV, microscopic lesions in the livers of chickens with HS syndrome vary from multifocal to extensive hepatic necrosis and hemorrhage, with infiltration of mononuclear cells around portal triads. Microscopic lesions in the spleen include lymphoid depletion and accumulation of eosinophilic materials. Numerous other names have been used to describe the disease such as necrotic hemorrhage hepatitis-splenomegaly syndrome, chronic fulminating cholangiohepatitis, necrotic hemorrhagic hepatomegalic hepatitis and hepatitis-liver hemorrhage syndrome.

The cause of HS syndrome is not known. A viral etiology for HS syndrome has been suspected but attempts to propagate the virus in cell culture or embryonated eggs were unsuccessful (J. S. Jeffrey et al., "Investigation of hemorrhagic hepatosplenomegaly syndrome in broiler breeder hens," Proc. Western Poult. Dis. Conf., p. 46-48, Sacramento, Calif. (1998); H. L. Shivaprasad et al., "Necrohemorrhagic hepatitis in broiler breeders," Proc. Western Poult. Dis. Conf., p. 6, Sacramento, Calif. (1995)). The pathological lesions of HS in chickens, characterized by hepatic necrosis and hemorrhage, are somewhat similar to those observed in humans infected with HEV (R. H. Purcell, "Hepatitis E virus," FIELDS VIROLOGY, Vol. 2, pp. 2831-2843, B. N. Fields et al. eds, Lippincott-Raven Publishers, Philadelphia (3d ed. 1996); C. Riddell, "Hepatitis-splenomegaly syndrome," DISEASE OF POULTRY, p. 1041 (1997)). Since anti-HEV was detected in 44% of chickens in Vietnam (N. T. Tien et al., "Detection of immunoglobulin G to the hepatitis E virus among several animal species in Vietnam," Am. J. Trop. Med. Hyg. 57:211 (1997)), suggesting that chickens have been infected by HEV (or a related agent), it would be advantageous to find a link between HEV infection and HS syndrome in chickens. The link would permit the development of diagnostic assays and vaccines to protect against both human and chicken HEV infections thereby providing substantial public health and veterinary benefits. These goals and other desirable objectives are met by the isolation, genetic identification and characterization of the novel avian hepatitis E virus as described herein.

BRIEF SUMMARY OF THE INVENTION

The present invention concerns a novel avian hepatitis E virus, immunogenic compositions, vaccines which protect avian and mammalian species from viral infection or hepatitis-splenomegaly syndrome and methods of administering the vaccines to the avian and mammalian species to protect against viral infection or hepatitis-splenomegaly syndrome. The invention encompasses vaccines which are based on avian hepatitis E virus to protect against human hepatitis E. This invention includes methods for propagating, inactivating or attenuating hepatitis E viruses which uniquely utilize the inoculation of the live, pathogenic virus in embryonated chicken eggs. Other aspects of the present invention involve diagnostic reagents and methods for detecting the viral causative agent and diagnosing hepatitis E in a mammal or hepatitis-splenomegaly syndrome in an avian species which employ the nucleotide sequence described herein, antibodies raised or produced against the immunogenic compositions or antigens (such as ORF2, ORF3, etc.) expressed in a baculovirus vector, E. coli and the like. The invention further embraces methods for detecting avian HEV nucleic acid sequences in an avian or mammalian species using nucleic acid hybridization probes or oligonucleotide primers for polymerase chain reaction (PCR).

BRIEF DESCRIPTION OF THE DRAWINGS

The background of the invention and its departure from the art will be further described hereinbelow with reference to the accompanying drawings, wherein:

FIGS. 2A and 2B represent the amino acid sequence alignment of the putative RNA-dependent RNA polymerase (RdRp) gene of avian HEV (which corresponds to SEQ ID NO:4) with that of known HEV strains. The conserved GDD motif is underlined. The sequence of the prototype Burmese strain is shown on top, and only differences are indicated. Deletions are indicated by hyphens (-).

FIGS. 3A-3C represent the sequence alignment of the ORFs 1, 2 and 3 overlapping region. The sequence of the prototype Burmese strain is shown on top, and only differences are indicated in other HEV strains. The sequence of avian HEV (which corresponds to SEQ ID NO:12) is shown at the bottom. The start codons are indicated by arrows, and the stop codons are indicated by three asterisks (***). The two PCR primers (FdelAHEV and RdelAHEV) used to amplify the region flanking the deletions are indicated. Deletions are indicated by hyphens (-).

FIGS. 5A-5C represent the amino acid sequence alignment of the putative capsid gene (ORF2) of avian HEV (which corresponds to SEQ ID NO:6) with that of known HEV strains. The putative signal peptide sequence is highlighted, and the predicted cleavage site is indicated by arrowheads. The N-linked glycosylation sites are underlined in boldface. The sequence of the prototype Burmese strain is shown on top, and only differences are indicated in other HEV strains. The conserved tetrapeptide APLT is indicated (asterisks). Deletions are indicated by hyphens (-).

FIG. 6 illustrates the sequence alignments of the 3' non-coding region (NCR) of avian HEV (which corresponds to SEQ ID NO:13) with that of known HEV strains. The 3' NCR of avian HEV is shown on top, and only differences are indicated in other HEV strains. Deletions are indicated by hyphens (-).

FIGS. 8A-8C provide phylogenetic trees based on the sequences of different genomic regions of HEV wherein FIG. 8A is a 439 bp sequence of the helicase gene, FIG. 8B is a 196 bp sequence of the RNA-dependent RNA polymerase gene and FIG. 8C is a 148 bp sequence of the ORF2 gene. The sequences in the three selected regions are available for most HEV strains.

FIGS. 9A-9C represent the entire 4 kb nucleotide sequence (3931 bp plus poly(a) tract at 3' end) of the avian hepatitis E virus (which corresponds to SEQ ID NO:1).

FIG. 10 represents the predicted amino acid sequence of the protein encoded by the helicase gene (which corresponds to SEQ ID NO:2).

FIG. 11 represents the nucleotide sequence (439 bp) of the helicase gene (which corresponds to SEQ ID NO:3).

FIG. 12 represents the predicted amino acid sequence of the protein encoded by the RdRp gene (which corresponds to SEQ ID NO:4).

FIG. 13 represents the nucleotide sequence (1450 bp) of the RdRp gene (which corresponds to SEQ ID NO:5)

FIG. 14 represents the predicted amino acid sequence of the protein encoded by the ORF2 gene (which corresponds to SEQ ID NO:6).

FIG. 15 represents the nucleotide sequence (1821 bp) of the ORF2 gene (which corresponds to SEQ ID NO:7).

FIG. 16 represents the predicted amino acid sequence of the protein encoded by the ORF3 gene (which corresponds to SEQ ID NO:8).

FIG. 17 represents the nucleotide sequence (264 bp) of the ORF3 gene (which corresponds to SEQ ID NO:9).

FIG. 18A (left panel) is a photograph of a normal liver from a uninoculated control SPF layer chicken. FIG. 18B (right panel) is a photograph showing hepatomegaly and subcapsular hemorrhage of a liver from a SPF layer chicken experimentally infected with avian HEV. Note subcapsular hemorrhage and pronounced enlargement of right liver lobe. Liver margins are blunted indicating swelling.

FIG. 20 illustrates a phylogenetic tree based on the helicase gene region of 9 avian HEV isolates and other selected strains of human and swine HEVs. The avian HEV isolates (shown in boldface) are all clustered with the prototype avian HEV isolate (avian HEV USA).

FIG. 21A represents the expression of the C-terminal 268 amino acid sequence of truncated ORF2 capsid protein of avian HEV: Lanes 1-6, SDS-PAGE analysis of bacterial lysates at time points 0, 1, 2, 3, 4 and 6 hours after induction with IPTG; Lane 7, soluble proteins in the supernatant part of cell lysate; Lane 8, insoluble proteins after solubilization in SDS; Lane 9, SDS-PAGE analysis of 5 μg of the purified fusion protein. FIG. 21B (lower panel) represents the Western blot analyses of the bacterial cell lysates at time points 0 and 3 hours after IPTG induction (Lanes 1 and 2, respectively) and of the purified protein (Lane 3) using monoclonal antibody (MAb) against Xpress™ epitope (Invitrogen Corporation, Carlsbad, Calif.) located at the N-terminal of the expressed fusion protein. The product of about 32 kD is indicated by arrows.

FIG. 24 represents the alignment of the C-terminal 268 amino acid sequence of avian HEV with the corresponding regions of swine HEV, US2 and Sar-55 strains of human HEV. The sequence of avian HEV is shown on top. The deletions are indicated by minus (−) signs.

FIGS. 25A-25D show hydropathy and antigenicity plots of the truncated ORF2 proteins of avian HEV (FIG. 25A), swine HEV (FIG. 25B), Sar-55 strain of human HEV (FIG. 25C) and US2 strain of human HEV (FIG. 25D).

DETAILED DESCRIPTION OF THE INVENTION

Figure 1:
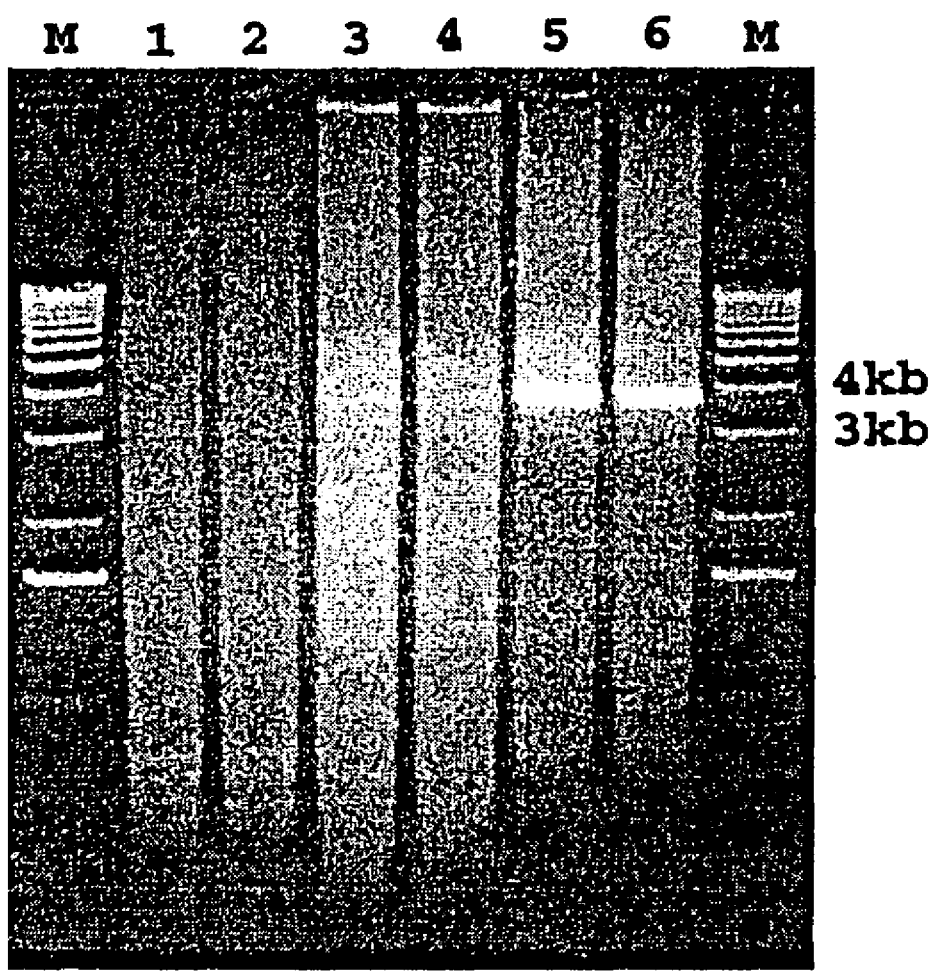
FIG. 1 shows the amplification of the 3' half of the avian HEV genome by RT-PCR: Lane M, 1 kb ladder; Lanes 1 and 2, PCR with ampliTaq gold polymerase; Lanes 3 and 4, PCR with ampliTaq gold polymerase in the presence of 5% v/v dimethyl sulfoxide (hereinafter referred to as "DMSO"); Lane 5 and 6, PCR amplification with a mixture of Taq polymerase and pfu containing in an eLONGase® Kit (GIBCO-BRL, Gaithersburg, Md.).

In accordance with the present invention, there is provided a novel avian hepatitis E virus (hereinafter referred to as "avian HEV"). The new animal strain of HEV, avian HEV, has been identified and genetically characterized from chickens with HS syndrome in the United States. Like swine HEV, the avian HEV identified in this invention is genetically related to human HEV strains. Unlike swine HEV that causes only subclinical infection and mild microscopic liver lesions in pigs, avian HEV is associated with a disease (HS syndrome) in chickens. Advantageously, therefore, avian HEV infection in chickens provides a superior, viable animal model to study human HEV replication and pathogenesis.

Electron microscopy examination of bile samples of chickens with HS syndrome revealed virus-like particles. The virus was biologically amplified in embryonated chicken eggs, and a novel virus genetically related to human HEV was identified from bile samples. The 3' half of the viral genome of approximately 4 kb was amplified by reverse-transcription polymerase chain reaction (RT-PCR) and sequenced. Sequence analyses of this genomic region revealed that it contains the complete 3' noncoding region, the complete ORFs 2 and 3 genes, the complete RNA-dependent RNA polymerase (RdRp) gene and a partial helicase gene of the ORF1. The helicase gene is most conserved between avian HEV and other HEV strains, displaying 58 to 60% amino acid sequence identities.

By comparing the ORF2 sequence of avian HEV with that of known HEV strains, a major deletion of 54 amino acid residues between the putative signal peptide sequence and the conserved tetrapeptide APLT of ORF2 was identified in the avian HEV. As described herein, phylogenetic analysis indicated that avian HEV is related to known HEV strains such as the well-characterized human and swine HEV. Conserved regions of amino acid sequences exist among the ORF2 capsid proteins of avian HEV, swine HEV and human HEV. The close genetic-relatedness of avian HEV with human and swine strains of HEV suggests avian, swine and human HEV all belong to the same virus family. The avian HEV of the present invention is the most divergent strain of HEV identified thus far. This discovery has important implications for HEV animal model, nomenclature and epidemiology, and for vaccine development against chicken HS, swine hepatitis E and human hepatitis E.

Schlauder et al. recently reported that at least 8 different genotypes of HEV exist worldwide (G. G. Schlauder et al., "Identification of 2 novel isolates of hepatitis E virus in Argentina," J. Infect. Dis. 182:294-297 (2000)). They found that the European strains (Greek 1, Greek 2, and Italy) and two Argentine isolates represent distinct genotypes. However, it is now found that the European strains (Greek 1, Greek 2 and Italy) appear to be more related to HEV genotype 3 which consists of swine and human HEV strains from the U.S. and a swine HEV strain from New Zealand. The phylogenetic tree was based on only 148 bp sequence that is available for these strains. Additional sequence information from these strains of human HEV is required for a definitive phylogenetic analysis. HEV was classified in the family Caliciviridae (R. H. Purcell, "Hepatitis E virus," FIELDS VIROLOGY, Vol. 2, pp. 2831-2843, B. N. Fields et al. eds, Lippincott-Raven Publishers, Philadelphia (3d ed. 1996)). The lack of common features between HEV and caliciviruses has led to the recent removal of HEV from the Caliciviridae family, and HEV remains unclassified.

Avian HEV represents a new genotype 5. Sequence analyses revealed that the new avian HEV is genetically related to swine and human HEV, displaying 47% to 50% amino acid sequence identity in the RdRp gene, 58% to 60% identity in the helicase gene, and 42% to 44% identity in the putative capsid gene (ORF2) with the corresponding regions of known HEV strains. The genomic organization of avian HEV is very similar to that of human HEV: non-structural genes such as RdRp and helicase are located at the 5' end and structural genes (ORF2 and ORF3) are located at the 3' end of the genome. The putative capsid gene (ORF2) of avian HEV is relatively conserved at its N-terminal region (excluding the signal peptide) but is less conserved at its C-terminal region. The ORF3 gene of avian HEV is very divergent compared to that of known HEV strains. However, the C-terminus of the ORF3 of avian HEV is relatively conserved, and this region is believed to be the immuno-dominant portion of the ORF3 protein (M. Zafrullah et al., "Mutational analysis of glycosylation, membrane translocation, and cell surface expression of the hepatitis E virus ORF2 protein," J. Virol. 73:4074-4082 (1999)). Unlike most known HEV strains, the ORF3 of avian HEV does not overlap with the ORF1. The ORF3 start codon of avian HEV is located 41 nucleotides downstream that of known HEV strains. Similar to avian HEV, the ORF3 of a strain of human HEV (HEV-T1 strain) recently identified from a patient in China does not overlap with ORF1, and its ORF3 start codon is located 28 nucleotides downstream the ORF1 stop codon (Y. Wang et al., "The complete sequence of hepatitis E virus genotype 4 reveals an alternative strategy for translation of open reading frames 2 and 3," J. Gen. Virol. 81:1675-1686 (2000)).

A major deletion was identified in the ORFs 2 and 3 overlapping region of the avian HEV genome, located between the ORF2 signal peptide and the conserved tetrapeptide APLT. It has been shown that, for certain HEV strains, this genomic region is difficult to amplify by conventional PCR methods (S. Yin et al., "A new Chinese isolate of hepatitis E virus: comparison with strains recovered from different geographical regions," Virus Genes 9:23-32 (1994)), and that an addition of 5% v/v of formamide or DMSO in the PCR reaction results in the successful amplification of this genomic region. The region flanking the deletion in avian HEV genome is relatively easy to amplify by a conventional PCR modified by the method of the present invention. To rule out potential RT-PCR artifacts, the region flanking the deletion was amplified with a set of avian HEV-specific primers flanking the deletion. RT-PCR was performed with various different parameters and conditions including cDNA synthesis at 60° C., PCR amplification with higher denaturation temperature and shorter annealing time, and PCR with the addition of 5% v/v of formamide or DMSO. No additional sequence was identified, and the deletion was further verified by direct sequencing of the amplified PCR product flanking the deletion region. It is thus concluded that the observed deletion in avian HEV genome is not due to RT-PCR artifacts.

Ray et al. also reported a major deletion in the ORF2/ORF3 overlapping region of an Indian strain of human HEV (R. Ray et al., "Indian hepatitis E virus shows a major deletion in the small open reading frame," Virology 189:359-362 (1992)). Unlike the avian HEV deletion, the deletion in the Indian strain of human HEV eliminated the ORF2 signal peptide sequence that overlaps with the ORF3. The sequence of other genomic regions of this Indian HEV strain is not available for further analysis. The biological significance of this deletion is not known. It has been shown that, when the ORF2 of a human HEV is expressed in the baculovirus system, a truncated version of ORF2 protein lacking the N-terminal 111 amino acid residues is produced. The truncated ORF2 protein was cleaved at amino acid position 111-112 (Y. Zhang et al., "Expression, characterization, and immunoreactivities of a soluble hepatitis E virus putative capsid protein species expressed in insect cells," Clin. Diag. Lab. Immunol. 4:423-428 (1997)), but was still able to form virus-like particles (T. C. Li et al., "Expression and self-assembly of empty virus-like particles of hepatitis E virus," J. Virol. 71:7207-7213 (1997)). Avian HEV lacks most of the N-terminal 100 amino acid residues of the ORF2, however, the conserved tetrapeptide APLT (pos. 108-111 in ORF2) and a distinct but typical signal peptide sequence are present in the ORF2 of avian HEV. Taken together, these data suggest that the genomic region between the cleavage site of the ORF2 signal peptide and the conserved tetrapeptide APLT is dispensable, and is not required for virus replication or maturation.

It has been shown that the ORF2 protein of human HEV pORF2 is the main immunogenic protein that is able to induce immune response against HEV. Recently, the C-terminal 267 amino acids of truncated ORF2 of a human HEV was expressed in a bacterial expression system showing that the sequences spanning amino acids 394 to 457 of the ORF2 capsid protein participated in the formation of strongly immunodominant epitopes on the surface of HEV particles (M. A. Riddell et al., "Identification of immunodominant and conformational epitopes in the capsid protein of hepatitis E virus by using monoclonal antibodies," J. Virology 74:8011-17 (2000)). It was reported that this truncated protein was used in an ELISA to detect HEV infection in humans (D. A. Anderson et al., "ELISA for IgG-class antibody to hepatitis E virus based on a highly conserved, conformational epitope expressed in *Escherichia coli*," J. Virol. Methods 81:131-42 (1999)). It has also been shown that C-terminus of the protein is masked when expression of the entire pORF2 is carried out in a bacterial expression system, and that the 112 amino acids located at N-terminus of ORF2 and the 50 amino acids located at the C-terminus are not involved in the formation of virus-like particles (T. C. Li et al., 1997, supra). The expression and characterization of the C-terminal 268 amino acid residues of avian HEV ORF2 in the context of the present invention corresponds to the C-terminal 267 amino acid residues of human HEV.

The present invention demonstrates that avian HEV is antigenically related to human and swine HEVs as well as chicken BLSV. The antigenic relatedness of avian HEV ORF2 capsid protein with human HEV, swine HEV and chicken BLSV establishes that immunization with an avian HEV vaccine (either an attenuated or a recombinant vaccine) will protect not only against avian HEV infection, HS syndrome and BLSV infection in chickens but also against human and swine HEV infections in humans and swine. Thus, a vaccine based on avian HEV, its nucleic acid and the proteins encoded by the nucleic acid will possess beneficial, broad spectrum, immunogenic activity against avian, swine and human HEVs, and BLSV.

Western blot analyses revealed that antiserum to each virus strongly reacted with homologous antigen. It was also demonstrated that the antiserum against BLSV reacted with the recombinant ORF2 protein of avian HEV, indicating that BLSV is antigenically related to avian HEV. The reaction between Sar-55 human HEV and swine HEV antigens with convalescent antiserum against avian HEV generated strong signals while the cross-reactivity of antisera with heterologous antigens was relatively weak. In ELISA, the optical densities ("ODs") obtained from the reaction of avian HEV antigen with Sar-55 HEV and swine HEV antisera were lower than the ODs obtained from the reaction of avian HEV antiserum with the HPLC-purified Sar-55 HEV and swine HEV antigens. This result may have occurred because the Sar-55 HEV and swine HEV antigens of the examples were the complete ORF2 proteins instead of the truncated avian ORF2 protein lacking the N-terminal amino acid residues.

Schofield et al. generated neutralizing MAbs against the capsid protein of a human HEV (D. J. Schofield et al., "Identification by phage display and characterization of two neutralizing chimpanzee monoclonal antibodies to the hepatitis E virus capsid protein," J. Virol. 74:5548-55 (2000)). The neutralizing MAbs recognized the linear epitope(s) located between amino acids 578 and 607. The region in avian REV corresponding to this neutralizing epitope is located within the truncated ORF2 of avian HEV that reacted with human HEV and swine HEV anti-sera.

So far, HS syndrome has only been reported in several Provinces of Canada and a few States in the U.S. In Australia, chicken farms have been experiencing outbreaks of big liver and spleen disease (BLS) for many years. BLS was recognized in Australia in 1988 (J. H. Handlinger et al., "An egg drop associated with splenomegaly in broiler breeders," Avian Dis. 32:773-778 (1988)), however, there has been no report regarding a possible link between HS in North America and BLS in Australia. A virus (designated BLSV) was isolated from chickens with BLS in Australia. BLSV was shown to be genetically related to HEV based on a short stretch of sequence available (C. J. Payne et al., "Sequence data suggests big liver and spleen disease virus (BLSV) is genetically related to hepatitis E virus," Vet. Microbiol. 68:119-25 (1999)). The avian HEV identified in this invention is closely related to BLSV identified from chickens in Australia, displaying about 80% nucleotide sequence identity in this short genomic region (439 bp). It appears that a similar virus related to HEV may have caused the HS syndrome in North American chickens and BLS in Australian chickens, but the avian HEV nevertheless remains a unique strain or isolate, a totally distinct entity from the BLS virus. Further genetic characterization of avian HEV shows that it has about 60% nucleotide sequence identities with human and swine HEVs.

In the past, the pathogenesis and replication of HEV have been poorly understood due to the absence of an efficient in vitro cell culture system for HEV. In this invention, it is now demonstrated that embryonated SPF chicken eggs can unexpectedly be infected with avian HEV through intravenous route (I.V.) of inoculation. Earlier studies showed that bile samples positive by EM for virus particles failed to infect embryonated chicken eggs (J. S. Jeffrey et al., 1998, supra; H. L. Shivaprasad et al., 1995, supra). The I.V. route of inoculation has been almost exclusively used in studies with human and swine HEV. Other inoculation routes such as the oral route have failed to infect pigs with swine HEV, even when a relatively high infectious dose ($10^{4.5}$ 50% pig infectious dose) of swine HEV was used. Based on the surprising success of the present egg inoculation experiments, it illustrates that embryonated eggs are susceptible to infection with human and avian strains of HEV making embryonated eggs a useful in vitro method to study HEV replication and a useful tool to manufacture vaccines that benefit public health.

The identification of avian HEV from chickens with HS in the context of this invention further strengthens the hypothesis that hepatitis E is a zoonosis. The genetic close-relatedness of avian HEV to human and swine HEV strains raises a potential public health concern for zoonosis. Recent studies showed that pig handlers are at increased risk of zoonotic HEV infection (X. J. Meng et al., 1999, supra). Karetnyi et al. reported that human populations with occupational exposure to wild animals have increased risks of HEV infection (Y. V. Karetnyi et al, "Hepatitis E virus infection prevalence among selected populations in Iowa," J. Clin. Virol. 14:51-55 (1999)). Since individuals such as poultry farmers or avian veterinarians may be at potential risk of zoonotic infection by avian HEV, the present invention finds broad application to prevent viral infections in humans as well as chickens and other carrier animals.

The present invention provides an isolated avian hepatitis E virus that is associated with serious viral infections and hepatitis-splenomegaly syndrome in chickens. This invention includes, but is not limited to, the virus which has a nucleotide sequence set forth in SEQ ID NO:1, its functional equivalent or complementary strand. It will be understood that the specific nucleotide sequence derived from any avian HEV will have slight variations that exist naturally between individual viruses. These variations in sequences may be seen in deletions, substitutions, insertions and the like. Thus, to distinguish the virus embraced by this invention from the Australian big liver and spleen disease virus, the avian HEV virus is characterized by having no more than about 80% nucleotide sequence homology to the BLSV.

The source of the isolated virus strain is bile, feces, serum, plasma or liver cells from chickens or human carriers suspected to have the avian hepatitis E viral infection. However, it is contemplated that recombinant DNA technology can be used to duplicate and chemically synthesize the nucleotide sequence. Therefore, the scope of the present invention encompasses the isolated polynucleotide which comprises, but is not limited to, a nucleotide sequence set forth in SEQ ID NO:1 or its complementary strand; a polynucleotide which hybridizes to and which is at least 95% complementary to the nucleotide sequence set forth in SEQ ID NO:1; or an immunogenic fragment selected from the group consisting of a nucleotide sequence in the partial helicase gene of ORF1 set forth in SEQ ID NO:3, a nucleotide sequence in the RdRp gene set forth in SEQ ID NO:5, a nucleotide sequence in the ORF2 gene set forth in SEQ ID NO:7, a nucleotide sequence in the ORF3 gene set forth in SEQ ID NO:9 or their complementary strands. The immunogenic or antigenic coding regions or fragments can be determined by techniques known in the art and then used to make monoclonal or polyclonal antibodies for immunoreactivity screening or other diagnostic purposes. The invention further encompasses the purified, immunogenic protein encoded by the isolated polynucleotides. Desirably, the protein may be an isolated or recombinant ORF2 capsid protein or an ORF3 protein.

Another important aspect of the present invention is the unique immunogenic composition comprising the isolated avian HEV or an antigenic protein encoded by an isolated polynucleotide described hereinabove and its use for raising or producing antibodies. The composition contains a non-toxic, physiologically acceptable carrier and, optionally, one or more adjuvants. Suitable carriers, such as, for example, water, saline, ethanol, ethylene glycol, glycerol, etc., are easily selected from conventional excipients and co-formulants may be added. Routine tests can be performed to ensure physical compatibility and stability of the final composition.

Vaccines and methods of using them are also included within the scope of the present invention. Inoculated avian or mammalian species are protected from serious viral infection, hepatitis-splenomegaly syndrome, hepatitis E and other related illness. The vaccines comprise, for example, an inactivated or attenuated avian hepatitis E virus, a nontoxic, physiologically acceptable carrier and, optionally, one or more adjuvants.

The adjuvant, which may be administered in conjunction with the immunogenic composition or vaccine of the present invention, is a substance that increases the immunological response when combined with the composition or vaccine. The adjuvant may be administered at the same time and at the same site as the composition or vaccine, or at a different time, for example, as a booster. Adjuvants also may advantageously be administered to the mammal in a manner or at a site different from the manner or site in which the composition or vaccine is administered. Suitable adjuvants include, but are not limited to, aluminum hydroxide (alum), immunostimulating complexes (ISCOMS), non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The new vaccines of this invention are not restricted to any particular type or method of preparation. The vaccines include, but are not limited to, modified live vaccines, inactivated vaccines, subunit vaccines, attenuated vaccines, genetically engineered vaccines, etc. These vaccines are prepared by general methods known in the art modified by the new use of embryonated eggs. For instance, a modified live vaccine may be prepared by optimizing avian HEV propagation in embryonated eggs as described herein and further virus production by methods known in the art. Since avian HEV cannot grow in the standard cell culture, the avian HEV of the present invention can uniquely be attenuated by serial passage in embryonated chicken eggs. The virus propagated in eggs may be lyophilized (freeze-dried) by methods known in the art to enhance preservability for storage. After subsequent rehydration, the material is then used as a live vaccine.

The advantages of live vaccines is that all possible immune responses are activated in the recipient of the vaccine, including systemic, local, humoral and cell-mediated immune responses. The disadvantages of live virus vaccines, which may outweigh the advantages, lie in the potential for contamination with live adventitious viral agents or the risk that the virus may revert to virulence in the field.

To prepare inactivated virus vaccines, for instance, the virus propagation and virus production in embryonated eggs are again first optimized by methods described herein. Serial virus inactivation is then optimized by protocols generally known to those of ordinary skill in the art or, preferably, by the methods described herein.

Inactivated virus vaccines may be prepared by treating the avian HEV with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

The preparation of subunit vaccines typically differs from the preparation of a modified live vaccine or an inactivated vaccine. Prior to preparation of a subunit vaccine, the protective or antigenic components of the vaccine must be identified. Such protective or antigenic components include certain amino acid segments or fragments of the viral capsid proteins which raise a particularly strong protective or immunological response in chickens; single or multiple viral capsid proteins themselves, oligomers thereof, and higher-order associations of the viral capsid proteins which form virus substructures or identifiable parts or units of such substructures; oligoglycosides, glycolipids or glycoproteins present on or near the surface of the virus or in viral substructures such as the lipoproteins or lipid groups associated with the virus, etc. Preferably, the capsid protein (ORF2) is employed as the antigenic component of the subunit vaccine. Other proteins may also be used such as those encoded by the nucleotide sequence in the ORF3 gene. These immunogenic components are readily identified by methods known in the art. Once identified, the protective or antigenic portions of the virus (i.e., the "subunit") are subsequently purified and/or cloned by procedures known in the art. The subunit vaccine provides an advantage over other vaccines based on the live virus since the subunit, such as highly purified subunits of the virus, is less toxic than the whole virus.

If the subunit vaccine is produced through recombinant genetic techniques, expression of the cloned subunit such as the ORF2 (capsid) and ORF3 genes, for example, may be optimized by methods known to those in the art (see, for example, Maniatis et al., "Molecular Cloning: A Laboratory Manual," Cold Spring Harbor Laboratory, Cold Spring Harbor, Mass. (1989)). On the other hand, if the subunit being employed represents an intact structural feature of the virus, such as an entire capsid protein, the procedure for its isolation from the virus must then be optimized. In either case, after optimization of the inactivation protocol, the subunit purification protocol may be optimized prior to manufacture.

To prepare attenuated vaccines, the live, pathogenic virus is first attenuated (rendered nonpathogenic or harmless) by methods known in the art or, preferably, as described herein. For instance, attenuated viruses may be prepared by the technique of the present invention which involves the novel serial passage through embryonated chicken eggs. Attenuated viruses can be found in nature and may have naturally-occurring gene deletions or, alternatively, the pathogenic viruses can be attenuated by making gene deletions or producing gene mutations. The attenuated and inactivated virus vaccines comprise the preferred vaccines of the present invention.

Genetically engineered vaccines, which are also desirable in the present invention, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as feces or bile by methods known in the art, preferably by the method taught herein using embryonated chicken eggs as hosts. The RNA is extracted from the biologically pure virus or infectious agent by methods known in the art, preferably by the guanidine isothiocyanate method using a commercially available RNA isolation kit (for example, the kit available from Statagene, La Jolla, Calif.) and purified by methods known in the art, preferably by ultracentrifugation in a CsCl gradient. RNA may be further purified or enriched by oligo (dT)-cellulose column chromatography. The cDNA of viral genome is cloned into a suitable host by methods known in the art (see Maniatis et al., id.), and the virus genome is then analyzed to determine essential regions of the genome for producing antigenic portions of the virus. Thereafter, the procedure is generally the same as that for the modified live vaccine, an inactivated vaccine or a subunit vaccine.

Genetically engineered vaccines based on recombinant DNA technology are made, for instance, by identifying the portion of the viral gene which encodes for proteins responsible for inducing a stronger immune or protective response in chickens (e.g., proteins derived from ORF1, ORF2, ORF3, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co. (1992)). The host cells are cultured, thus expressing the desired vaccine proteins, which can be purified to the desired extent and formulated into a suitable vaccine product.

Genetically engineered proteins, useful in vaccines, for instance, may be expressed in insect cells, yeast cells or mammalian cells. The genetically engineered proteins, which may be purified or isolated by conventional methods, can be directly inoculated into an avian or mammalian species to confer protection against avian or human hepatitis E.

An insect cell line (like HI-FIVE) can be transformed with a transfer vector containing polynucleic acids obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, RNA or DNA from the HS infected carrier or the isolated avian HEV which encode one or more capsid proteins can be inserted into live vectors, such as a poxvirus or an adenovirus and used as a vaccine.

An immunologically effective amount of the vaccine of the present invention is administered to an avian or mammalian species in need of protection against said infection or syndrome. The "immunologically effective amount" can be easily determined or readily titrated by routine testing. An effective amount is one in which a sufficient immunological response to the vaccine is attained to protect the bird or mammal exposed to the virus which causes chicken HS, human hepatitis E, swine hepatitis E or related illness. Preferably, the avian or mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable dosages of active antigenic agent based on the weight of the bird or mammal, concentration of the antigen and other typical factors.

The vaccine can be administered to chickens, turkeys or other farm animals in close contact with chickens, for example, pigs. Also, the vaccine can be given to humans such as chicken or poultry farmers who are at high risk of being infected by the viral agent. It is contemplated that a vaccine based on the avian HEV can be designed to provide broad protection against both avian and human hepatitis E. In other words, the vaccine based on the avian HEV can be preferentially designed to protect against human hepatitis E through the so-called "Jennerian approach" (i.e., cowpox virus vaccine can be used against human smallpox by Edward Jenner). Desirably, the vaccine is administered directly to an avian or mammalian species not yet exposed to the virus which causes HS, hepatitis E or related illness. The vaccine can conveniently be administered orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

Also included within the scope of the present invention is a novel method for propagating, inactivating or attenuating the pathogenic hepatitis E virus (avian, swine, human, etc.) which comprises inoculating an embryonated chicken egg with a live, pathogenic hepatitis E virus contained in a biological sample from bile, feces, serum, plasma, liver cell, etc., preferably by intravenous injection, and either recovering a live, pathogenic virus for further research and vaccine development or continuing to pass the pathogenic virus serially through additional embryonated chicken eggs until the pathogenic virus is rendered inactivated or attenuated. Propagating live viruses through embryonated chicken eggs according to the present invention is a unique method which others have failed to attain. Vaccines are typically made by serial passage through cell cultures but avian HEV, for example, cannot be propagated in conventional cell cultures. Using embryonated chicken eggs provides a novel, viable means for inactivating or attenuating the pathogenic virus in order to be able to make a vaccine product. The inactivated or attenuated strain, which was previously unobtainable, can now be incorporated into conventional vehicles for delivering vaccines.

Additionally, the present invention provides a useful diagnostic reagent for detecting the avian or mammalian HEV infection or diagnosing hepatitis-splenomegaly syndrome in an avian or mammalian species which comprise a monoclonal or polyclonal antibody purified from a natural host such as, for example, by inoculating a chicken with the avian HEV or the immunogenic composition of the invention in an effective immunogenic quantity to produce a viral infection and recovering the antibody from the serum of the infected chicken. Alternatively, the antibodies can be raised in experimental animals against the natural or synthetic polypeptides derived or expressed from the amino acid sequences or immunogenic fragments encoded by the nucleotide sequence of the isolated avian HEV. For example, monoclonal antibodies can be produced from hybridoma cells which are obtained from mice such as, for example, Balb/c, immunized with a polypeptide antigen derived from the nucleotide sequence of the isolated avian HEV. Selection of the hybridoma cells is made by growth in hyproxanthine, thymidine and aminopterin in a standard cell culture medium like Dulbecco's modified Eagle's medium (DMEM) or minimal essential medium. The hybridoma cells which produce antibodies can be cloned according to procedures known in the art. Then, the discrete colonies which are formed can be transferred into separate wells of culture plates for cultivation in a suitable culture medium. Identification of antibody secreting cells is done by conventional screening methods with the appropriate antigen or immunogen. Cultivating the hybridoma cells in vitro or in vivo by obtaining ascites fluid in mice after injecting the hybridoma produces the desired monoclonal antibody via well-known techniques.

For another alternative method, avian HEV capsid protein can be expressed in a baculovirus expression system or *E. coli* according to procedures known in the art. The expressed recombinant avian HEV capsid protein can be used as the antigen for diagnosis of HS or human hepatitis E in an enzyme-linked immunoabsorbent Assay (ELISA). The ELISA assay based on the avian recombinant capsid antigen, for example, can be used to detect antibodies to avian HEV in avian and mammalian species. Although the ELISA assay is preferred, other known diagnostic tests can be employed such as immunofluorescence assay (IFA), immunoperoxidase assay (IPA), etc.

Desirably, a commercial ELISA diagnostic assay in accordance with the present invention can be used to diagnose avian HEV infection and HS syndrome in chickens. The examples illustrate using purified ORF2 protein of avian HEV to develop an ELISA assay to detect anti-HEV in chickens. Weekly sera collected from SPF chickens experimentally infected with avian HEV, and negative sera from control chickens are used to validate the assay. This ELISA assay has been successfully used in the chicken studies to monitor the course of seroconversion to anti-HEV in chickens experimentally infected with avian HEV. Further standardization of the test by techniques known to those skilled in the art may optimize the commercialization of a diagnostic assay for avian HEV. Other diagnostic assays can also be developed as a result of the findings of the present invention such as a nucleic acid-based diagnostic assay, for example, an RT-PCR assay and the like. Based on the description of the sequences of the partial genomes of the nine new strains of avian HEV, the RT-PCR assay and other nucleic acid-based assays can be standardized to detect avian HEV in clinical samples.

The antigenic cross-reactivity of the truncated ORF2 capsid protein (pORF2) of avian HEV with swine HEV, human HEV and the chicken big liver and spleen disease virus (BLSV) is shown in the below examples. The sequence of C-terminal 268 amino acid residuals of avian HEV ORF2 was cloned into expression vector pRSET-C and expressed in *Escherichia coli* (*E. coli*) strain BL21(DE3)pLysS. The truncated ORF2 protein was expressed as a fusion protein and purified by affinity chromatography. Western blot analysis revealed that the purified avian HEV ORF2 protein reacted with the antisera raised against the capsid protein of Sar-55 human HEV and with convalescent antisera against swine HEV and US2 human HEV as well as antiserum against BLSV. The antiserum against avian HEV also reacted with the HPLC-purified recombinant capsid proteins of swine HEV and Sar-55 human HEV. The antiserum against US2 strain of human HEV also reacted with recombinant ORF2 proteins of both swine HEV and Sar-55 human HEV. Using ELISA further confirmed the cross reactivity of avian HEV putative capsid protein with the corresponding genes of swine HEV and human HEVs. The results show that avian HEV shares some antigenic epitopes in its capsid protein with swine and human HEVs as well as BLSV, and establish the usefulness of the diagnostic reagents for HEV diagnosis as described herein.

The diagnostic reagent is employed in a method of the invention for detecting the avian or mammalian hepatitis E viral infection or diagnosing hepatitis-splenomegaly syndrome in an avian or mammalian species which comprises contacting a biological sample of the bird or mammal with the aforesaid diagnostic reagent and detecting the presence of an antigen-antibody complex by conventional means known to those of ordinary skill in the art. The biological sample includes, but is not limited to, blood, plasma, bile, feces, serum, liver cell, etc. To detect the antigen-antibody complex, a form of labeling is often used. Suitable radioactive or non-radioactive labeling substances include, but are not limited to, radioactive isotopes, fluorescent compounds, dyes, etc. The detection or diagnosis method of this invention includes immunoassays, immunometric assays and the like. The method employing the diagnostic reagent may also be accomplished in an in vitro assay in which the antigen-antibody complex is detected by observing a resulting precipitation. The biological sample can be utilized from any avian species such as chickens, turkeys, etc. or mammals such as pigs and other farm animals or humans, in particular, chicken farmers who have close contact with chickens. If the bird or the mammal is suspected of harboring a hepatitis E viral infection and exhibiting symptoms typical of hepatitis-splenomegaly syndrome or other related illness, the diagnostic assay will be helpful to determine the appropriate course of treatment once the viral causative agent has been identified.

Another preferred embodiment of the present invention involves methods for detecting avian HEV nucleic acid sequences in an avian or mammalian species using nucleic acid hybridization probes or oligonucleotide primers for polymerase chain reaction (PCR) to further aid in the diagnosis of viral infection or disease. The diagnostic tests, which are useful in detecting the presence or absence of the avian hepatitis E viral nucleic acid sequence in the avian or mammalian species, comprise, but are not limited to, isolating nucleic acid from the bird or mammal and then hybridizing the isolated nucleic acid with a suitable nucleic acid probe or probes, which can be radio-labeled, or a pair of oligonucleotide primers derived from the nucleotide sequence set forth in SEQ ID NO:1 and determining the presence or absence of a hybridized probe complex. Conventional nucleic acid hybridization assays can be employed by those of ordinary skill in this art. For example, the sample nucleic acid can be immobilized on paper, beads or plastic surfaces, with or without employing capture probes; an excess amount of radio-labeled probes that are complementary to the sequence of the sample nucleic acid is added; the mixture is hybridized under suitable standard or stringent conditions; the unhybridized probe or probes are removed; and then an analysis is made to detect the presence of the hybridized probe complex, that is, the probes which are bound to the immobilized sample. When the oligonucleotide primers are used, the isolated nucleic acid may be further amplified in a polymerase chain reaction or other comparable manner before analysis for the presence or absence of the hybridized probe complex. Preferably, the polymerase chain reaction is performed with the addition of 5% v/v of formamide or dimethyl sulfoxide.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples that follow below.

EXAMPLE 1

Biological Amplification of the Virus in Embryonated Chicken Eggs

A sample of bile collected from a chicken with HS in California was used in this study. Electron microscopy (EM) examination showed that this bile sample was positive for virus particles of 30 to 40 nm in diameter. The limited bile materials containing the virus prevented the performance of extensive genetic identification and characterization of the virus. A preliminary study was conducted to determine if the virus could be biologically amplified in embryonated chicken eggs. SPF eggs were purchased at one day of age (Charles River SPAFAS, Inc., North Franklin, Conn.) and incubated for 9 days in a 37° C. egg incubator. At 9 days of embryonated age, 6 eggs were inoculated intravenously with 100 μl of a $10^{-3}$ dilution and 6 eggs with a $10^{-4}$ dilution in phosphate buffered saline (PBS) of the positive bile sample. Six eggs were uninoculated as controls. The inoculated eggs were incubated at 37° C. until 21 days of age (before natural hatching), at which time the embryos were sacrificed. Bile and liver samples were collected and tested by RT-PCR for evidence of virus replication. The virus recovered from infected eggs was used as the virus source for further characterization.

EXAMPLE 2

Amplification of the 3' Half of the Viral Genome

Based on the assumption that the putative virus associated with HS in chickens shared nucleotide sequence similarity with human and swine HEV, a modified 3' RACE (Rapid Amplification of cDNA Ends) system was employed to amplify the 3'-half of the viral genome. Briefly, the sense primer, F4AHEV (Table 1 below), was chosen from a conserved region in ORF1 among known swine and human HEV strains including the big liver and spleen disease virus (BLSV) identified from chickens in Australia (C. J. Payne et al., "Sequence data suggests big liver and spleen disease virus (BLSV) is genetically related to hepatitis E virus," Vet. Microbiol. 68:119-25 (1999)). The antisence primers included two anchored commercial primers of nonviral origin (GIBCO-BRL, Gaithersburg, Md.): AUAP (Abridged Universal Amplification Primer) and AP (Adapter Primer) with a poly (T) stretch (Table 1, below). Total RNA was extracted from 100 μl of the bile by TriZol reagent (GIBCO-BRL), and resuspended in 11.5 μl of DNase-, RNase- and proteinase-free water (Eppendorf Scientific, Inc., now Brinkmann Instruments, Inc., Westbury, N.Y.). Total RNA was reverse-transcribed at 42° C. for 90 minutes in the presence of reverse transcription reaction mixtures consisting of 11.5 μl of the total RNA, 1 μl of Superscript II reverse transcriptase (GIBCO-BRL), 1 μl of 10 μM antisense primer, 0.5 μl of RNase inhibitor (GIBCO-BRL), 0.5 μl of dithioteritol, and 4 μl of 5×RT buffer.

PCR was performed with a mixture of a Taq DNA polymerase and a proofreading pfu polymerase contained in an eLONGase® Kit (GIBCO-BRL, Gaithersburg, Md.). The PCR reaction was carried out according to the instructions supplied with the kit and consisted of 10 μl of cDNA, 1.7 mM $MgCL_2$ and 10 μl of each 10 μM sense and antisense primers. Alternatively, AmpliTaq gold polymerase (Perkin-Elmer, Wellesley, Mass.) with and without 5% v/v dimethyl sulfoxide (DMSO) was used. The PCR reaction consisted of a denaturation at 94° C. for 1 minute, followed by 5 cycles of denaturation at 94° C. for 40 seconds, annealing at 42° C. for 40 seconds, extension at 68° C. for 5 minutes, 16 cycles of a touch down PCR with the starting annealing temperature at 59° C. which was reduced by 1 degree every 2 cycles, and then 11 cycles of amplification with an annealing temperature at 51° C., followed by a final extension at 74° C. for 10 minutes. The resulting PCR product was analyzed on a 0.8% w/v agarose gel. When AmpliTaq gold polymerase was used, the thermal cycle profile and parameters remained the same except that the enzyme was first activated by incubation at 95° C. for 9 minutes.

TABLE 1

Synthetic oligonucleotide primers used for PCR amplification and DNA sequencing of the avian HEV genome

| Primer Designation | Nucleotide Sequence (5' to 3') | position[a] |
|---|---|---|
| Sequencing Primers | CAATCTCGACCAGCACCCCACCAA (SEQ ID NO: 14) | 407-384 |
| | CCGGGAGCGCTGTAGTGTGATTGATGT | 358-384 |
| | ACAGGCCCGGGTGGATTTATGG (SEQ ID NO: 15) | 618-597 |
| | CAATCAACCCCTCAACACTGGA | 840-861 |
| | GTGCAACAGGGTCATCCAGCGTAAAT (SEQ ID NO: 16) | 1007-982 |
| | GGATGCCCGATTGGATGGTAGCCTT | 1275-1299 |
| | AAGGCTACCATCCAATCGGGCATCC (SEQ ID NO: 17) | 1299-1275 |
| | TCCCGGGAGCTGGTGTTGTCTGC | 1602-1624 |
| | GATGCCCGATTGGATGGTAGCCTTGTA | 1276-1302 |
| | ATGTCGGGCCCCCAGTTCTTGTCAG (SEQ ID NO: 18) | 1677-1653 |
| | CAATGTGCTGCGGGGTGTCAAG | 2015-2036 |
| | CCCTTGACACCCCGCAGCACATT (SEQ ID NO: 19) | 2038-2016 |
| | TATAGAGAAGCCGCCCACCGCATTTG (SEQ ID NO: 20) | 2439-2414 |
| | GACCAATTTCGCCATCCTCAGCAGT (SEQ ID NO: 21) | 2914-2890 |
| | ACCGACATATACAGTTTCACCTCAG (SEQ ID NO: 22) | 3065-3041 |
| | CTGAGGTGAAACTGTATATGTCGGT | 3041-3065 |
| | GAACGGCGAGCCTGAGGTGAAACTGT | 3030-3055 |
| | CAATAGGCCATGCTTATAGAGAA (SEQ ID NO: 23) | 2453-2431 |
| | GCATACCAAACCACGGAGCTACCATTCTG (SEQ ID NO: 24) | 3572-3544 |
| | TCTTCAGAATGGTAGCTCCGTGGTTTG | 3540-3566 |
| F4AHEV | GCTAGGCGACCCGCACCAGAT | non-viral (GIBCO) |
| AP | GACTCGAGTCGACATCGA(T)$_{17}$ | non-viral (GIBCO) |
| PAUP | GACTCGAGTCGACATCGA | non-viral (GIBCO) |
| FdelAHEV | GGGGCCCGACATTCAGCGGATGCAG | 1666-1690 |
| RdelAHEV | GCCGCGGTGACAACGTCTGTGAGAGG (SEQ ID NO: 25) | 2168-2143 |

[a]The positions are relative to the 3931 by sequence of avian HEV (corresponding to SEQ ID NO: 1) determined in the present invention.

EXAMPLE 3

Cloning of the Amplified PCR Product

A PCR product of approximately 4 kb was amplified by the modified 3' RACE system. The PCR product was excised and eluted from the agarose gel with the CoNcERT™ Rapid Gel Extraction System (GIBCO-BRL). The purified PCR product was subsequently cloned into a TA vector. The recombinant plasmid was used to transform competent cells supplied in the AdvanTAge™ PCR Cloning Kit (Clontech Laboratories, Inc., Palo Alta, Calif.) according to the manufacturer's instruction. White colonies were selected and grown in LB broth containing 100 µg/ml of ampicillin. The recombinant plasmids containing the insert were isolated with a Plasmid DNA Isolation kit (Qiagen Inc., Valencia, Calif.).

EXAMPLE 4

DNA Sequencing

Three independent cDNA clones containing the approximately 4 kb insert were selected and sequenced at Virginia Tech DNA Sequencing Facility with an Automated DNA Sequencer (Applied Biosystem, Inc., Foster City, Calif.). Primer walking strategy was employed to determine the nucleotide sequence of both DNA strands of the three independent cDNA clones. The M13 forward and reverse primers as well as sixteen avian HEV specific primers (Table 1, above) were used to determine the nucleotide sequence of the approximately 4 kb viral genome. To facilitate DNA sequencing, a unique EcoR I restriction site that is present in this 4 kb viral genomic fragment was utilized. The recombinant plasmid with the 4 kb insert was digested by the EcoR I restriction enzyme, and the resulting two EcoR I fragments were subcloned into pGEM-9zf (−) (Promega, Madison, Wis.). The cDNA subclones were also used to determine the sequence by primer walking strategy. The sequence at the 5' end of the fragment was further confirmed by direct sequencing of the PCR product amplified with avian HEV-specific primers.

EXAMPLE 5

Sequence and Phylogenetic Analyses

The complete sequence of the approximately 4 kb viral genomic fragment was assembled and analyzed with the MacVector® (Oxford Molecular, Inc., Madison, Wis.) and DNAstar (DNASTAR, Inc., Madison, Wis.) computer programs. For any given region, the consensus sequence was derived from at least three independent cDNA clones. The putative signal peptide of the ORF2 protein was predicted with the SignalP V1.1 program (http://www.cbs.dtu.dk/services/SignalP). The hydrophobicity analysis of the putative ORF2 protein was performed with the MacVector program using Sweet/Eisenberg method (R. M. Sweet et al., "Correlation of sequence hydrophobicities measures similarity in three-dimensional protein structure," J. Mol. Biol. 171:479-488 (1983)). Phylogenetic analyses were conducted with the aid of the PAUP program (David L. Swofford, Smithsonian Institution, Washington, D.C., and distributed by Sinauer Associates, Inc., Sunderland, Mass.).

For most HEV strains, the sequences are available only in certain genomic regions. Therefore, to better understand the phylogenetic relationship of known HEV strains, phylogenetic analyses were based on three different genomic regions: a 148 bp fragment of the ORF2 gene in which the sequences of most HEV strains are available, a 196 bp fragment of the RdRp gene, and a 439 bp fragment of the helicase gene in which the sequence of BLSV is known. Phylogenetic analyses were also performed with the complete RdRp and ORF2 genes from known HEV strains. The branch-and-bound and midpoint rooting options were used to produce the phylogenetic trees. The sequences of known HEV strains used in the sequence and phylogenetic analyses were either published or available in the Genbank database: Nepal (V. Gouvea et al., "Hepatitis E virus in Nepal: similarities with the Burmese and Indian variants," Virus Res. 52:87-96 (1997)), Egypt 93 (S. A. Tsarev et al., "Phylogenetic analysis of hepatitis E virus isolates from Egypt," J. Med. Virol. 57:68-74 (1999)), Egypt 94 (id.), Morroco (J. Meng et al., "Primary structure of open reading frame 2 and 3 of the hepatitis E virus isolated from Morocco," J. Med. Virol. 57:126-133 (1999)), Pakistan (strain Sar55) (S. A. Tsarev et al., "Characterization of a prototype strain of hepatitis E virus," Proc. Natl. Acad. Sci. USA. 89:559-63 (1992)), Burma (G. R. Reyes et al., "Isolation of a cDNA from the virus responsible for enterically transmitted non-A, non-B hepatitis," Science 247:1335-1339 (1990)), Myanmar (A. W. Tam et al., "Hepatitis E virus (HEV): molecular cloning and sequencing of the full-length viral genome," Virology 185:120-131 (1991)), Vietnam (accession no. AF 170450), Greek 1 (G. G. Schlauder et al., "Novel hepatitis E virus (HEV) isolates from Europe: evidence for additional genotypes of HEV," J. Med. Virol. 57:243-51 (1999)), Greek 2 (id), Italy (id), Mexico (C. C. Huang et al., "Molecular cloning and sequencing of the Mexico isolate of hepatitis E virus (HEV)," Virology 191:550-558 (1992)), US1 (G. G. Schlauder et al., "The sequence and phylogenetic analysis of a novel hepatitis E virus isolated from a patient with acute hepatitis reported in the United States," J. Gen. Virol. 79:447-456 (1998)), US2 (J. C. Erker et al., "A hepatitis E virus variant from the United States: molecular characterization and transmission in cynomolgus macaques," J. Gen. Virol. 80:681-690 (1999)), the U.S. strain of swine HEV (X. J. Meng et al., "A novel virus in swine is closely related to the human hepatitis E virus," Proc. Natl. Acad. Sci. USA 94:9860-9865 (1997); X. J. Meng et al., "Genetic and experimental evidence for cross-species infection by the swine hepatitis E virus," J. Virol. 72:9714-9721 (1998)), the New Zealand strain of swine HEV (accession no. AF200704), Indian strains including Hyderabad (S. K. Panda et al., "The in vitro-synthesized RNA from a cDNA clone of hepatitis E virus is infectious," J. Virol. 74:2430-2437 (2000)), Madras (accession no. X99441), X98292 (strain HEV037) (M. C. Donati et al., "Sequence analysis of full-length HEV clones derived directly from human liver in fulminant hepatitis E," VIRAL HEPATITIS AND LIVER DISEASE, pp. 313-316 (M. Rizzetto et al., eds., Edizioni Minerva Medica, Torino, 1997)), AKL 90 (V. A. Arankalle et al., "Phylogenetic analysis of hepatitis E virus isolates from India (1976-1993)," J. Gen. Virol. 80:1691-1700 (1999)), and U22532 (S. K. Panda et al., "An Indian strain of hepatitis E virus (HEV): cloning, sequence, and expression of structural region and antibody responses in sera from individuals from an area of high-level HEV endemicity," J. Clin. Microbiol. 33:2653-2659 (1995)), Taiwanese strains including TW4E, TW7E and TW8E, and Chinese strains including 93G (accession no. AF145208), L25547, Hetian, KS2, D11093 (strain Uigh 179), D11092, HEV-T1, Ch-T11 (accession no. AF151962) and Ch-T21 (accession no. AF151963).

EXAMPLE 6

Propagation of Avian HEV in Embryonated Chicken Eggs

The aim of this preliminary experiment was to generate, by biological amplification of the virus in embryonated eggs, sufficient amounts of virus for further studies, and to determine if avian HEV replicates in eggs. The undiluted positive bile sample contained about $10^7$ genomic equivalents (GE) of avian HEV per ml of bile. Embryonated SPF chicken eggs were intravenously inoculated with a diluted bile sample containing avian HEV. Five out of six embryos inoculated with $10^{-3}$ dilution and three out of six embryos inoculated with $10^{-4}$ dilution died before 21 days of embryonated age. At 12 days postinoculation (21 days of embryonated age), the remaining 4 inoculated embryos were sacrificed. The inoculated embryos showed congestion of yolk sac and hemorrhage in the liver. There are no apparent gross lesions in uninoculated embryos. Samples of bile and liver collected from inoculated eggs at the day of natural hatching (12 days postinoculation) were tested by RT-PCR. Avian HEV RNA was detected in both bile and liver samples. The titer of virus in the bile recovered from embryos was about $10^7$ genomic equivalent per ml (GE/ml), indicating that avian HEV replicates in embryonated chicken eggs. The virus recovered from inoculated eggs was used as the source for subsequent genetic characterization.

EXAMPLE 7

Amplification and Sequence Determination of the 3' Half of the Avian HEV Genome

An attempt to amplify an approximately 4 kb fragment at the 3' half of the avian HEV genome was pursued. The attempt initially failed to amplify the fragment with AmpliTaq Gold polymerase. However, in the presence of 5% v/v DMSO, a weak signal of a PCR product of approximately 4 kb was generated with AmpliTaq Gold polymerase (FIG. 1). To increase the amplification efficiency, the PCR with a mixture of pfu polymerase and Taq DNA polymerase was performed in the presence of 10 µl of cDNA and 1.7 mM $MgCL_2$ by using an eLONGase® kit. After 32 cycles of amplification, an abundant amount of PCR product of approximately 4 kb was generated (FIG. 1). The resulting PCR product was subsequently cloned into a TA vector. Three cDNA clones were selected and sequenced for both DNA strands. The number of poly (A) residues at the 3' end of each of the three cDNA clones was different (19, 23, and 26 residues, respectively), indicating that these 3 clones sequenced represent independent cDNA clones. This 4 kb genomic fragment contains the complete ORFs 2 and 3 (set forth in SEQ ID NO:7 and SEQ ID NO:9, respectively), the complete RNA-dependent RNA polymerase (RdRp) gene (set forth in SEQ ID NO:5), a partial helicase gene of the ORF1 (set forth in SEQ ID NO:3), and the complete 3' noncoding region (NCR) (set forth in SEQ ID NO:13).

EXAMPLE 8

Sequence Analysis of the ORF1 Region

The sequences of the three independent cDNA clones have the same size but differ in 16 nucleotide positions. However, at any given position, two of the three cDNA clones have the same nucleotide. Therefore, a consensus sequence was produced. The resulting consensus sequence of the 3' half genomic fragment of avian HEV is 3,931 nucleotides in length, excluding the poly (A) tract at the 3' end and the sequence of the 5' sense primer used for amplification. Sequence analysis revealed that the novel virus associated with HS in chickens is genetically related to human and swine HEV. Two complete ORFs (ORFs 2 and 3), and one incomplete ORF1 were identified in this genomic region.

Figure 2A:
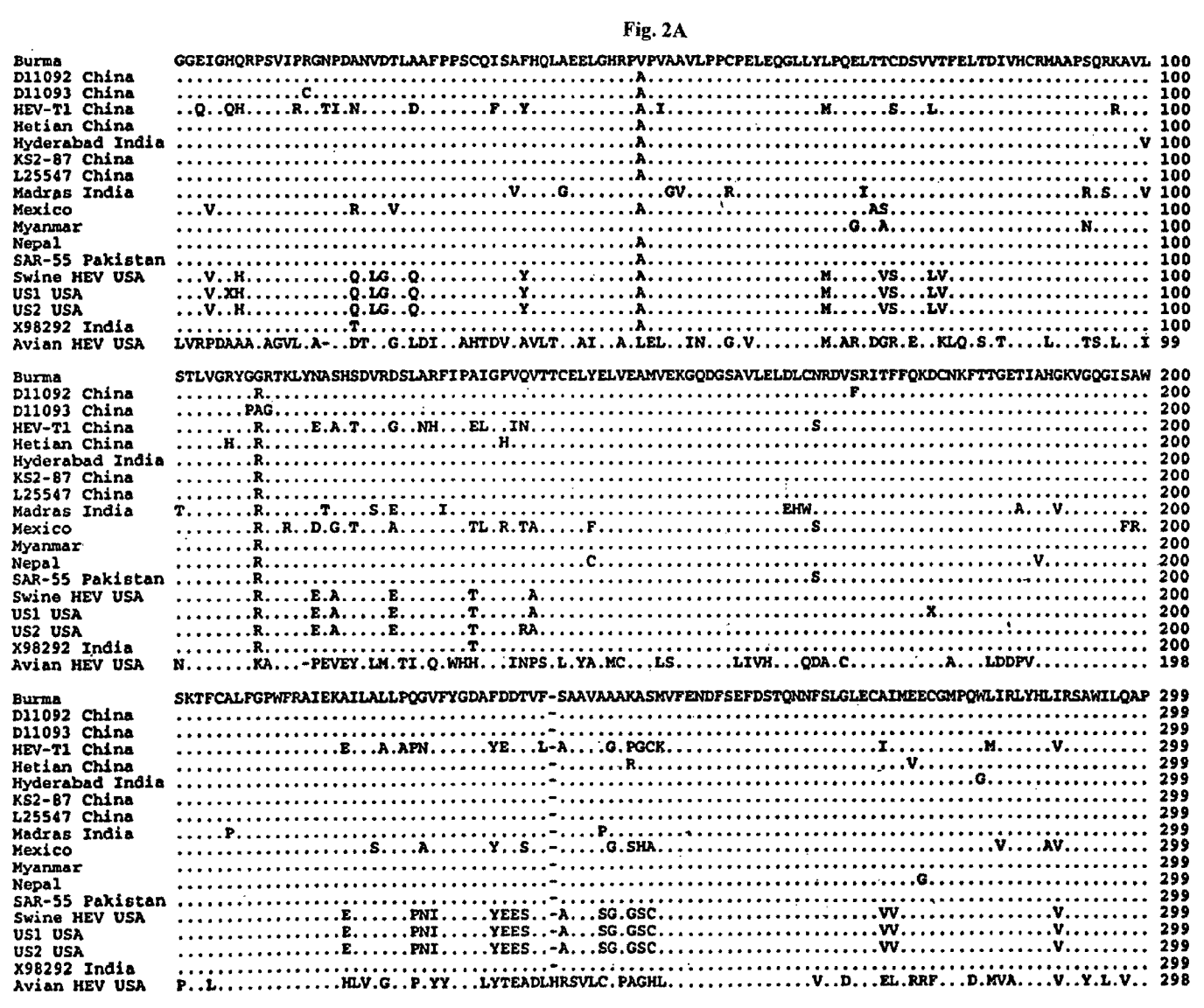
Figure 2B:
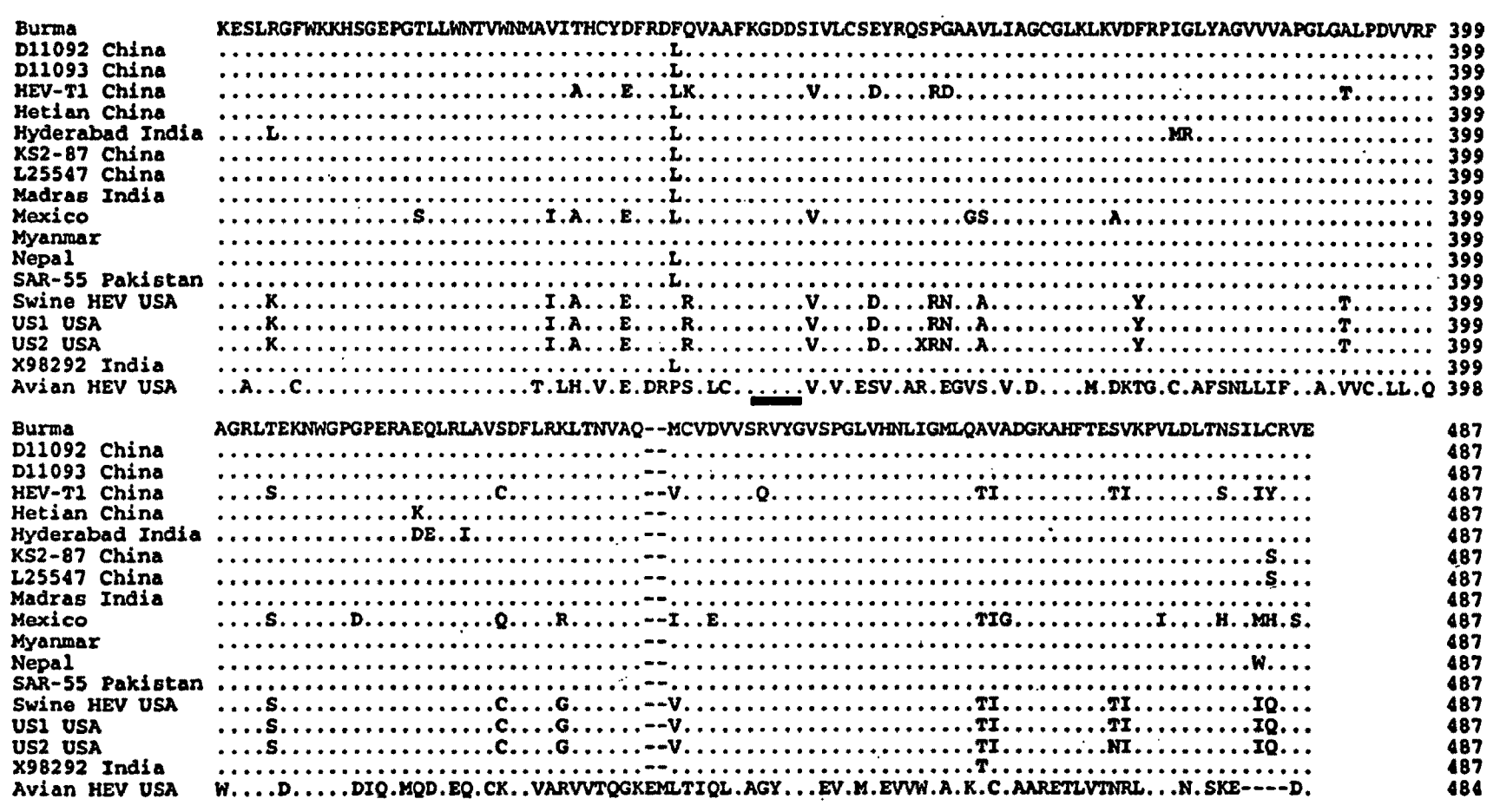

The incomplete ORF1 sequence of avian HEV was aligned with the corresponding regions of human and swine HEV strains. Significant nucleotide and amino acid sequence identities were found in the ORF1 region between avian HEV and known HEV strains (Table 2, below). The avian HEV ORF1 region sequenced thus far contained the complete RdRp gene and a partial helicase gene. The RdRp gene of avian HEV encodes 483 amino acid residues and terminates at the stop codon of ORF1. A GDD motif (positions 343-345 in RdRp gene) that is believed to be critical for viral replication was identified (FIGS. 2A-2B corresponding to SEQ ID NO:4), and this motif was found in all RdRps (G. Kamer et al., "Primary structural comparison of RNA-dependent polymerases from plant, animal and bacterial viruses," Nucleic Acids Res. 12:7269-7282 (1984)). The RdRp gene of avian HEV is 4 amino acid residues shorter than that of known HEV strains (FIGS. 2A-2B corresponding to SEQ ID NO:4), and shared 47% to 50% amino acid and 52% to 53% nucleotide sequence identity with that of known HEV strains (Table 2, below). The C-terminal 146 amino acid residues of the incomplete helicase gene of avian HEV shared approximately 57-60% nucleotide sequence and 58-60% amino acid sequence identities with the corresponding region of other HEV strains. The helicase gene of avian HEV is the most conserved region compared to known HEV strains. There is no deletion or insertion in this partial helicase gene region between avian HEV and other HEV strains. A 439 bp sequence of BLSV is available in the helicase gene region (C. J. Payne et al., 1999, supra), and avian HEV shared 80% nucleotide sequence identity with BLSV in this region.

TABLE 2

Pairwise comparison of the RNA-dependent RNA polymerase (RdRp) gene of the avian HEV with that of known HEV strains

| | Avian HEV | Burma | D11092 China | D11093 China | HEV-T1 China | Hetian China | Hydarabad India | K52-87 China | Madras |
|---|---|---|---|---|---|---|---|---|---|
| Avian HEV | | 53[a] | 53 | 53 | 53 | 53 | 52 | 53 | 52 |
| Burma | 49 | | 93 | 93 | 76 | 93 | 96 | 93 | 95 |
| D11092 China | 47 | 94 | | 97 | 75 | 98 | 92 | 98 | 91 |
| D11093 China | 49 | 98 | 94 | | 74 | 97 | 92 | 98 | 91 |
| HEV-T1 China | 50 | 86 | 82 | 86 | | 75 | 75 | 75 | 74 |
| Hetian China | 49 | 98 | 93 | 98 | 86 | | 92 | 98 | 90 |
| Hydarabad India | 49 | 97 | 93 | 97 | 85 | 97 | | 92 | 94 |
| K52-87 China | 49 | 99 | 94 | 98 | 87 | 98 | 98 | | 91 |
| Madras India | 47 | 95 | 90 | 94 | 82 | 94 | 94 | 95 | |
| Mexico | 48 | 88 | 84 | 88 | 85 | 88 | 87 | 89 | 85 |
| Myanmar | 49 | 99 | 93 | 98 | 86 | 97 | 97 | 98 | 95 |
| Nepal | 49 | 98 | 93 | 98 | 86 | 98 | 97 | 98 | 94 |
| Sar-55 Pakistan | 49 | 99 | 94 | 98 | 87 | 98 | 98 | 99 | 95 |
| Swine HEV USA | 49 | 87 | 83 | 87 | 89 | 87 | 86 | 88 | 84 |
| US1 USA | 49 | 87 | 82 | 87 | 89 | 87 | 86 | 87 | 83 |
| US2 USA | 49 | 87 | 82 | 87 | 88 | 87 | 86 | 87 | 83 |
| X98292 India | 49 | 98 | 94 | 98 | 87 | 98 | 97 | 99 | 94 |

| | Mexico | Myanmar | Nepal | Sar-55 Pakistan | Swine HEV USA | US1 USA | US2 USA | X98292 India |
|---|---|---|---|---|---|---|---|---|
| Avian HEV | 52 | 53 | 53 | 53 | 52 | 52 | 52 | 53 |
| Burma | 74 | 98 | 96 | 93 | 75 | 74 | 75 | 93 |
| D11092 China | 76 | 93 | 92 | 98 | 75 | 75 | 75 | 94 |
| D11093 China | 76 | 93 | 91 | 97 | 75 | 74 | 75 | 94 |
| HEV-T1 China | 73 | 75 | 76 | 75 | 76 | 75 | 75 | 75 |
| Hetian China | 74 | 93 | 92 | 98 | 75 | 74 | 75 | 94 |
| Hydarabad India | 76 | 96 | 95 | 92 | 75 | 74 | 74 | 92 |
| K52-87 China | 76 | 93 | 92 | 98 | 75 | 75 | 75 | 94 |
| Madras India | 75 | 94 | 95 | 91 | 74 | 73 | 74 | 91 |
| Mexico | | 76 | 76 | 77 | 74 | 62 | 73 | 76 |
| Myanmar | 88 | | 95 | 93 | 75 | 74 | 75 | 92 |
| Nepal | 88 | 98 | | 92 | 75 | 75 | 75 | 92 |
| Sar-55 Pakistan | 89 | 98 | 98 | | 75 | 75 | 75 | 94 |
| Swine HEV USA | 86 | 87 | 87 | 88 | | 92 | 92 | 76 |
| US1 USA | 86 | 87 | 87 | 87 | 99 | | 92 | 75 |
| US2 USA | 86 | 87 | 87 | 87 | 99 | 98 | | 75 |
| X98292 India | 89 | 98 | 98 | 99 | 88 | 88 | 88 | |

[a]The values in the table are percentage identity of amino acids (lower left half) or nucleotides (upper right half).

EXAMPLE 9

Sequence Analysis of the ORFs 2 and 3

Figure 3A:
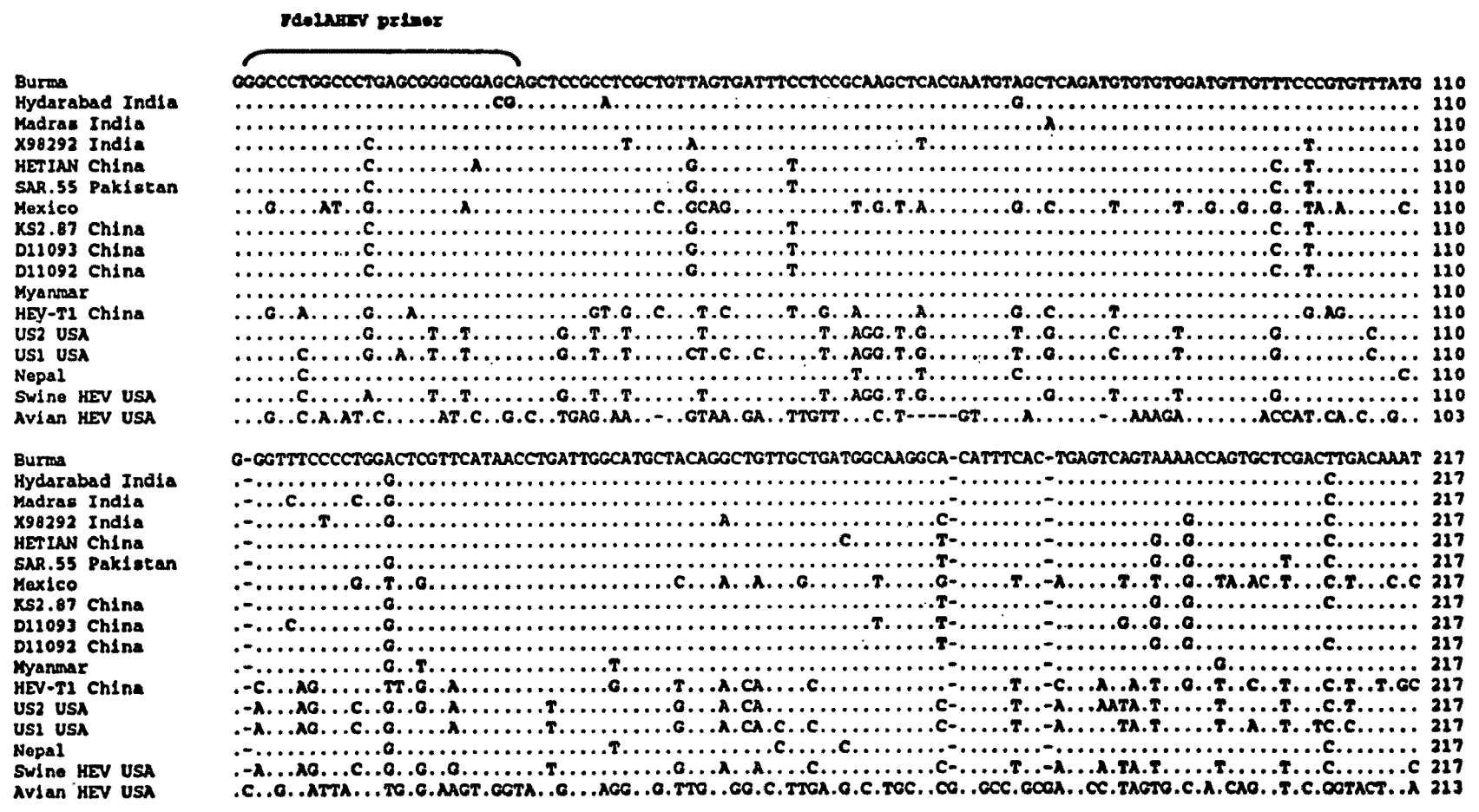
Figure 3B:
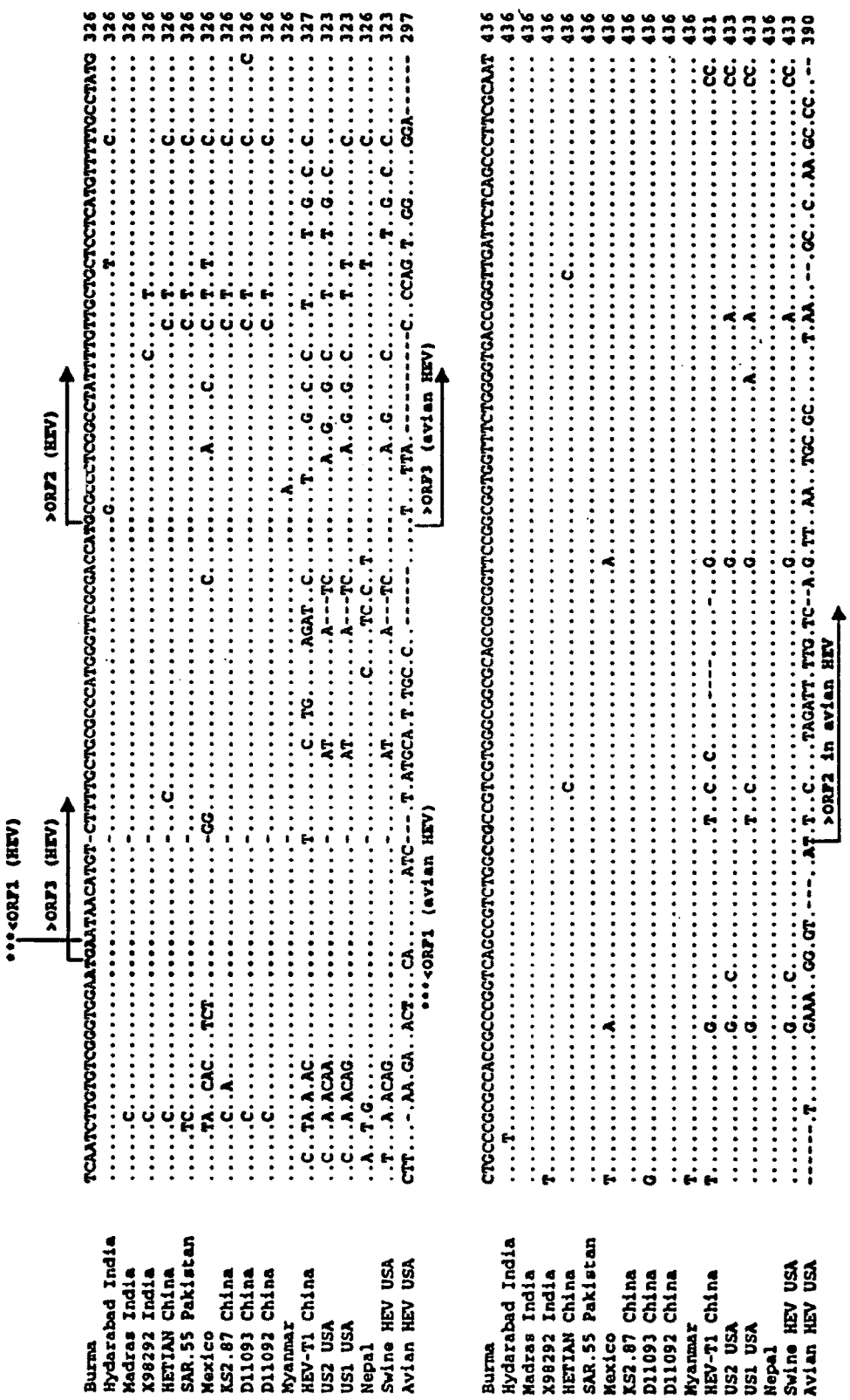
Figure 3C:
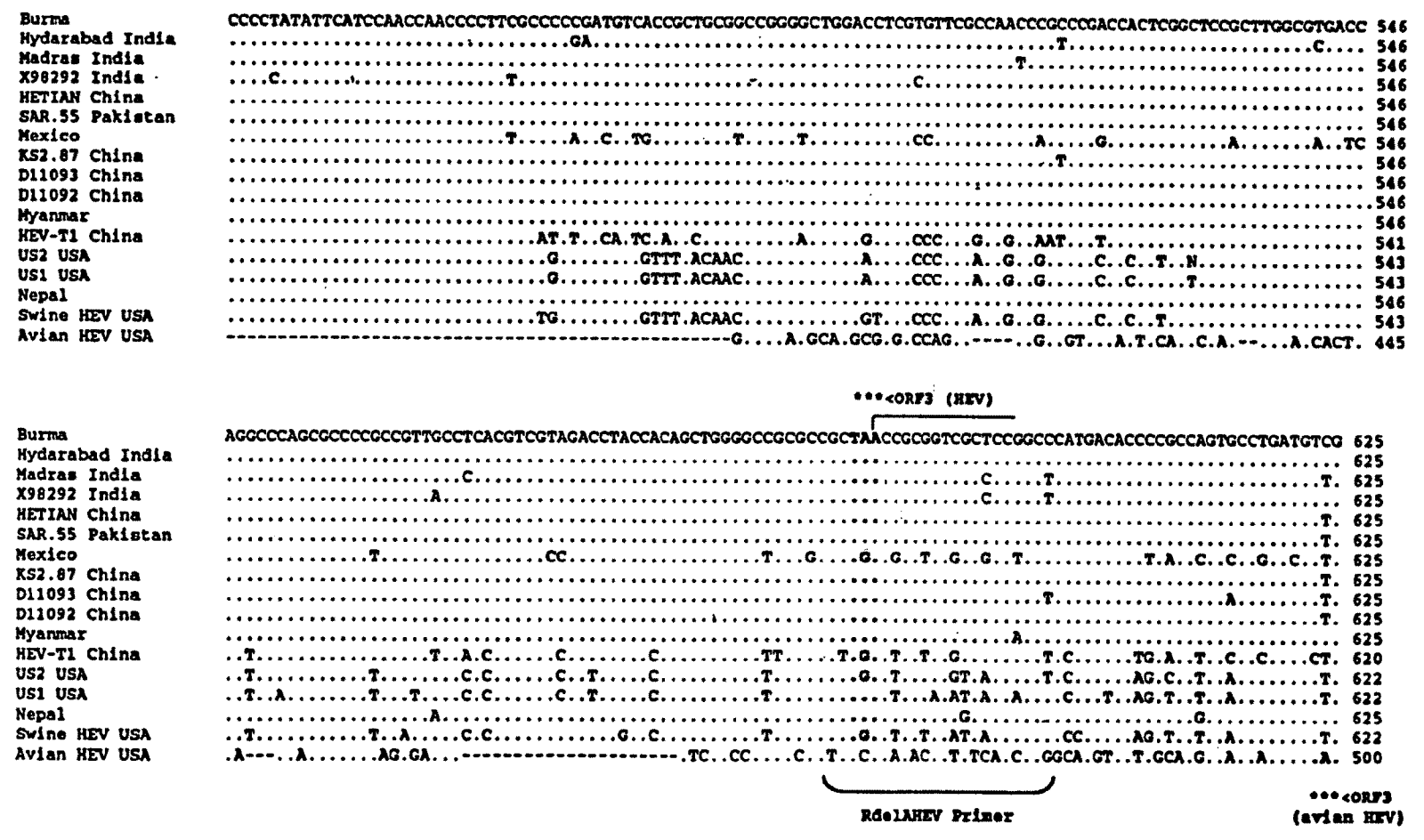
Figure 4:
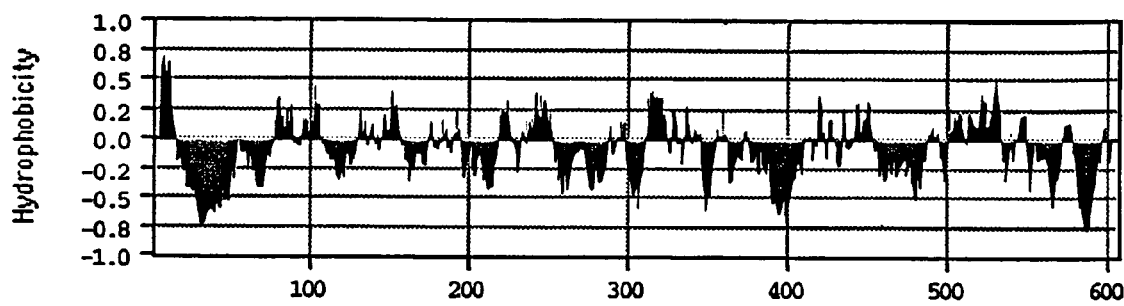
FIG. 4 shows the hydropathy plot of the putative ORF2 protein of avian HEV. A highly hydrophobic domain is identified at the N-terminus of the protein followed by a hydrophilic region. The hydrophobic domain is the putative signal peptide of ORF2. The horizontal scale indicates the relative position of amino acid residues of the ORF2.
Figure 5A:
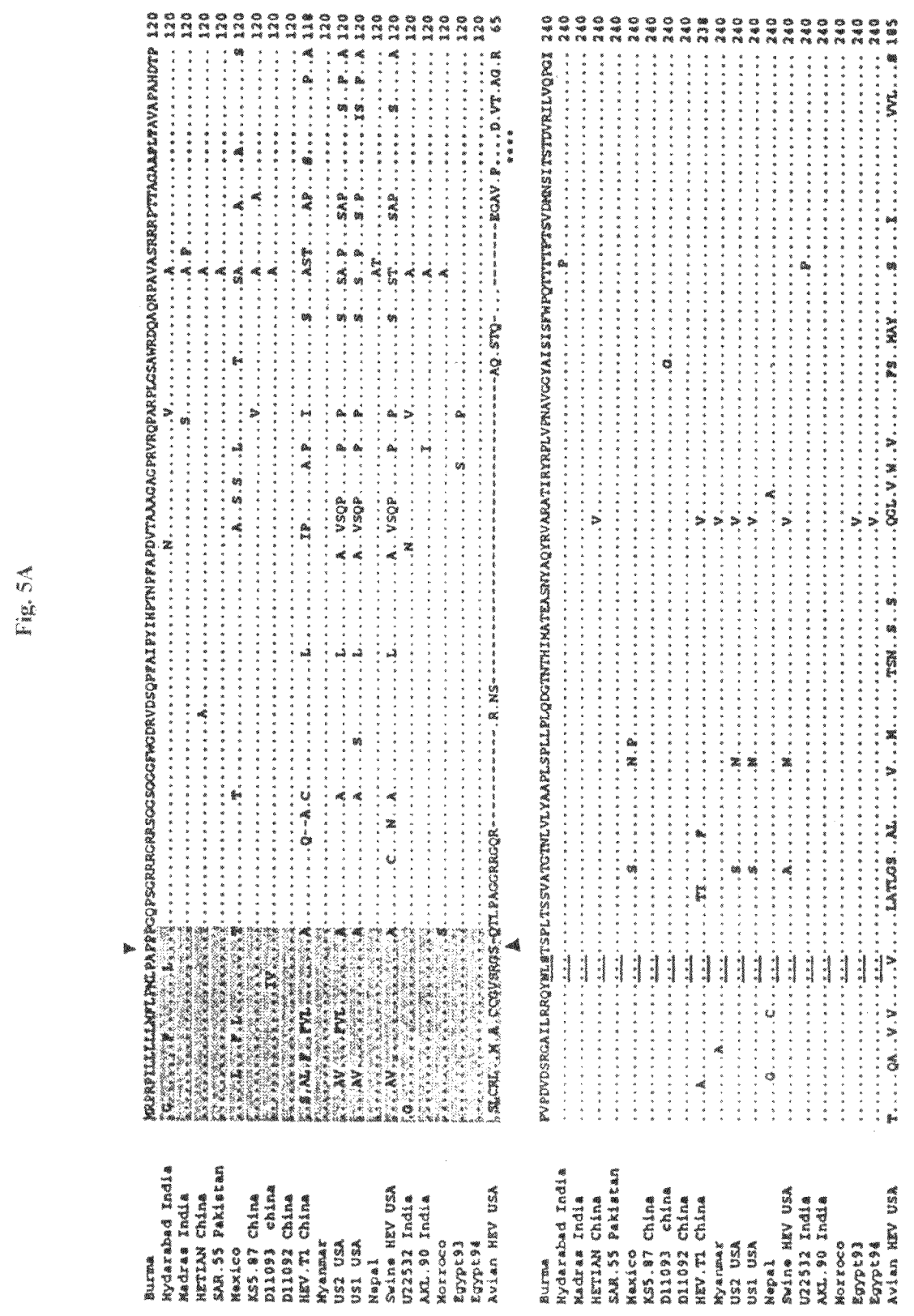
Figure 5B:
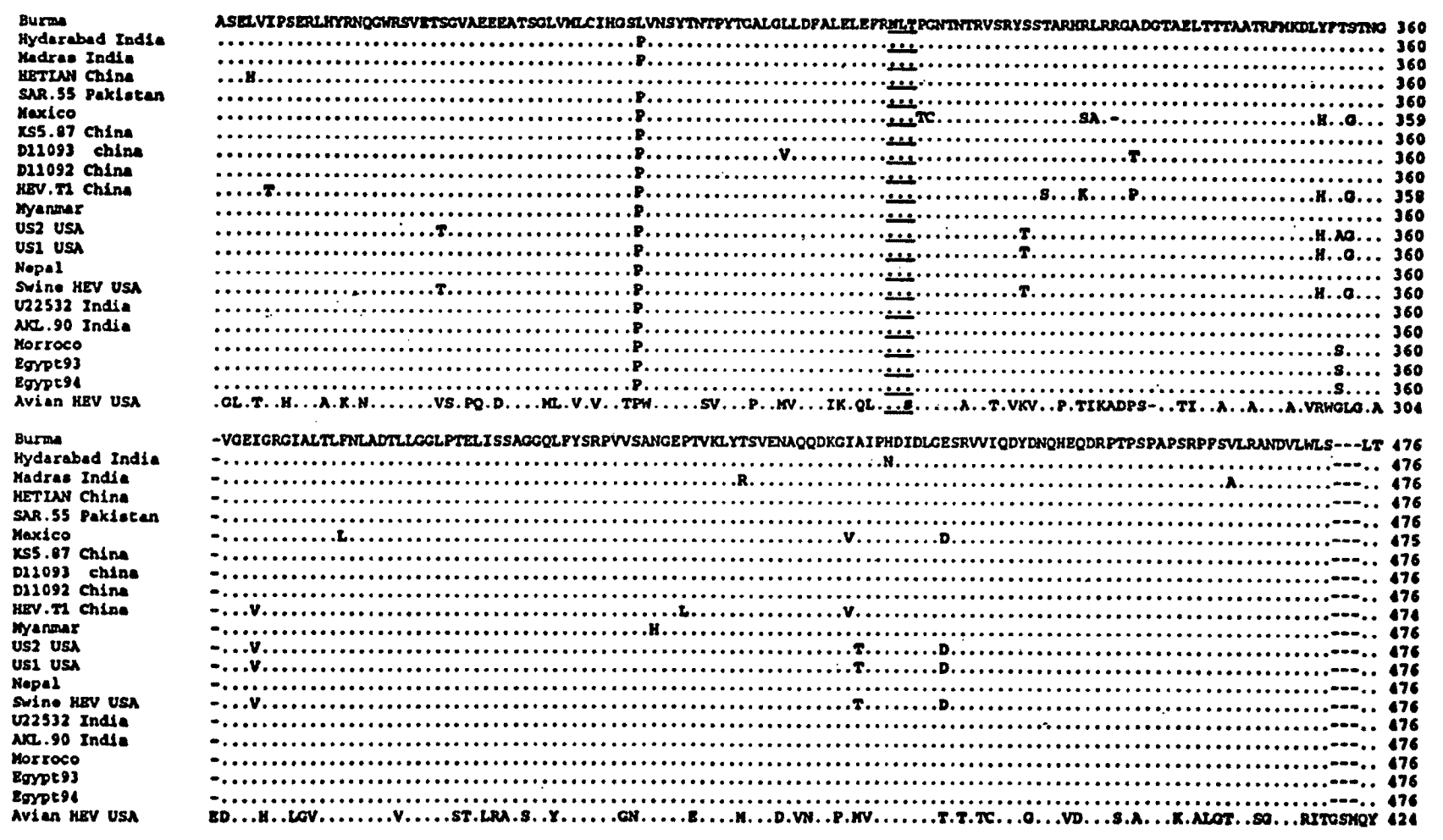
Figure 5C:
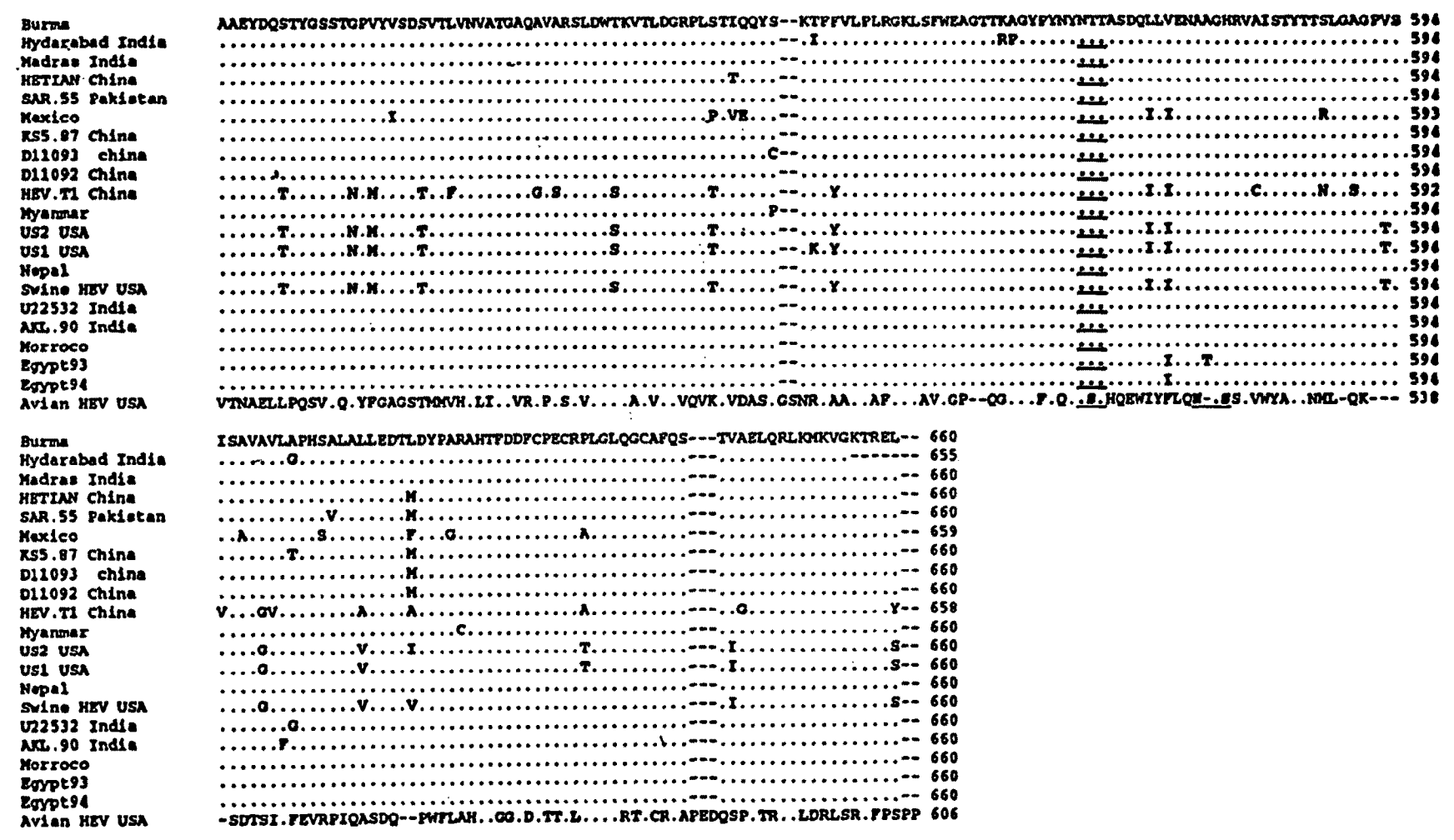

The ORF2 gene of avian HEV consists of 1,821 nucleotides with a coding capacity of 606 amino acids, about 60 amino acids shorter than that of other HEV strains. The ORF2 gene of avian HEV overlaps with ORF3 (FIGS. 3A-3C corresponding to SEQ ID NO:12), and terminates at stop codon UAA located 130 bases upstream the poly (A) tract. The predicted amino acid sequence of ORF2 contains a typical signal peptide at its N-terminus followed by a hydrophilic domain (FIG. 4). The sequence of the avian HEV signal peptide is distinct from that of known HEV strains (FIGS. 5A-5C corresponding to SEQ ID NO:6). However, it contains common signal peptide features that are necessary for the translocation of the peptide into endoplasmic reticulum: a positively charged amino acid (Arginine) at its N-terminus, a core of highly hydrophobic region (rich in Leucine residues) and a cleavage site (SRG-SQ) between position 19 and 20 (FIGS. 5A-5C corresponding to SEQ ID NO:6). Sequence analysis of the ORF2 revealed that the region between the signal peptide and the conserved tetrapeptide APLT (positions 108-111) is hypervariable, and 54 amino acid residues of avian HEV are deleted in this region (FIGS. 5A-5C corresponding to SEQ ID NO:6). Three putative N-linked glycosylation sites were identified in the ORF2 of avian HEV: NLS (pos. 255-257), NST (pos. 510-512) and NGS (pos. 522-524). Three N-linked glycosylation sites were also identified in known HEV strains but the locations are different from those of avian HEV. The first glycosylation site in known HEV strains is absent in avian HEV (FIGS. 5A-5C corresponding to SEQ ID NO:6), and the third glycosylation site in avian HEV is absent in the known HEV strains.

The ORF2 gene of known HEV strains varies slightly in size, ranging from 655 to 672 amino acid residues, but most strains have a ORF2 gene of 660 amino acid residues. The ORF2 of avian HEV has 606 amino acid residues, which is 54 amino acids shorter than that of most known HEV strains. The deletions are largely due to the shift of the ORF2 start codon of avian HEV to 80 nucleotides downstream from that of known HEV strains (FIGS. 3A-3C corresponding to SEQ ID NO:12). The putative capsid gene (ORF2) of avian HEV shared only 42% to 44% amino acid sequence identity with that of known HEV strains (Table 3, below), when the major deletion at the N-terminus is taken into consideration. However, when the N-terminal deletion is not included in the comparison, avian HEV shared 48% to 49% amino acid sequence identity with the corresponding region of other HEV strains.

Multiple sequence alignment revealed that the normal start codon of the ORF3 gene in known HEV strains does not exist in avian HEV due to base substitutions (FIGS. 3A-3C corresponding to SEQ ID NO:12). Avian HEV utilizes the ORF2 start codon of other HEV strains for its ORF3, and consequently the ORF3 of avian HEV starts 41 nucleotides downstream from the start codon of known HEV strains (FIGS. 3A-3C corresponding to SEQ ID NO:12). Unlike known HEV strains, the ORF3 gene of avian HEV does not overlap with the ORF1 and locates 33 bases downstream from the ORF1 stop codon (FIGS. 3A-3C corresponding to SEQ ID NO:12). The ORF3 of avian HEV consists of 264 nucleotides with a coding capacity of 87 amino acid residues, which is 24 to 37 amino acid residues shorter than that of known HEV strains. Sequence analysis indicated that the ORF3 of avian HEV is very divergent compared to that of known HEV strains.

TABLE 3

Pairwise comparison of the putative capsid gene (ORF2) of avian HEV with that of known HEV strains

| | Avian HEV[a] | Avian HEV[b] | Burma | D11092 China | D11093 China | HEV-T1 China | Hetian China | Hydarabad India | KS2-87 China | Madras | Mexico |
|---|---|---|---|---|---|---|---|---|---|---|---|
| Avian HEV[a] | | | 47 | 47 | 47 | 44 | 47 | 47 | 47 | 47 | 45 |
| Avian HEV[b] | | | 51 | 51 | 51 | 48 | 51 | 51 | 51 | 51 | 49 |
| Burma | 44 | 49 | | 94 | 93 | 77 | 94 | 96 | 94 | 96 | 80 |
| D11092 China | 44 | 49 | 99 | | 97 | 77 | 98 | 93 | 98 | 93 | 81 |
| D11093 China | 44 | 49 | 98 | 98 | | 77 | 97 | 93 | 98 | 93 | 80 |
| HEV-T1 China | 42 | 48 | 88 | 88 | 87 | | 77 | 76 | 77 | 77 | 77 |
| Hetian China | 44 | 49 | 99 | 99 | 98 | 88 | | 93 | 98 | 93 | 80 |
| Hydarabad India | 44 | 49 | 97 | 97 | 96 | 86 | 96 | | 93 | 95 | 80 |
| KS2-87 China | 44 | 49 | 99 | 99 | 98 | 88 | 98 | 97 | | 93 | 81 |
| Madras India | 44 | 49 | 99 | 99 | 98 | 88 | 98 | 96 | 98 | | 80 |
| Mexico | 43 | 48 | 93 | 93 | 92 | 86 | 92 | 91 | 92 | 92 | |
| Myanmar | 43 | 48 | 98 | 98 | 98 | 87 | 98 | 96 | 98 | 98 | 92 |
| Nepal | 44 | 49 | 98 | 98 | 98 | 87 | 98 | 96 | 98 | 98 | 92 |
| Sar-55 Pakistan | 44 | 49 | 99 | 99 | 98 | 88 | 99 | 97 | 99 | 99 | 93 |
| Swine HEV USA | 43 | 49 | 91 | 91 | 90 | 90 | 91 | 89 | 91 | 91 | 90 |
| US1 USA | 43 | 49 | 91 | 92 | 91 | 88 | 91 | 90 | 91 | 91 | 90 |
| US2 USA | 44 | 49 | 91 | 91 | 91 | 90 | 91 | 90 | 91 | 91 | 90 |
| Egypt93 | 44 | 49 | 98 | 98 | 97 | 88 | 98 | 96 | 98 | 98 | 92 |
| Egypt94 | 44 | 49 | 99 | 99 | 98 | 88 | 98 | 96 | 98 | 98 | 93 |
| Morroco | 44 | 49 | 99 | 99 | 98 | 88 | 98 | 97 | 98 | 98 | 93 |
| AKL90 | 44 | 49 | 99 | 99 | 98 | 88 | 98 | 97 | 98 | 98 | 93 |

| | Myanmar | Nepal | Sar-55 Pakistan | Swine HEV USA | US1 USA | US2 USA | Egypt93 | Egypt94 | Morroco | AKL90 |
|---|---|---|---|---|---|---|---|---|---|---|
| Avian HEV[a] | 47 | 47 | 47 | 46 | 45 | 46 | 47 | 47 | 48 | 47 |
| Avian HEV[b] | 51 | 51 | 51 | 50 | 49 | 50 | 51 | 51 | 51 | 51 |
| Burma | 97 | 98 | 93 | 79 | 79 | 79 | 91 | 90 | 89 | 97 |
| D11092 China | 93 | 93 | 98 | 80 | 79 | 79 | 91 | 91 | 90 | 93 |
| D11093 China | 93 | 93 | 97 | 79 | 78 | 79 | 91 | 91 | 90 | 93 |

TABLE 3-continued

Pairwise comparison of the putative capsid gene (ORF2) of avian HEV with that of known HEV strains

| | | | | | | | | | | |
|---|---|---|---|---|---|---|---|---|---|---|
| HEV-T1 China | 78 | 77 | 78 | 78 | 78 | 79 | 77 | 77 | 78 | 77 |
| Hetian China | 93 | 93 | 98 | 80 | 79 | 79 | 91 | 91 | 90 | 93 |
| Hydarabad India | 95 | 97 | 92 | 79 | 78 | 79 | 90 | 90 | 89 | 97 |
| KS2-87 China | 93 | 93 | 98 | 80 | 79 | 79 | 91 | 91 | 90 | 93 |
| Madras India | 96 | 96 | 92 | 97 | 97 | 97 | 90 | 90 | 90 | 96 |
| Mexico | 80 | 80 | 81 | 78 | 77 | 79 | 80 | 80 | 81 | 80 |
| Myanmar | | 96 | 93 | 79 | 79 | 79 | 91 | 90 | 89 | 96 |
| Nepal | 98 | | 93 | 79 | 79 | 79 | 90 | 90 | 90 | 97 |
| Sar-55 Pakistan | 98 | 98 | | 80 | 79 | 79 | 91 | 91 | 91 | 93 |
| Swine HEV USA | 91 | 90 | 91 | | 92 | 92 | 79 | 79 | 80 | 79 |
| US1 USA | 91 | 91 | 91 | 97 | | 91 | 78 | 79 | 79 | 79 |
| US2 USA | 92 | 91 | 91 | 98 | 98 | | 79 | 79 | 79 | 79 |
| Egypt93 | 98 | 97 | 98 | 91 | 92 | 92 | | 96 | 91 | 91 |
| Egypt94 | 98 | 98 | 98 | 91 | 92 | 91 | 99 | | 91 | 90 |
| Morroco | 98 | 98 | 99 | 91 | 91 | 91 | 98 | 99 | | 90 |
| AKL90 | 98 | 98 | 99 | 91 | 91 | 91 | 98 | 98 | 99 | |

The values in the table are percentage identity of amino acids (lower left half) or nucleotides (upper right half).
[a]Percentage identity when the major deletion at the N-terminal region of ORF2 is taken into consideration.
[b]Percentage identity when the major deletion is not included in the comparison.

EXAMPLE 10

Sequence Analysis of the 3' NCRs

The region between the stop codon of the ORF2 and the poly (A) tail of avian HEV, the 3' NCR, is 127 nucleotides (set forth in SEQ ID NO:13). Sequence analysis revealed that the 3' NCR of avian HEV is the longest among all known HEV strains. The 3 NCRs of known HEV strains range from 65 to 74 nucleotides (FIG. 6 corresponding to SEQ ID NO:13). Multiple sequence alignment indicated that the 3' NCRs of HEV is highly variable, although a stretch of sequence immediately proceeding the poly (A) tract is relatively conserved (FIG. 6 corresponding to SEQ ID NO:13).

EXAMPLE 11

Figure 7:
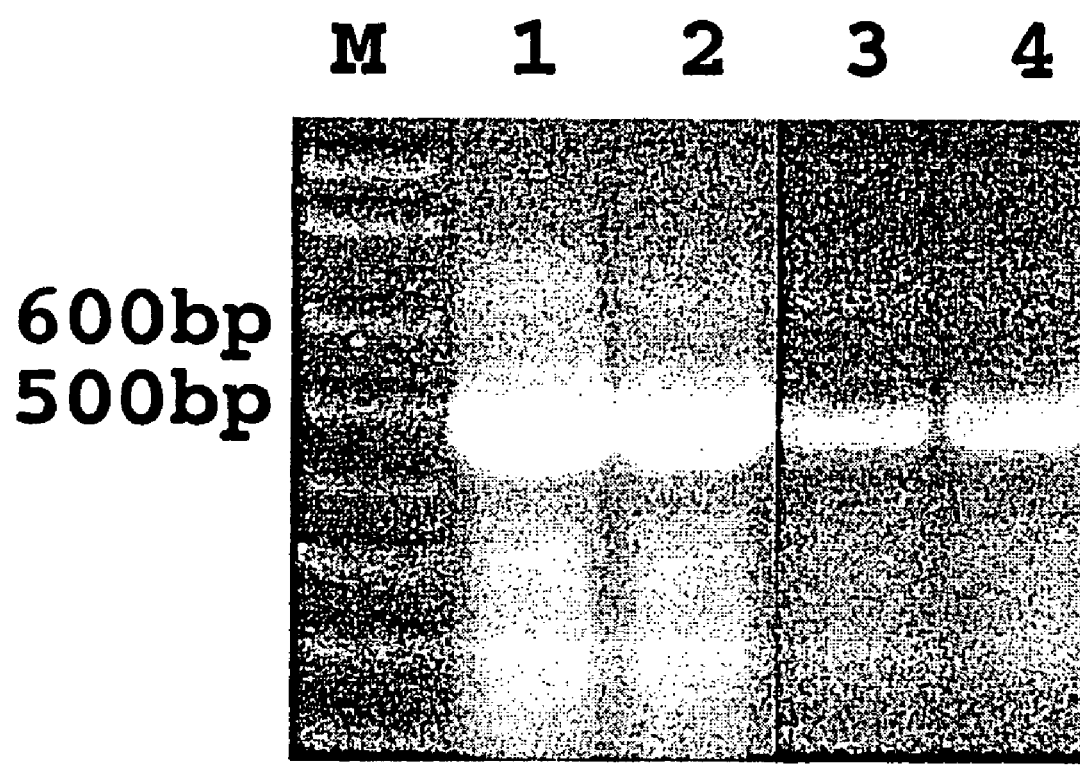
FIG. 7 represents the RT-PCR amplification of the avian HEV genomic region with a major deletion: Lane M, 1 kb ladder; Lanes 1 and 2, PCR amplification without DMSO; Lane 3, PCR amplification in the presence of 5% v/v DMSO; Lane 4, PCR amplification in the presence of 5% v/v formamide.

Identification of a Major Deletion in the ORFs 2 and 3 Overlapping Region of Avian HEV Sequence analyses revealed a major deletion of 54 amino acid residues in avian HEV between the putative signal peptide and the conserved tetrapeptide APLT of the ORF2 (FIGS. 5A-5C corresponding to SEQ ID NO:6). To rule out the possibility of RT-PCR artifacts, a pair of avian HEV-specific primers flanking the deleted region was designed (Table 1, FIGS. 3A-3C corresponding to SEQ ID NO:12). The 3' antisense primer (RdelAHEV) located before the ORF3 stop codon of avian HEV, and the 5' sense primer (FdelAHEV) located within the C-terminal region of the ORF1. To minimize potential secondary structure problems, reverse transcription was performed at 60° C. with a One Step RT-PCR Kit (Qiagen Inc., Valencia, Calif.). PCR was performed with 35 cycles of denaturation at 95° C. for 40 seconds, annealing at 55° C. for 30 seconds and extension at 72° C. for 1 minute. In addition, PCR was also performed with shorter annealing time and higher denaturation temperature to avoid potential problems due to secondary structures. The PCR reaction consisted of an initial enzyme activation step at 95° C. for 13 minutes, followed by 35 cycles of denaturation at 98° C. for 20 seconds, annealing at 55° C. for 5 seconds and extension at 73° C. for 1 minute. It has been reported that formamide or DMSO could enhance the capability of PCR to amplify certain genomic regions of HEV (S. Yin et al., "A new Chinese isolate of hepatitis E virus: comparison with strains recovered from different geographical regions," Virus Genes 9:23-32 (1994)). Therefore, a sufficient amount to make 5% (v/v) of formamide or DMSO was added in the PCR reactions. A PCR product of the same size (502 bp) as observed in a conventional PCR is produced with various different RT-PCR parameters and conditions including the addition of 5% (v/v) of formamide or DMSO, the use of higher denaturation temperature and short annealing time, and the synthesis of cDNA at 60° C. (FIG. 7). The deletion was further confirmed by directly sequencing the 502 bp PCR product.

EXAMPLE 12

Phylogenetic Evidence of Avian HEV as a New Genotype

Figure 8A:
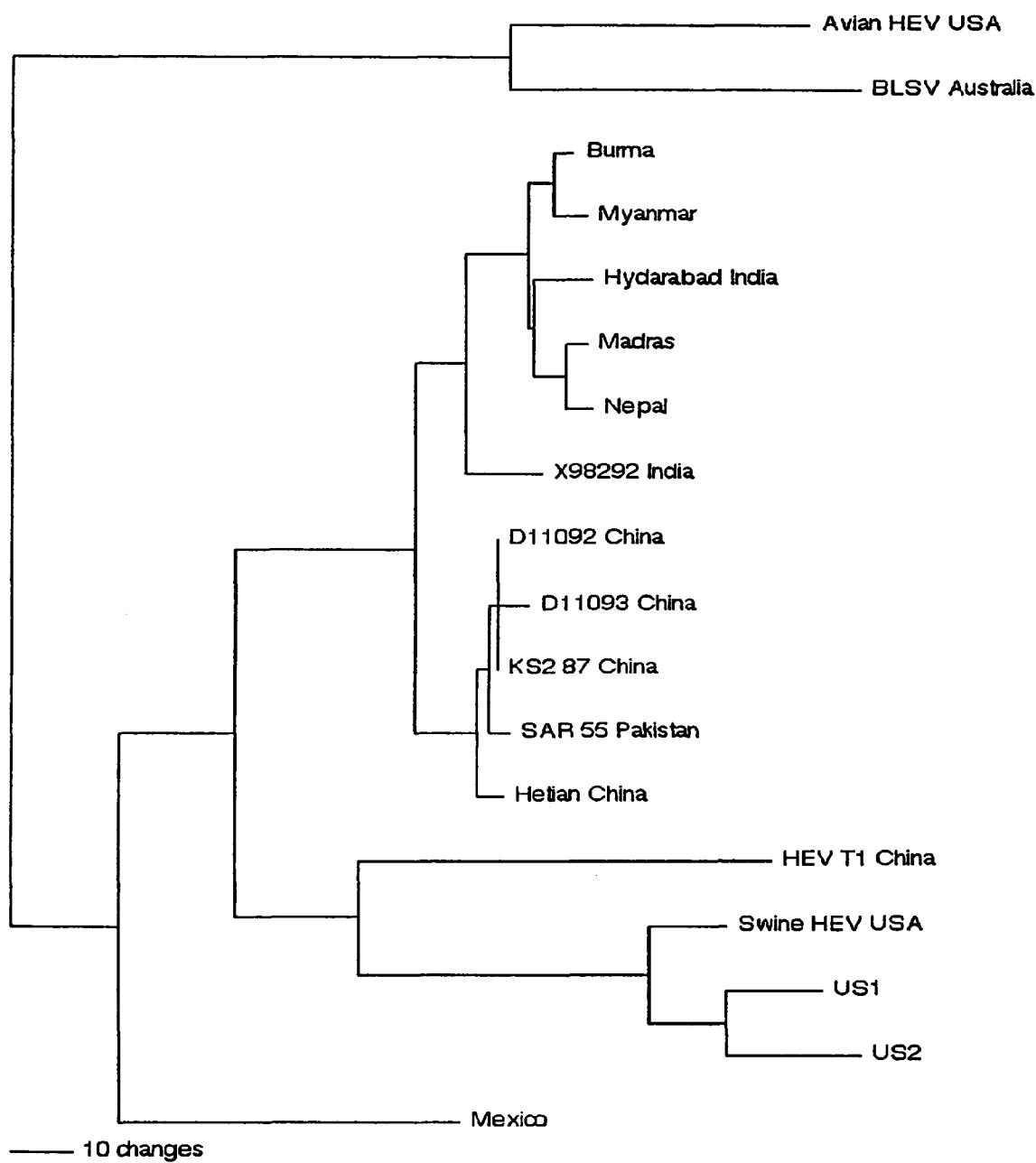
Figure 8B:
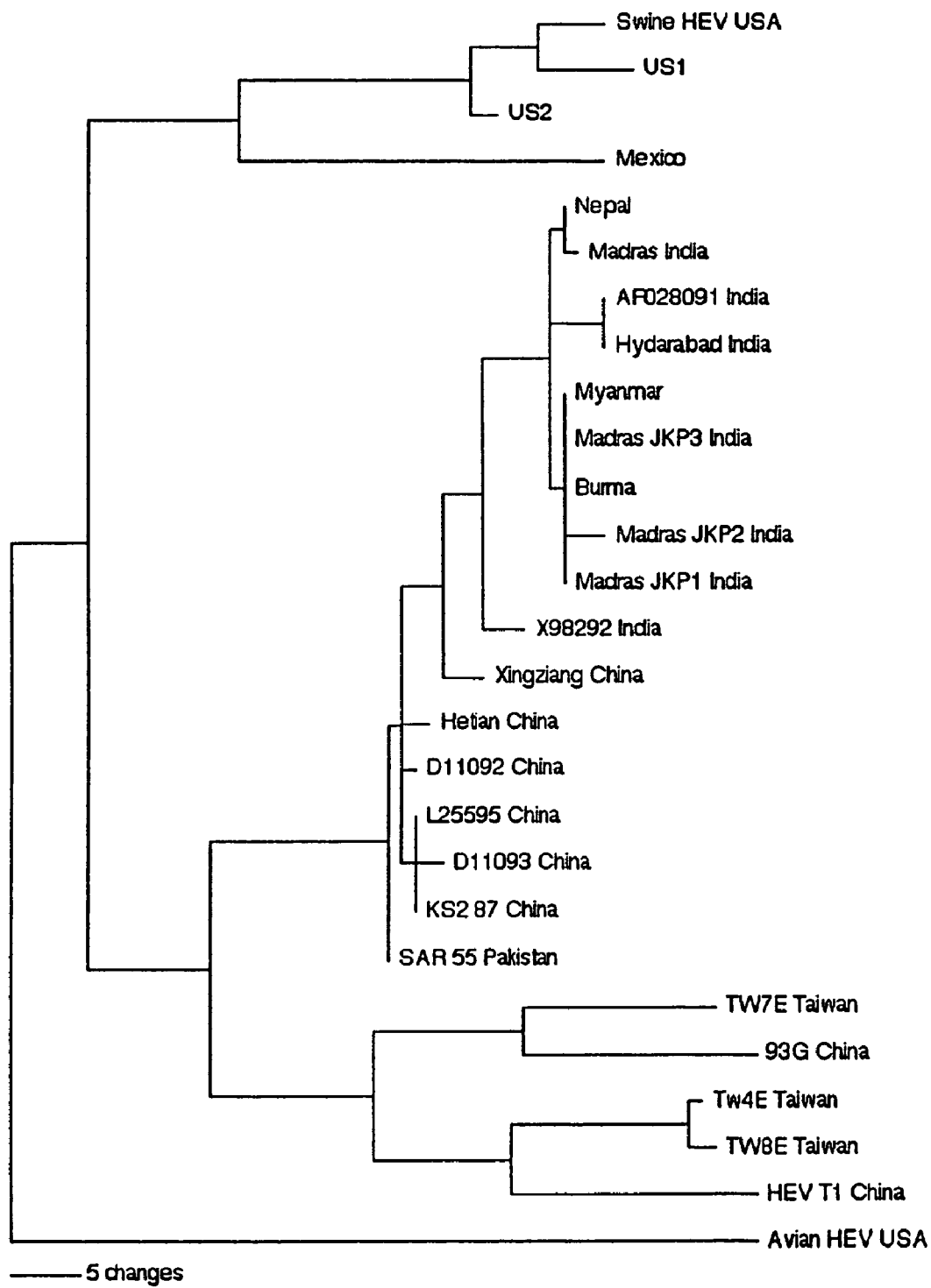
Figure 8C:
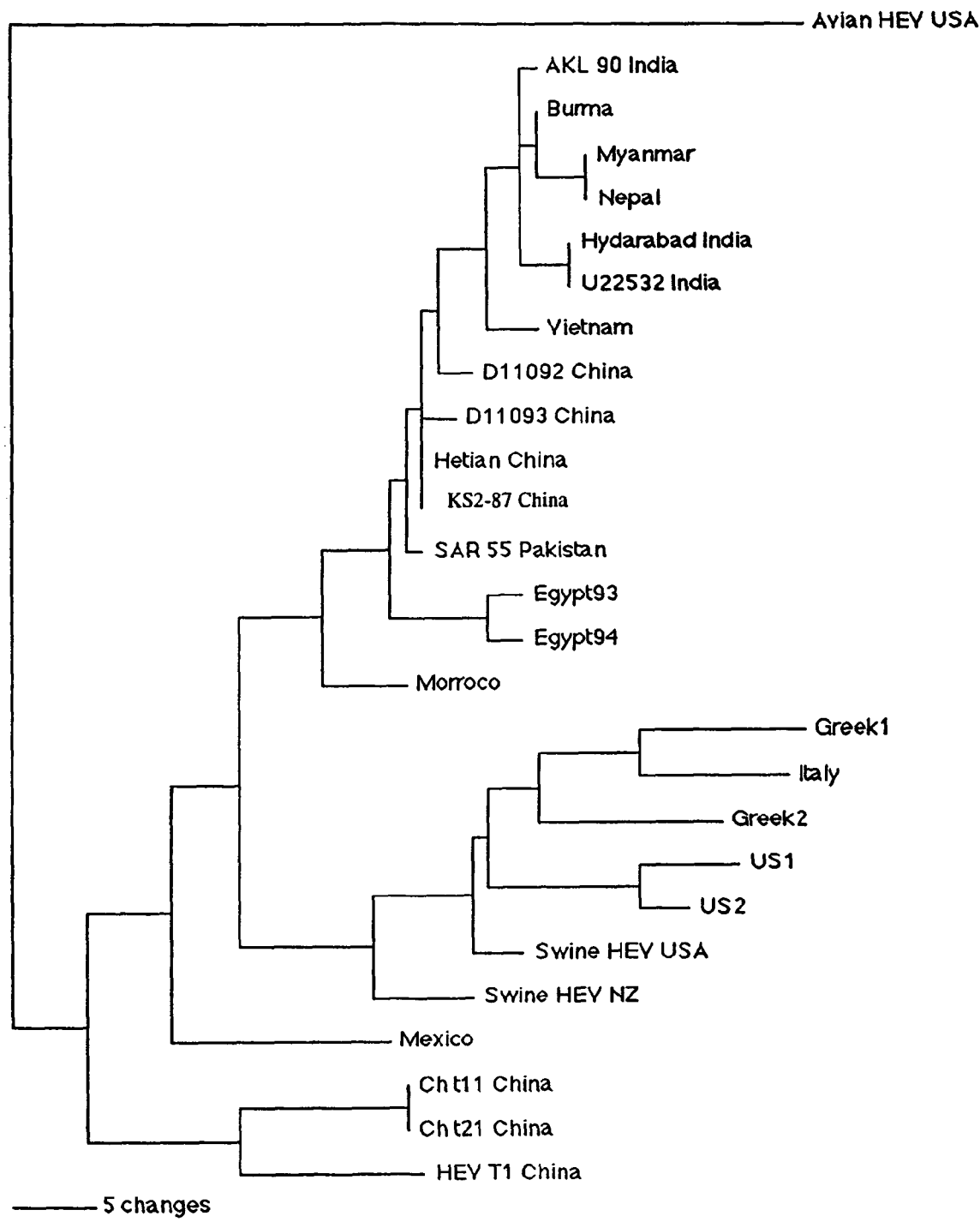

Phylogenetic analyses based on three different genomic regions of HEV (a 439 bp of the helicase gene, a 196 bp of the RdRp gene, and a 148 bp of the ORF2 gene) identified at least 5 distinct genotypes of HEV (FIG. 8). The topology of the three trees based on different genomic regions is very similar. Similar phylogenetic trees were also produced with the complete RdRp and ORF2 genes of HEV strains in which their sequences are known. Most Asian strains of HEV are related to the prototype Burmese strain and clustered together, and these Burmese-like Asian strains of HEV represent genotype 1. The African strains of HEV (Egypt 93, Egypt 94 and Morroco) were related to, but distinct from, Burmese-like strains in the genotype 1. The limited sequences available for these African strains do not allow for a determination of whether they represent a distinct genotype or a subgenotype within the genotype 1. The single Mexican strain of HEV represents genotype 2. The genotype 3 of HEV consists of two U.S. strains of human HEV (US1, US2), a U.S. strain of swine HEV, a New Zealand strain of swine HEV, and several European strains of human HEV (Greek 1, Greek 2, Italy). The genotype 4 includes several strains of HEV identified from patients in China (HEV-T1, Ch-T11, Ch-T21, 93G) and Taiwan (TW7E, TW4E, TW8E). Avian HEV is the most divergent and represents the new genotype 5. Based on the limited sequence available for BLSV, it appears that the BLSV identified from chickens in Australia clustered with the genotype 5 of avian HEV, but the avian HEV retained significant differences in nucleotide sequence indicating that the avian HEV represents a new and distinct viral strain. Phylogenetic evidence that avian HEV is the most divergent strain of HEV identified thus far and represents a new genotype.

EXAMPLE 13

Isolation of Avian HEV in Embryonated Chicken Eggs

Others have failed to isolate the agent associated with HS syndrome in chicken embryos with conventional routes of egg inoculation (H. L. Shivaprasad et al., "Necrohemorrhagic hepatitis in broiler breeders," Proc. Western Poult. Dis. Conf., p. 6, Sacramento, Calif. (1995)). Previous studies in pigs and primates showed that the I.V. route of inoculation is the most sensitive method to infect animals with the hepatitis E virus (HEV) (P. G. Kasorndorkbua et al., "Use of a swine bioassay and a RT-PCR assay to assess the risk of transmission of swine hepatitis E virus in pigs," J. Virol. Methods, In Press (2001); P. G. Halbur et al., "Comparative pathogenesis of infection of pigs with hepatitis E viruses recovered from a pig and a human," J. Clin. Microbiol. 39:918-923 (2001); X. J. Meng et al., "Experimental infection of pigs with the newly identified swine hepatitis E virus (swine HEV), but not with human strains of HEV," Arch. Virol. 143:1405-1415 (1998); X. J. Meng et al., "Genetic and experimental evidence for cross-species infection by the swine hepatitis E virus," J. Virol. 72:9714-9721 (1998)).

Surprisingly, the present attempt to isolate the agent associated with HS syndrome by I.V. inoculation of embryonated eggs was successful. A sample of bile collected from a 42-week-old Leghorn chicken with HS syndrome in California was used as the virus source (G. Haqshenas et al., "Genetic identification and characterization of a novel virus related to the human hepatitis E virus from chickens with Hepatitis-Splenomegaly Syndrome in the United States," J. Gen. Virol. 82:2449-2462 (2001)). The undiluted positive bile contained about $10^7$ genomic equivalents (GE) of avian HEV per ml measured by an avian HEV-specific semi-quantitative PCR (id.). Specific-pathogen-free (SPF) eggs were purchased at 1 day of embryonated age (Charles River SPAFAS, Inc. North Franklin, Conn.). At 9 days of embryonated age, 40 eggs were I.V.-inoculated with 100 µl of a $10^{-4}$ dilution of the original positive bile, and 20 eggs remain uninoculated as controls. On the day of natural hatching (21 days of embryonated age), half of the inoculated embryos were sacrificed, and bile and samples of liver and spleen were harvested. The other half of the inoculated embryos were allowed to hatch, and most of the hatched chickens were necropsied at 2 to 3 days of age. Bile and liver collected from the necropsied embryos and chickens were tested positive for avian HEV RNA. The titer of virus in the bile recovered from inoculated embryos was about $10^6$ GE/ml, indicating that avian HEV replicates in embryonated chicken eggs. Four hatched chickens were monitored continuously. The hatched chickens seroconverted to anti-HEV, and avian HEV shed in feces. The feces collected from a hatched chicken at 8 days of age contain about $10^5$ to $10^6$ GE/ml of 10% fecal suspension, and this was the source of avian HEV for the subsequent animal studies.

EXAMPLE 14

Experimental Infection of Young SPF Chickens with Avian HEV

As a first step to determine if chickens can be infected experimentally with avian HEV, 12 SPF chickens of 3-to-6 days of age were I.V.-inoculated, each with about $2\times10^4$ GE/ml of avian HEV. Two uninoculated chickens were kept in the same cage with the inoculated ones as contact controls. Eight uninoculated chickens housed in a separate room served as negative controls. Fecal swabs were collected from all chickens every 3 days and tested for avian HEV RNA. Weekly sera from all chickens were tested for anti-HEV antibodies. Avian HEV RNA was detected in the feces of all inoculated chickens but not of the controls. Fecal shedding of avian HEV lasted about 2 to 3 weeks from 9 to 28 days post-inoculation (DPI). As expected with a fecal-orally transmitted virus, the two uninoculated contact control chickens (housed in the same cage with the inoculated ones) also became infected, and fecal virus shedding in the two contact control chickens started late from 18 to 35 DPI. Seroconversion to anti-HEV antibodies in inoculated chickens (but not in controls) occurred at about 32 to 38 DPI. Two infected and two control chickens were necropsied each at 25 and 35 DPI. The biles and feces of the necropsied chickens were positive for avian HEV RNA. There were no significant gross lesions in the infected young chickens. Microscopic liver lesions in infected chickens (but not in controls) were characterized by lymphoplasmacytic hepatitis with moderate to severe periportal, perivascular/vascular and occasional random foci of infiltration of lymphocytes mixed with a few plasma cells. The results demonstrate the successful reproduction of avian HEV infection in young chickens of 3-to-6 days of age but not the full-spectrum of HS syndrome.

EXAMPLE 15

Experimental Reproduction of Avian HEV Infection and HS Syndrome in Leghorn SPF Layer Chickens and Broiler Breeder Chickens The failure to reproduce the full-spectrum of HS syndrome in young chickens is not surprising since, under field conditions, only broiler breeder and laying hens of 30-72 weeks of age developed HS syndrome (H. L. Shivaprasad et al., "Necrohemorrhagic hepatitis in broiler breeders," Proc. Western Poult. Dis. Conf., p. 6, Sacramento, Calif. (1995); C. Riddell, "Hepatitis-splenomegaly syndrome," DISEASE OF POULTRY, p. 1041 (1997)); S. J. Ritchie et al., "Hepatitis-splenomegaly" syndrome in commercial egg laying hens," Can. Vet. J. 32:500-501(1991)). Thus, two additional studies were performed to determine if avian HEV infection and HS syndrome could be experimentally reproduced in SPF layer chickens and broiler breeder chickens.

Layer chickens: Twenty (20) Leghorn SPF layer chickens of 60 weeks of age were purchased from Charles River SPAFAS, Inc. North Franklin, Conn. Ten chickens were I.V.-inoculated each with $10^4$ GE/ml of avian HEV, and housed in 5 isolators of 2 chickens each. Another 10 chickens, kept in 5 isolators in a separate room, were uninoculated as negative controls. Fecal swabs were collected from all chickens every 4 days. Avian HEV RNA was detected by RT-PCR from 8 to 27 DPIs in feces of infected chickens but not of controls. Sera were collected every 10 days, and seroconversion to anti-HEV antibodies occurred as early as 20 DPI. Two infected and two control chickens were necropsied each at 13, 17 and 21 DPIs. Avian HEV RNA was detected in the biles and feces of necropsied inoculated chickens but not of controls. Gross lesions characteristic of HS syndrome were observed in infected chickens, including hepatomegaly, subcapsular hemorrhages in livers (FIG. 18B) and pale foci on splenic capsular. Ovarian regression was also noticed in some infected chickens.

Figure 19A:
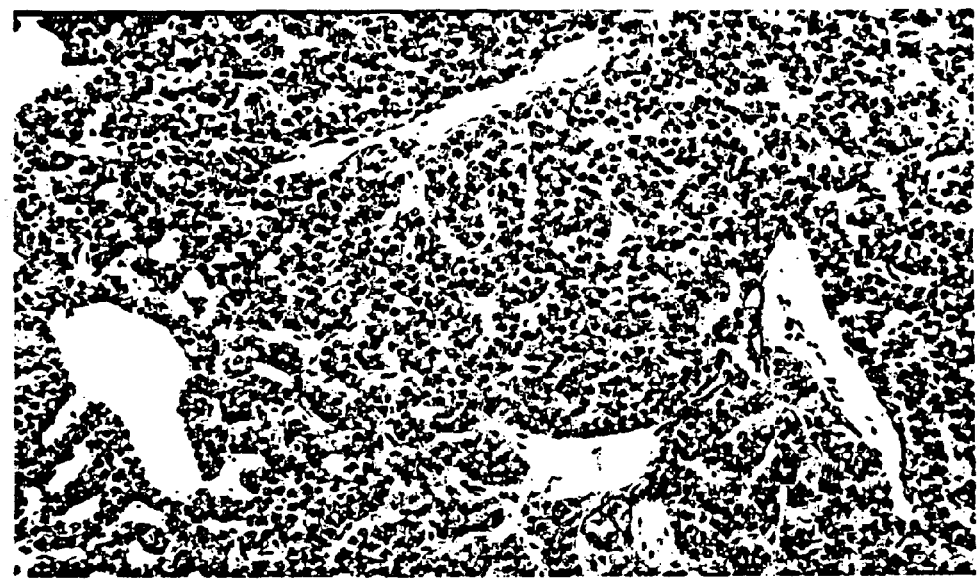
FIG. 19A (upper panel) shows a liver section from an uninoculated control SPF layer chicken. Note the lack of inflammatory cells anywhere in the section.
Figure 19B:
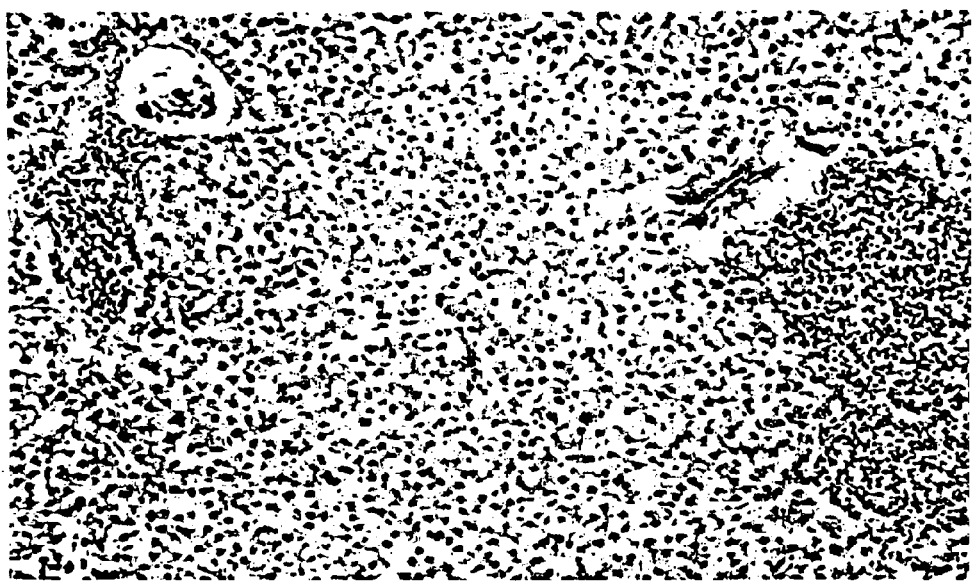
FIG. 19B (lower panel) shows a liver section from a SPF layer chicken experimentally infected with avian HEV (hematoxylin-eosin (HE) staining). Note the infiltration of lymphocytes in the periportal and perivascular regions.

Significant microscopic lesions of liver and spleen consistent with HS syndrome were observed in infected SPF layer chickens. Livers from infected chickens had lymphoplasmacytic hepatitis with mild to moderate infiltration of lymphocytes in the periportal and perivascular regions (FIG. 19B). There were also foci of lymphocytes randomly scattered throughout the liver. A few focal hepatocellular necrosis with lymphocyte infiltration was also observed. Spleens from infected chickens had a mild increase in mononuclear phagocytic system (MPS) cells. No significant gross or microscopic lesions were seen in control chickens.

Broiler breeder chickens: Six broiler breeder chickens of 64 weeks of age were I.V.-inoculated each with $10^4$ GE/ml of avian HEV. Another 6 chickens were uninoculated as controls. Fecal swabs were collected every 4 days, and avian HEV RNA was detected in feces of all inoculated chickens from 12 to 27 DPI but not from controls. Sera were collected every 10 days and, like SPF layer chickens, seroconversion to anti-HEV antibodies also occurred in broiler breeder chickens as early as 20 DPI. Two infected and two control chickens were each necropsied at 14 and 21 DPI. Like layer chickens, the infected broiler breeders also had gross lesions consistent with HS syndrome including swollen liver and hemorrhages in the live and spleen. Microscopic liver lesions were characterized by lymphoplasmacytic hepatitis with infiltration of lymphocytes in the periportal and perivascular regions, and mild to severe vacuolation of most hepatocytes. Sections of spleens had a mild increase in MPS cells. No significant gross or microscopic lesions were observed in controls.

These two studies demonstrate the successful reproduction of avian HEV infection and HS syndrome with characteristic gross and microscopic lesions in SPF layers and broiler breeder chickens. Avian HEV with a sequence identical to the virus in the inoculum was re-isolated from experimentally infected chickens. Thus, avian HEV as a causative agent of HS syndrome in chickens is confirmed in accordance with Koch's germ theory of disease (Koch, R., 1876, Untersuchungen ueber Bakterien V. Die Aetiologie der Milzbrand-Krankheit, begruendent auf die Entwicklungsgeschichte des Bacillus Anthracis. Beitr. z. Biol. D. Pflanzen 2: 277-310, In Milestones in Microbiology: 1556 to 1940, translated and edited by Thomas D. Brock, ASM Press. 1998, p. 89).

EXAMPLE 16

Evaluation of Field Isolates of Avian HEV from Chickens with HS Syndrome

Strains of human and swine HEVs are genetically heterogenic. To determine the extent of heterogeneity among avian HEV isolates, the helicase gene region of 8 additional avian HEV isolates from chickens with HS syndrome from different geographic regions of the U.S. was amplified by RT-PCR and sequenced (Table 4, below), showing that field isolates of avian HEV from chickens with HS syndrome are heterogeneic. Sequence and phylogenetic analyses revealed that, like swine and human HEVs, avian HEV isolates identified from different geographic regions of the United States are also heterogeneic (FIG. 20). Avian HEV isolates shared 79 to 96% nucleotide sequence identities with each other, 76-80% nucleotide sequence identities with BLSV and about 60% identities with swine and human HEVs (Table 4, below). The data also suggested that the BLS disease in Australian chickens and the HS syndrome in North American chickens are caused by a similar virus with about 76-80% sequence identities.

TABLE 4

Pairwise comparison of the nucleotide sequences of the helicase gene region of 8 field isolates of avian HEV (shown in boldface) identified from chickens with HS syndrome in the U.S. with that of other selected HEV strains

| | 2966G | 0242 | 4449 | 4090 | 3690 | 3158.5 | 3077 | 9318B | aHEV | BLSV | T1 | Mexico | US2 | Swine | Sar-55 | Flock location | Year Isol. |
|---|---|---|---|---|---|---|---|---|---|---|---|---|---|---|---|---|---|
| 2966G | | 83 | 81 | 79 | 81 | 98 | 79 | 96 | 86 | 77 | 56 | 60 | 59 | 59 | 61 | WI | 2000 |
| 0242 | 83 | | 88 | 86 | 83 | 83 | 86 | 83 | 80 | 79 | 56 | 59 | 59 | 60 | 59 | CA | 1994 |
| 4449 | 81 | 88 | | 96 | 84 | 83 | 96 | 82 | 80 | 77 | 56 | 60 | 60 | 60 | 59 | NY | 2000 |
| 4090 | 79 | 86 | 96 | | 83 | 80 | 94 | 81 | 79 | 76 | 56 | 60 | 59 | 59 | 59 | East coast | 2000 |
| 3690 | 81 | 83 | 84 | 83 | | 81 | 84 | 80 | 80 | 80 | 57 | 60 | 59 | 60 | 59 | CT | 2000 |
| 3158.5 | 98 | 83 | 83 | 80 | 81 | | 80 | 96 | 86 | 78 | 57 | 61 | 59 | 60 | 61 | CA | 1997 |
| 3077 | 79 | 86 | 96 | 94 | 84 | 80 | | 81 | 79 | 77 | 56 | 60 | 60 | 60 | 59 | CA | 1993 |
| 9318B | 96 | 83 | 82 | 81 | 80 | 96 | 81 | | 88 | 78 | 57 | 60 | 59 | 59 | 60 | Midwest | 2000 |
| aHEV* | 86 | 80 | 80 | 79 | 80 | 86 | 79 | 88 | | 77 | 57 | 61 | 57 | 58 | 60 | CA | 1993 |
| BLSV† | 77 | 79 | 77 | 76 | 80 | 78 | 77 | 78 | 77 | | 56 | 59 | 60 | 60 | 59 | | |
| T1 | 56 | 56 | 56 | 56 | 57 | 57 | 56 | 57 | 57 | 56 | | 73 | 75 | 75 | 76 | | |
| Mexico | 60 | 59 | 60 | 60 | 60 | 61 | 60 | 60 | 61 | 59 | 73 | | 72 | 75 | 78 | | |
| US2 | 59 | 59 | 60 | 59 | 59 | 59 | 60 | 59 | 57 | 60 | 75 | 72 | | 91 | 75 | | |
| Swine‡ | 59 | 60 | 60 | 59 | 60 | 60 | 60 | 59 | 58 | 60 | 75 | 75 | 91 | | 75 | | |
| Sar-55¶ | 61 | 59 | 59 | 59 | 59 | 61 | 59 | 60 | 60 | 59 | 76 | 78 | 75 | 75 | | | |

*aHEV, the prototype avian HEV.
†BLSV, the causative agent of BLS disease in Australian chickens.
‡Swine, the prototype U.S. swine HEV.
¶Sar-55, the Pakistani strain of human HEV.

EXAMPLE 17

Expression and Purification of the Truncated ORF2 Capsid Protein of Avian HEV in a Bacterial Expression System The truncated ORF2 protein of avian HEV containing the C-terminal 268 amino acid residues of ORF2 was expressed and characterized. The 804 bp sequence of the C-terminus of the avian HEV ORF2 was amplified with a set of avian HEV-specific primers: a sense primer (5'-GGG GGATCCAGTACATGTACGGCCGGCCTG-3', which corresponds to SEQ ID NO:10) with an introduced BamHI site (underlined), and an antisense primer (5'-GGG GAATTCTTAGGGTGGTGAGGGGAATG-3', which corresponds to SEQ ID NO:11) with an introduced EcoRI site (underlined). The BamHI and EcoRI sites were introduced at the 5' ends of the sense and antisense primers, respectively, to facilitate subsequent cloning steps. Proofreading Pfu DNA polymerase (Stratagene, La Jolla, Calif.) was used for PCR amplification of the fragment. The obtained PCR amplified fragment was purified and digested with BamHI and EcoRI restriction enzymes and cloned into the pRSET-C expression vector (Clontech Laboratories, Inc., Palo Alta, Calif.). The truncated ORF2 gene was in-frame with the coding sequence of the Xpress™ epitope (Invitrogen Corporation, Carlsbad, Calif.) located upstream of the multiple-cloning site of the expression vector. *E. coli* DH5α cells were transformed with the recombinant plasmids. The recombinant expression vector was isolated with a Qiagen Plasmid Mini Kit (Qiagen Inc., Valencia, Calif.), and confirmed by restriction enzyme digestions and DNA sequencing.

The recombinant plasmids were transformed into BL21 (DE3)pLysS competent cells that have been engineered to produce T7 RNA polymerase. Expression of the fusion protein was driven by a T7 promoter sequence upstream of the Xpress™ epitope sequence (Invitrogen Corporation, Carlsbad, Calif.). By using pRSET-C vector, the recombinant fusion protein is tagged by six tandem histidine residues at the amino terminus (N-terminus) that have a high affinity for ProBond™ resin (Invitrogen Corporation, Carlsbad, Calif.). The bacterial cells were grown in SOB broth containing 50 μg/ml of ampicillin and 25 μg/ml of chloramphenicol. Expression of the fusion protein was induced by the addition of 1 mM isopropyl-beta-D-thiogalactopyranoside (IPTG) for 4-5 hrs at 37° C. The fusion protein was expressed in *E. coli* strain BL21(DE3)pLysS as inclusion bodies. To confirm that the over-expressed protein contains Xpress™ epitope (Invitrogen Corporation, Carlsbad, Calif.), the crude bacterial lysates separated on a 12% polyacrylamide gel containing 0.1% SDS and transferred onto a nitrocellulose membrane (Osmonics, Inc., Minnetonka, Minn.). The immobolized protein on the membrane was incubated with a with horseradish peroxidase (HRP)-conjugated monoclonal antibody, known to be against Xpress™ epitope (Invitrogen Corporation, Carlsbad, Calif.) at 1:5,000 dilution. The immunocomplexes were detected using 4-chloro-1-naphthol (Sigma, St. Louis, Mo.).

From 50 ml of bacterial cultures, the fusion protein was purified by the use of ProBond™ Purification System (Invitrogen Corporation, Carlsbad, Calif.) based on the affinity of ProBond™ resin for His-tagged recombinant fusion protein. Bacterial cells were lysed with guanidinium lysis buffer (6 M guanidine hydrochloride, 20 mM sodium phosphate, 500 mM sodium chloride, pH 7.8) and insoluble debris was clarified by centrifugation at 3,000 g for 10 minutes at 4° C. The supernatant was added to the resin pre-equilibrated with the binding buffer and gently agitated for 10 minutes at room temperature to allow the fusion protein to bind the resin. The protein-bound resin was serially washed six times with denaturing binding buffer (8 M urea, 20 mM sodium phosphate, 500 mM sodium chloride) twice at each pH of 7.8, 6.0 and 5.3. The fusion protein was eluted in the elution buffer containing 8 M urea, 20 mM sodium phosphate and 500 mM sodium chloride (pH 4.0). The fractions containing the highest concentrations of protein were determined by the use of Bio-Rad protein assay reagent (BioRad, Carlsbad, Calif.). Five micrograms of the purified protein was analyzed by SDS-PAGE. The purified fusion protein hybridized with the MAb against Xpress™ epitope (Invitrogen Corporation, Carlsbad, Calif.).

The nucleotide sequence of the insert was confirmed by automated cycle sequencing. The recombinant plasmid containing the truncated ORF2 gene of avian HEV was transformed into *E.* coli strain BL21(DE3)pLysS. Upon induction with IPTG, the truncated ORF2 capsid protein of avian HEV was expressed in this bacterial strain with a very high yield. The expressed protein was observed on the gel at the size of about 32 kD (FIG. 21A). Samples taken at different time points revealed that the maximum expression occurred at about 4 to 5 hrs after induction with IPTG (FIG. 21A). Western blot analysis using a monoclonal antibody against Xpress™ epitope (Invitrogen Corporation, Carlsbad, Calif.) of the fusion protein confirmed the expression of the avian HEV ORF2 protein (FIG. 21B). Although the bacterial cells used in this study contain pLysS plasmid to minimize the background protein expressions, background expression was still observed. The fusion protein was expressed as inclusion bodies in the bacterial cells and was shown to be insoluble. The protein purification method was very efficient and about 6 mg of protein were obtained from 50 ml of the bacterial culture.

EXAMPLE 18

Evaluation of Antigenic Epitopes of Capsid Protein of Avian HEV, Human HEV, Swine HEV and Australian Chicken BLSV In Western blot analysis, the purified truncated ORF2 protein of avian HEV reacted with the antiserum obtained from chickens experimentally infected with avian HEV but not with sera from normal control chickens. To prepare antiserum against avian HEV, specific-pathogen-free (SPF) chickens (SPAFAS Inc.) were inoculated intravenously with a diluted bile sample containing $10^3$ GE/ml of avian HEV. The inoculated chickens excreted avian HEV in the feces and seroconverted to avian HEV antibodies. The convalescent sera collected at 30 days post inoculation were used as the avian HEV antiseum in this experiment. The antiserum against Sar-55 strain of human HEV was prepared by immunizing SPF pigs with baculovirus expressed and HPLC-purified capsid protein of the Sar-55 HEV. The antisera against swine HEV and US2 strain of human HEV were convalescent sera from pigs experimentally co-infected with these two HEV strains. The antiserum against Australia chicken BLSV was also kindly provided by Dr. Christine Payne (Murdoch University, Australia). The putative capsid protein of human HEV Sar-55 and swine HEV were expressed in baculovirus systems as described herein. The recombinant proteins were a gift from Drs Robert Purcell and Suzanne Emerson (NIH, Bethesda, Md.). The HPLC-purified recombinant ORF2 capsid proteins of human HEV Sar-55 and swine HEV were used in this study.

Western blot analyses were used to determine if the truncated ORF2 protein of avian HEV shares antigenic epitopes with that of human HEV, swine HEV and BLSV. The purified recombinant truncated ORF2 protein (250 ng/lane) of avian HEV was separated by SDS-PAGE and transferred onto a nitrocellulose membrane. The blots were cut into separate strips and then blocked in blocking solution (20 mM Tris-Cl, 500 mM NaCl, pH 7.5) containing 2% bovine serum albumin (BSA) for 1 hour. The strips were then incubated overnight at room temperature with 1:100 dilutions of antisera against avian HEV, swine HEV, human HEV and BLSV in Tris-buffered saline (20 mM Tris-Cl, 500 mM NaCl, pH 7.5)

(TBS) containing 0.05% Tween® 20 (polysorbate 20, commercially available from Mallinckrodt Baker, Inc., Phillipsburg, N.J.) (TBST) and 2% BSA. The original purified antibody against BLSV was diluted 1:1000 in TBST. Dilutions 1:100 of preinoculation swine sera were used as the negative controls. The strips were washed 2 times with TBST and once with TBS. Following 3 hrs incubation with HRP-conjugated goat anti-swine IgG (1:2000, Research Diagnostics Inc., Flanders, N.J.) and HRP-conjugated rabbit anti-chicken IgY (1:2000, Sigma, St. Louis, Mo.), the strips were washed as described above and the immunocomplexes were detected using 4-chloro-1-naphthol.

To further confirm the cross-reactivity between avian, swine and human HEVs, approximately 250 ng of HPLC purified recombinant capsid proteins of swine HEV and Sar-55 human HEV were separated by SDS-PAGE and blotted onto a nitrocellulose membrane. The blot was incubated with antisera against avian HEV, swine HEV and human HEV. Serum dilutions, incubation and washing steps were carried out as described above. Anti-chicken IgY conjugated with HRP was used as the secondary antibody as described above.

Figure 22A:
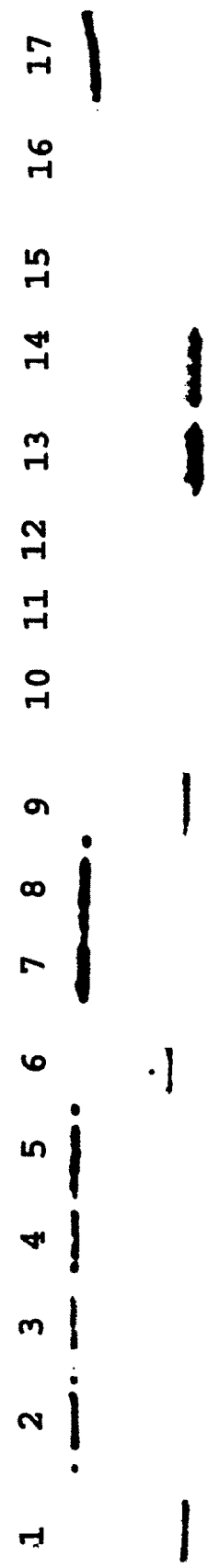
FIG. 22A illustrates Western blot analyses of antigenic cross-reactivity of avian HEV, swine HEV, human HEV and BLSV. Purified recombinant proteins of truncated avian HEV ORF2 (Lanes 1, 6, 9, 12-15), swine HEV ORF2 (Lanes 2, 5, 8, 11, 16) and Sar-55 human HEV ORF2 (Lanes 3, 4, 7, 10, 17) were separated by SDS PAGE, transferred onto a nitrocellulose membrane and incubated with antibodies against swine HEV (Lanes 1-3), US2 human HEV (Lanes 4-6), Sar-55 human HEV (Lanes 7-9), avian HEV (Lanes 13, 16-17), and BLSV (Lane 14). Each lane contains about 250 ng of recombinant proteins. The sera were diluted 1:100 in blocking solution before added to the membranes. The development step was stopped as soon as the signal related to the preinoculation ("preimmune") sera started to appear. Preinoculation pig (Lanes 10-12) and chicken sera (Lane 15) were used as negative controls.
Figures 22B, 22C:
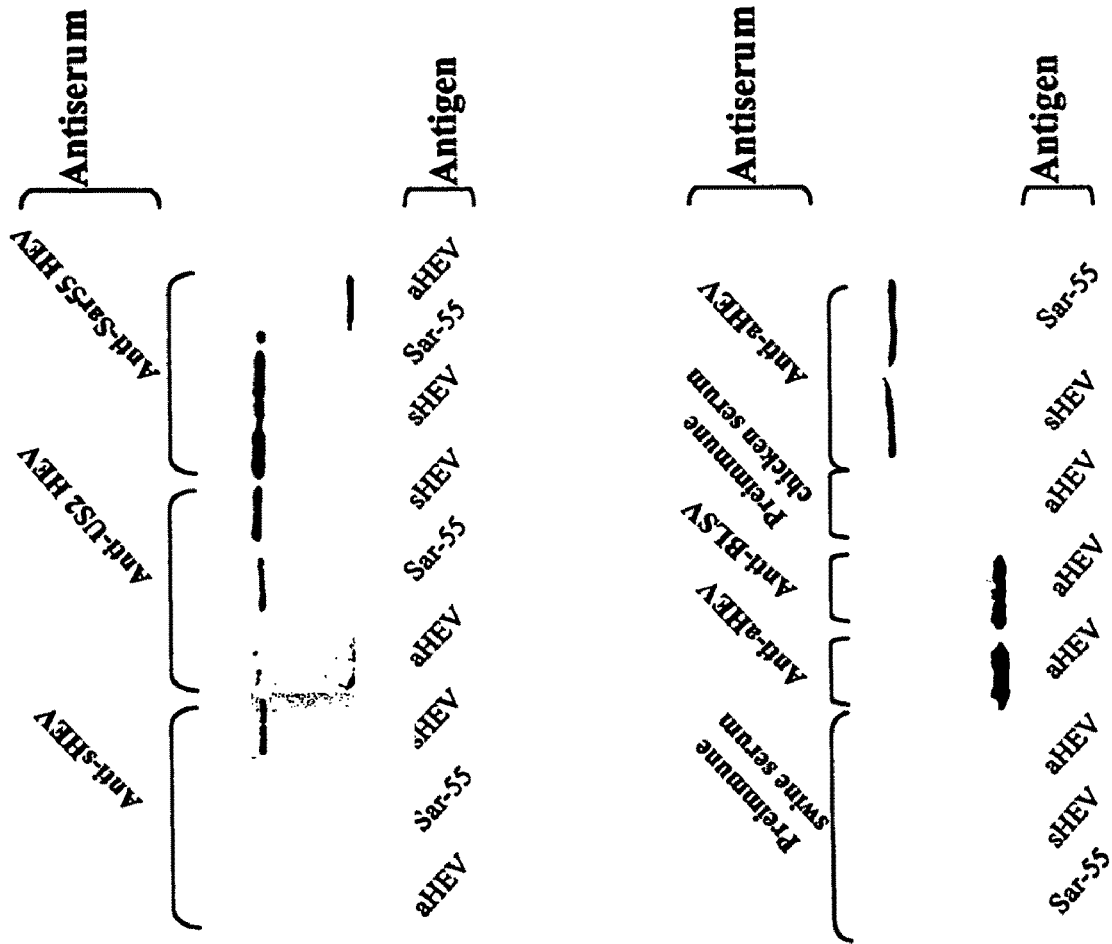
FIGS. 22B and 22C present the same data in a comparative format.

The purified truncated ORF2 protein of avian HEV reacted strongly in Western blot analyses with convalescent sera from SPF chickens experimentally infected with avian HEV, HEV antibodies (antisera) raised against the capsid protein of Sar-55 human HEV and convalescent sera against the US2 strain of human HEV and swine HEV, and the antiserum against the Australian chicken BLSV (FIGS. 22A and 22B). The purified truncated avian HEV ORF2 protein did not react with the preinoculation control chicken sera. Convalescent antisera from chickens experimentally infected with avian HEV reacted with the HPLC-purified recombinant ORF2 protein of Sar-55 human HEV. Swine HEV antiserum reacted strongly with the recombinant swine HEV ORF2 antigen. The US2 and Sar-55 human HEV antisera reacted with the recombinant swine HEV ORF2 capsid protein. The Sar-55 human HEV antiserum reacted strongly with Sar-55 ORF2 capsid antigen, but to a lesser extent with heterologous antisera against swine and avian HEVs (FIGS. 22A and 22B). The reaction signals between avian HEV antiserum, Sar-55 human HEV and swine HEV ORF2 proteins were also strong. These results showed that avian HEV shares antigenic epitopes in its ORF2 capsid protein with swine and human HEVs as well as BLSV.

EXAMPLE 19

Cross-Reactivity of Avian HEV, Swine HEV and Human HEV Using ELISA

To assess the cross-reactivity of avian HEV, swine HEV and human HEV under a different condition than above study, this experiment was conducted. The ELISA plates (commercially available from Viral Antigens, Inc., Memphis, Tenn.; BD Biosciences, Bedford, Mass. and others) were coated for 2 hrs with recombinant avian HEV, swine HEV and human HEV capsid antigens at 37° C. Each antigen was used at a concentration of 2 μg/ml of sodium carbonate buffer, pH 9.6. The potential non-specific binding sites were blocked with blocking solution (10% fetal bovine serum and 0.5% gelatin in washing buffer). The antisera, used in Western blot analyses, were diluted 1/200 in blocking solution. The preinoculation sera from a pig and a chicken were used as the negative controls. Following 30 minutes incubation at 37° C., the plates were washed 4 times with washing solution (PBS containing 0.05% Tween® 20 (polysorbate 20, commercially available from Mallinckrodt Baker, Inc., Phillipsburg, N.J.), pH 7.4). The HRP-conjugated secondary antibodies were used as described for Western blot analysis. Following 30 minutes incubation at 37° C., the plates were washed as described above and the antigen-antibody complexes were detected using 2,2'-Azino-bis (3-ethylbenthiazoline-6-sulfonic acid). After 10 minutes incubation at room temperature, the optical density (OD) was measured at 405 nm.

Figure 23:
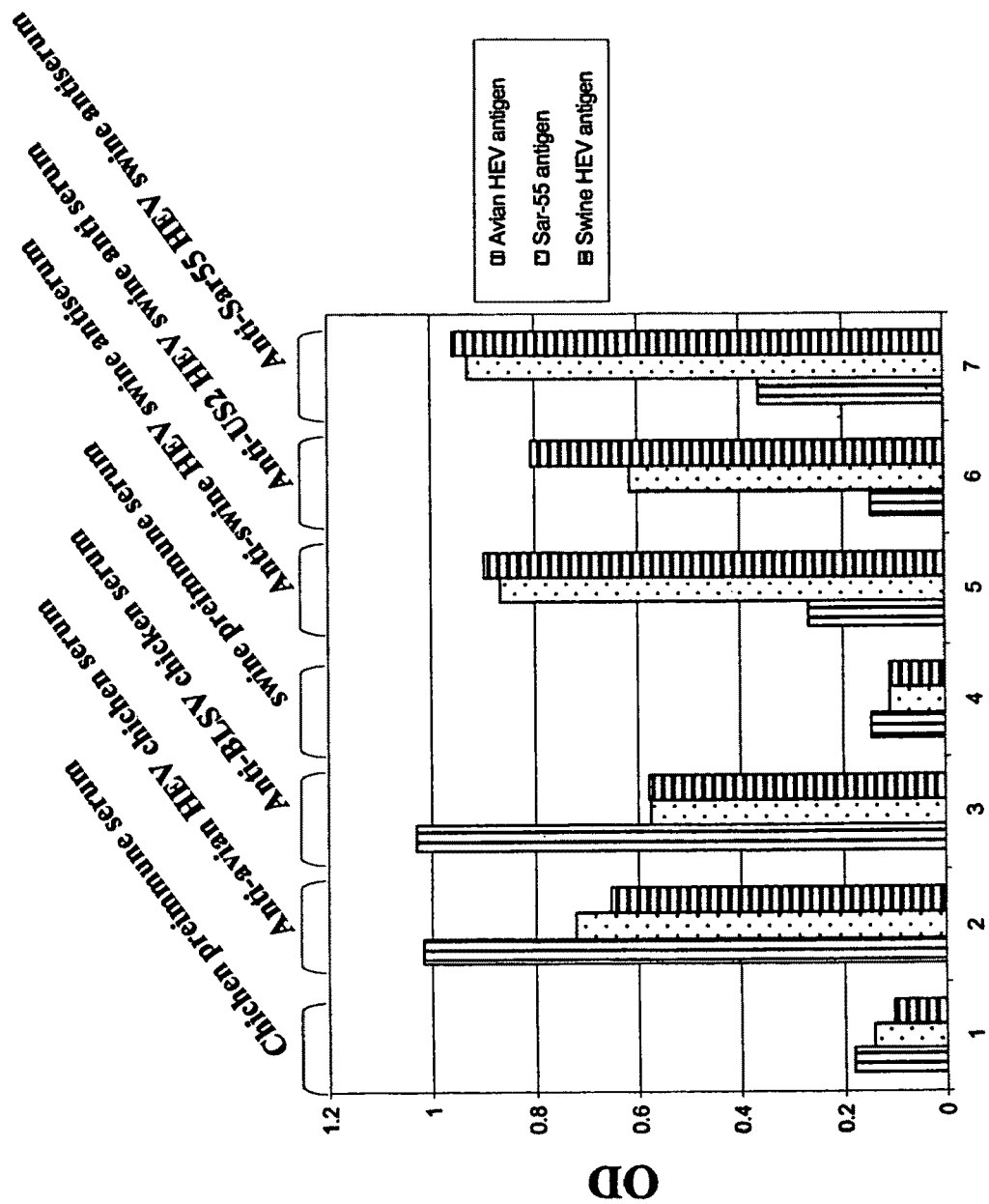
FIG. 23 illustrates the ELISA results generated from cross-reactivity of different antigens with different antisera and measured by optical density ("OD").

The cross-reactivity of avian HEV, swine HEV and human HEV were further confirmed using ELISA. As can be seen from FIG. 23, each antiserum strongly reacted with the corresponding antigen. The OD generated by interaction of avian HEV antiserum against recombinant antigens of Sar-55 human HEV strain and swine HEV was as high as 0.722 and 0.655, respectively, while the OD indicating non-specific binding of preinoculation ("preimmune") chicken serum remained as low as 0.142 and 0.103, respectively. The OD values obtained from cross-reacting of avian HEV antigen to antiserum against Sar-55 human HEV was almost twice the OD recorded when the preinoculation pig serum was used. The OD obtained from reaction of US2 human HEV almost did not differ from the OD obtained for the preinoculation serum.

EXAMPLE 20

Computer Analysis of Amino Acid Sequences

The predicted amino acid sequences of the truncated ORF2 protein of avian, swine and human HEV strains were compared with MacVector® program (Oxford Molecular, Inc., Madison, Wis.). Hydropathy and antigenic plots of the amino acid sequences were determined according to Kyte-Doolittle (J. Kyte & R. F. Doolittle, "A simple method for displaying the hydropathic character of a protein," J. Mol. Biol. 157:105-32 (1982)) and Welling (Welling et al., "Prediction of sequential antigenic regions in proteins," FEBS Letters 188:215-18 (1985)) methods using the MacVector® computer program (Oxford Molecular, Inc., Madison, Wis.).

Analyses of the predicted amino acid sequences of the entire ORF2 revealed that avian HEV shares only about 38% amino acid sequence identities with swine, US2 and Sar-55 HEV strains. Swine HEV ORF2 shared about 98% and 91% amino acid identities with US2 and Sar-55 HEV strains, respectively. The ORF2 of Sar-55 human HEV shared 91% amino acid sequence identity with the US2 strain of human HEV. Amino acid sequence alignment of the truncated ORF2 protein of avian BEV with the corresponding regions of swine HEV, Sar-55 human HEV and US2 human HEV also revealed that the most conserved region of the truncated 267 amino acid sequence is located at its N-terminus (FIG. 24) which contains hydrophilic amino acid residues (FIGS. 25A-25D). By using the Welling method (Welling et al., 1985, supra) to predict antigenic domains of the protein, three antigenic regions located at amino acids 460-490, 556-566 and 590-600 were also hydrophilic (FIGS. 25A-25D).

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. An isolated, immunogenic protein encoded by the ORF2 gene of an avian hepatitis E virus set forth in SEQ ID NO:7 or its complementary strand.

2. The protein according to claim 1, wherein the protein comprises an ORF2 capsid protein of the avian hepatitis E virus.

3. An immunogenic composition comprising a nontoxic, physiologically acceptable carrier and an isolated protein encoded by the ORF2 gene of an avian hepatitis E virus set forth in SEQ ID NO:7 or its complementary strand.

4. A vaccine for protecting an avian species from hepatitis-splenomegaly syndrome caused by an avian hepatitis E virus comprising a nontoxic, physiologically acceptable carrier and an isolated protein encoded by the ORF2 gene of an avian hepatitis E virus set forth in SEQ ID NO:7 or its complementary strand.

5. The vaccine according to claim 4, wherein said vaccine further contains an adjuvant.

6. A method of protecting an avian species from hepatitis-splenomegaly syndrome caused by an avian hepatitis E virus comprising administering an immunologically effective amount of the vaccine according to claim 5 to said avian species.

7. The method according to claim 6, wherein the vaccine is administered to a chicken.

8. The method according to claim 6, wherein the vaccine is administered orally, intrabuccally, intranasally, transdermally or parenterally.

* * * * *

SEQUENCE LISTING

<160> NUMBER OF SEQ ID NOS: 25

<210> SEQ ID NO 1
<211> LENGTH: 3946
<212> TYPE: DNA
<213> ORGANISM: Hepatitis E virus

<400> SEQUENCE: 1

| | | | | | | |
|---|---|---|---|---|---|---|
| accagcattg | gatttcgatg | gacgctgttt | aacgagcgcc | gttgatcttg | ggttgcagcc | 60 |
| taccagctgg | cgcaccgtat | cccaccgttg | cccttgggac | gtttgtatat | ttttgcgtac | 120 |
| tgattatccg | actatcacca | caaccagtag | ggtgctgcgg | tctgttgtgt | ttaccggtga | 180 |
| aaccattggt | cagaagatag | tgtttaccca | ggtggccaag | cagtcgaacc | ccgggtccat | 240 |
| aacggtccat | gaggcgcagg | gcagtacttt | tgatcagact | actataatcg | ccacgttaga | 300 |
| tgctcgtggc | cttatagctt | catctcgcgc | gcatgccata | gttgcgctaa | cccgccaccg | 360 |
| ggagcgctgt | agtgtgattg | atgttggtgg | ggtgctggtc | gagattggag | ttactgatgc | 420 |
| catgtttaac | aatatcgaaa | tgcagcttgt | gcgacctgat | gctgcagccc | ctgccggggt | 480 |
| gctacgagcc | ccagacgaca | ccgtggatgg | cttgttggac | ataccccgg | cccacactga | 540 |
| tgtagcggcg | gtgttaacag | ctgaggcgat | tgggcatgcg | ccccttgaat | tggccgccat | 600 |
| aaatccaccc | gggcctgtat | tggagcaggg | cctattatac | atgccggcca | ggcttgatgg | 660 |
| gcgtgatgag | gttgttaagc | tccagctgtc | ggatactgta | cactgccgcc | tggctgcacc | 720 |
| cactagccgt | cttgcggtga | ttaacacatt | ggttgggcgg | tacggtaaag | ccactaagct | 780 |
| gcctgaggtt | gaatatgact | taatggacac | tattgcgcag | ttctggcatc | atatcggacc | 840 |
| aatcaacccc | tcaacactgg | agtatgcaga | gatgtgcgag | gccatgctta | gtaagggcca | 900 |
| ggatgggtcc | ttgattgtac | atctggattt | acaggatgct | gattgttctc | gcataacatt | 960 |
| cttccagaag | gactgcgcta | aatttacgct | ggatgaccct | gttgcacacg | gtaaagtggg | 1020 |
| acagggggata | tctgcgtggc | cgaaaacttt | tgtgcactt | ttcggcccct | ggttccgggc | 1080 |
| tatagagaag | caccttgtgg | ctgggttacc | cccaggttat | tactatgggg | acctgtacac | 1140 |
| ggaagccgat | ctgcatcgtt | ctgtgctttg | cgcgcctgct | ggtcaccttg | ttttgagaa | 1200 |
| tgatttctca | gagtttgact | caacgcagaa | taatgtgtcc | cttgatctcg | aatgtgaatt | 1260 |
| gatgcgcagg | tttgggatgc | ccgattggat | ggtagccttg | taccatcttg | ttcgatcata | 1320 |
| ctggctcttg | gttgccccga | agaagcccct | tcgtggctgt | tggaaaaaac | actctggtga | 1380 |
| gccgggcacc | cttttgtgga | atacagtttg | gaacatgact | gtgttgcatc | atgtttatga | 1440 |
| gtttgatcga | ccaagtgtgt | tgtgtttcaa | aggtgatgat | agtgtcgttg | tctgtgaatc | 1500 |
| ggtgcgcgcc | cgtccagagg | gcgttagtct | cgtggcagac | tgcgggctaa | aaatgaagga | 1560 |
| caagaccggc | ccgtgtggcg | cctttttccaa | cctgctgatc | ttcccgggag | ctggtgttgt | 1620 |
| ctgcgacctg | ttacggcagt | ggggccgctt | gactgacaag | aactgggggc | ccgacattca | 1680 |
| gcggatgcag | gaccttgagc | aagcgtgtaa | ggattttgtt | gcacgtgttg | taactcaggg | 1740 |
| taaagagatg | ttgaccatcc | agcttgtggc | gggttattat | ggtgtggaag | ttggtatggt | 1800 |
| tgaggtggtt | tgggggggctt | tgaaggcctg | cgccgcagcc | cgcgagaccc | tagtgaccaa | 1860 |
| caggttgccg | gtactaaact | tatctaagga | ggactgaaca | aataacaatc | attatgcagt | 1920 |
| ctgcgcgtcc | atgtgcctta | gctgccagtt | ctggtgtttg | gagtgccagg | aaagtggggt | 1980 |
| gggatgtcgc | tgtgtagatt | gttgctcatg | cttgcaatgt | gctgcggggt | gtcaagggc | 2040 |

-continued

```
tcccaaacgc tcccagccgg aggcaggcgt ggccagcgcc gccgtgacaa ttcagcccag    2100
tggagcactc aacaacgccc cgagggagcc gtcggccccg cccctctcac agacgttgtc    2160
accgcggcag gtactcgcac ggtaccagat gtagatcaag ccggtgccgt gctggtgcgc    2220
cagtataatc tagtgaccag cccgttaggc ctggccaccc ttggtagcac caatgccttg    2280
ctttatgccg caccggtgtc accgttaatg ccgcttcagg acggcacgac gtctaatatc    2340
atgagcacgg agtctagcaa ctatgctcaa taccgtgtac agggcctaac tgtccgctgg    2400
cgcccagttg tgccaaatgc ggtgggcggc ttctctataa gcatggccta ttggccccag    2460
acaacatcca cccctacaag cattgacatg aattccatca cgtccactga cgtccgtgtg    2520
gtgcttcagc cgggctctgc tggttttgctg actataccac atgagcgttt ggcgtataag    2580
aacaatggtt ggcggtccgt cgaaacggta ccgtcccac aggaggatgc cacgtccggc    2640
atgctcatgg tttgtgtcca cgggaccccc tggaatagtt ataccaatag tgtttacacc    2700
gggccgcttg gtatggttga ttttgccata aagttacagc taaggaactt gtcgcccggt    2760
aatacaaatg ccagggtcac ccgtgtgaag gtgacggccc acataccat caaggctgac    2820
ccatctggtg ctaccataac aacagcagct gcggccaggt ttatggcgga tgtgcgttgg    2880
ggcttgggca ctgctgagga tggcgaaatt ggtcacggca tccttggtgt tctgtttaac    2940
ctggcggaca cagttttagg tggccttgccc tcgacactgc tgcgggcggc gagtggtcag    3000
tacatgtacg gccggcctgt ggggaacgcg aacggcgagc tgaggtgaa actgtatatg    3060
tcggttgagg atgccgttaa cgataaacct attatggtcc cccatgacat cgacctcggg    3120
accagcactg tcacctgcca ggactatggg aatcagcatg tggatgaccg cccatccccg    3180
gccccggccc ctaagcgagc tttgggcacc ctaaggtcag gggatgtgtt gcgtattact    3240
ggctccatgc agtatgtgac taacgccgag ttgttaccgc agagtgtgtc acagggggtac    3300
tttggggccg gcagcaccat gatggtgcat aatttgatca ctggtgtgcg cgccccgcc    3360
agttcagtcg actggacgaa ggcaacagtg gatggggtcc aggtgaagac tgtcgatgct    3420
agttctggga gtaataggtt tgcagcgtta cctgcatttg gaaagccagc tgtgtggggg    3480
ccccagggcg ctgggtattt ctaccagtat aacagcaccc accaggagtg gatttatttt    3540
cttcagaatg gtagctccgt ggtttggtat gcatatacta atatgttggg ccagaagtca    3600
gatacatcca ttctttttga ggtccggcca atccaagcta gtgatcagcc ttggtttttg    3660
gcacaccaca ctggcggcga tgactgtacc acctgtctgc ctctgggggtt aagaacatgt    3720
tgccgccagg cgccagaaga ccagtcacct gagacgcgcc ggctcctaga ccggcttagt    3780
aggacattcc cctcaccacc ctaatgtcgt ggttttgggg ttttaggttg attttctgta    3840
tctgggcgta attgcccta tgtttaattt attgtgattt ttataactgt tcatttgatt    3900
atttatgaaa tcctcccatc tcgggcatag taaaaaaaaa aaaaaa              3946
```

<210> SEQ ID NO 2
<211> LENGTH: 146
<212> TYPE: PRT
<213> ORGANISM: Hepatitis E virus

<400> SEQUENCE: 2

Pro Ala Leu Asp Phe Asp Gly Arg Cys Leu Thr Ser Ala Val Asp Leu
1               5                   10                  15

Gly Leu Gln Pro Thr Ser Trp Arg Thr Val Ser His Arg Cys Pro Trp
            20                  25                  30

```
Asp Val Cys Ile Phe Leu Arg Thr Asp Tyr Pro Thr Ile Thr Thr Thr
            35                  40                  45

Ser Arg Val Leu Arg Ser Val Val Phe Thr Gly Glu Thr Ile Gly Gln
    50                  55                  60

Lys Ile Val Phe Thr Gln Val Ala Lys Gln Ser Asn Pro Gly Ser Ile
65                  70                  75                  80

Thr Val His Glu Ala Gln Gly Ser Thr Phe Asp Gln Thr Thr Ile Ile
                85                  90                  95

Ala Thr Leu Asp Ala Arg Gly Leu Ile Ala Ser Ser Arg Ala His Ala
            100                 105                 110

Ile Val Ala Leu Thr Arg His Arg Glu Arg Cys Ser Val Ile Asp Val
            115                 120                 125

Gly Gly Val Leu Val Glu Ile Gly Val Thr Asp Ala Met Phe Asn Asn
        130                 135                 140

Ile Glu
145

<210> SEQ ID NO 3
<211> LENGTH: 439
<212> TYPE: DNA
<213> ORGANISM: Hepatitis E virus

<400> SEQUENCE: 3
accagcattg gatttcgatg gacgctgttt aacgagcgcc gttgatcttg ggttgcagcc      60
taccagctgg cgcaccgtat cccaccgttg cccttgggac gtttgtatat ttttgcgtac    120
tgattatccg actatcacca caaccagtag ggtgctgcgg tctgttgtgt ttaccggtga    180
aaccattggt cagaagatag tgtttaccca ggtggccaag cagtcgaacc ccgggtccat    240
aacggtccat gaggcgcagg gcagtacttt tgatcagact actataatcg ccacgttaga    300
tgctcgtggc cttatagctt catctcgcgc gcatgccata gttgcgctaa cccgccaccg    360
ggagcgctgt agtgtgattg atgttggtgg ggtgctggtc gagattggag ttactgatgc    420
catgtttaac aatatcgaa                                                  439

<210> SEQ ID NO 4
<211> LENGTH: 483
<212> TYPE: PRT
<213> ORGANISM: Hepatitis E virus

<400> SEQUENCE: 4

Leu Val Arg Pro Asp Ala Ala Pro Ala Gly Val Leu Arg Ala Pro
1               5                   10                  15

Asp Asp Thr Val Asp Gly Leu Leu Asp Ile Pro Pro Ala His Thr Asp
            20                  25                  30

Val Ala Ala Val Leu Thr Ala Glu Ala Ile Gly His Ala Pro Leu Glu
            35                  40                  45

Leu Ala Ala Ile Asn Pro Pro Gly Pro Val Leu Glu Gln Gly Leu Leu
    50                  55                  60

Tyr Met Pro Ala Arg Leu Asp Gly Arg Asp Glu Val Val Lys Leu Gln
65                  70                  75                  80

Leu Ser Asp Thr Val His Cys Arg Leu Ala Ala Pro Thr Ser Arg Leu
                85                  90                  95

Ala Val Ile Asn Thr Leu Val Gly Arg Tyr Gly Lys Ala Thr Lys Leu
            100                 105                 110

Pro Glu Val Glu Tyr Asp Leu Met Asp Thr Ile Ala Gln Phe Trp His
            115                 120                 125
```

His Ile Gly Pro Ile Asn Pro Ser Thr Leu Glu Tyr Ala Glu Met Cys
    130                 135                 140

Glu Ala Met Leu Ser Lys Gly Gln Asp Gly Ser Leu Ile Val His Leu
145                 150                 155                 160

Asp Leu Gln Asp Ala Asp Cys Ser Arg Ile Thr Phe Phe Gln Lys Asp
                165                 170                 175

Cys Ala Lys Phe Thr Leu Asp Asp Pro Val Ala His Gly Lys Val Gly
            180                 185                 190

Gln Gly Ile Ser Ala Trp Pro Lys Thr Leu Cys Ala Leu Phe Gly Pro
        195                 200                 205

Trp Phe Arg Ala Ile Glu Lys His Leu Val Ala Gly Leu Pro Pro Gly
210                 215                 220

Tyr Tyr Tyr Gly Asp Leu Tyr Thr Glu Ala Asp Leu His Arg Ser Val
225                 230                 235                 240

Leu Cys Ala Pro Ala Gly His Leu Val Phe Glu Asn Asp Phe Ser Glu
                245                 250                 255

Phe Asp Ser Thr Gln Asn Asn Val Ser Leu Asp Leu Glu Cys Glu Leu
            260                 265                 270

Met Arg Arg Phe Gly Met Pro Asp Trp Met Val Ala Leu Tyr His Leu
        275                 280                 285

Val Arg Ser Tyr Trp Leu Leu Val Ala Pro Lys Glu Ala Leu Arg Gly
290                 295                 300

Cys Trp Lys Lys His Ser Gly Glu Pro Gly Thr Leu Leu Trp Asn Thr
305                 310                 315                 320

Val Trp Asn Met Thr Val Leu His His Val Tyr Glu Phe Asp Arg Pro
                325                 330                 335

Ser Val Leu Cys Phe Lys Gly Asp Asp Ser Val Val Cys Glu Ser
            340                 345                 350

Val Arg Ala Arg Pro Glu Gly Val Ser Leu Val Ala Asp Cys Gly Leu
        355                 360                 365

Lys Met Lys Asp Lys Thr Gly Pro Cys Gly Ala Phe Ser Asn Leu Leu
370                 375                 380

Ile Phe Pro Gly Ala Gly Val Val Cys Asp Leu Leu Arg Gln Trp Gly
385                 390                 395                 400

Arg Leu Thr Asp Lys Asn Trp Gly Pro Asp Ile Gln Arg Met Gln Asp
                405                 410                 415

Leu Glu Gln Ala Cys Lys Asp Phe Val Ala Arg Val Val Thr Gln Gly
            420                 425                 430

Lys Glu Met Leu Thr Ile Gln Leu Val Ala Gly Tyr Tyr Gly Val Glu
        435                 440                 445

Val Gly Met Val Glu Val Val Trp Gly Ala Leu Lys Ala Cys Ala Ala
450                 455                 460

Ala Arg Glu Thr Leu Val Thr Asn Arg Leu Pro Val Leu Asn Leu Ser
465                 470                 475                 480

Lys Glu Asp

<210> SEQ ID NO 5
<211> LENGTH: 1450
<212> TYPE: DNA
<213> ORGANISM: Hepatitis E virus

<400> SEQUENCE: 5
gcttgtgcga cctgatgctg cagcccctgc cggggtgcta cgagcccag acgacaccgt    60

```
ggatggcttg ttggacatac ccccggccca cactgatgta gcggcggtgt aacagctga    120 ggcgattggg catgcgcccc ttgaattggc cgccataaat ccacccgggc ctgtattgga    180
gcagggccta ttatacatgc cggccaggct tgatgggcgt gatgaggttg ttaagctcca    240
gctgtcggat actgtacact gccgcctggc tgcacccact agccgtcttg cggtgattaa    300
cacattggtt gggcggtacg gtaaagccac taagctgcct gaggttgaat atgacttaat    360
ggacactatt gcgcagttct ggcatcatat cggaccaatc aacccctcaa cactggagta    420
tgcagagatg tgcgaggcca tgcttagtaa gggccaggat gggtccttga ttgtacatct    480
ggatttacag gatgctgatt gttctcgcat aacattcttc cagaaggact gcgctaaatt    540
tacgctggat gaccctgttg cacacggtaa agtgggacag ggatatctg cgtggccgaa     600 aactttgtgt gcacttttcg gcccctggtt ccgggctata gaagcacc ttgtggctgg      660 gttaccccca ggttattact atggggacct gtacacggaa gccgatctgc atcgttctgt    720
gctttgcgcg cctgctggtc accttgtttt tgagaatgat ttctcagagt ttgactcaac    780
gcagaataat gtgtcccttg atctcgaatg tgaattgatg cgcaggtttg ggatgcccga    840
ttggatggta gccttgtacc atcttgttcg atcatactgg ctcttggttg ccccgaaaga    900
agcccttcgt ggctgttgga aaaaacactc tggtgagccg gcacccttt tgtggaatac     960 agtttggaac atgactgtgt tgcatcatgt ttatgagttt gatcgaccaa gtgtgttgtg   1020
tttcaaaggt gatgatagtg tcgttgtctg tgaatcggtg cgcgcccgtc cagagggcgt   1080
tagtctcgtg gcagactgcg ggctaaaaat gaaggacaag accggccgt gtggcgcctt    1140 ttccaacctg ctgatcttcc cgggagctgg tgttgtctgc gacctgttac ggcagtgggg   1200
ccgcttgact gacaagaact gggggcccga cattcagcgg atgcaggacc ttgagcaagc   1260
gtgtaaggat tttgttgcac gtgttgtaac tcagggtaaa gagatgttga ccatccagct   1320
tgtggcgggt tattatggtg tggaagttgg tatggttgag gtggtttggg gggctttgaa   1380
ggcctgcgcc gcagcccgcg agaccctagt gaccaacagg ttgccggtac taaacttatc   1440
taaggaggac                                                          1450
```

<210> SEQ ID NO 6
<211> LENGTH: 606
<212> TYPE: PRT
<213> ORGANISM: Hepatitis E virus

<400> SEQUENCE: 6

```
Met Ser Leu Cys Arg Leu Leu Met Leu Ala Met Cys Cys Gly Val
1               5                   10                  15

Ser Arg Gly Ser Gln Thr Leu Pro Ala Gly Gly Arg Gly Gln Arg
                20                  25                  30

Arg Arg Asp Asn Ser Ala Gln Trp Ser Thr Gln Gln Arg Pro Glu Gly
            35                  40                  45

Ala Val Gly Pro Ala Pro Leu Thr Asp Val Val Thr Ala Ala Gly Thr
        50                  55                  60

Arg Thr Val Pro Asp Val Asp Gln Ala Gly Ala Val Leu Val Arg Gln
65                  70                  75                  80

Tyr Asn Leu Val Thr Ser Pro Leu Gly Leu Ala Thr Leu Gly Ser Thr
                85                  90                  95

Asn Ala Leu Leu Tyr Ala Ala Pro Val Ser Pro Leu Met Pro Leu Gln
            100                 105                 110

Asp Gly Thr Thr Ser Asn Ile Met Ser Thr Glu Ser Ser Asn Tyr Ala
        115                 120                 125
```

```
Gln Tyr Arg Val Gln Gly Leu Thr Val Arg Trp Arg Pro Val Val Pro
    130                 135                 140

Asn Ala Val Gly Gly Phe Ser Ile Ser Met Ala Tyr Trp Pro Gln Thr
145                 150                 155                 160

Thr Ser Thr Pro Thr Ser Ile Asp Met Asn Ser Ile Ser Thr Thr Asp
                165                 170                 175

Val Arg Val Val Leu Gln Pro Gly Ser Ala Gly Leu Leu Thr Ile Pro
                180                 185                 190

His Glu Arg Leu Ala Tyr Lys Asn Asn Gly Trp Arg Ser Val Glu Thr
                195                 200                 205

Val Ser Val Pro Gln Glu Asp Ala Thr Ser Gly Met Leu Met Val Cys
    210                 215                 220

Val His Gly Thr Pro Trp Asn Ser Tyr Thr Asn Ser Val Tyr Thr Gly
225                 230                 235                 240

Pro Leu Gly Met Val Asp Phe Ala Ile Lys Leu Gln Leu Arg Asn Leu
                245                 250                 255

Ser Pro Gly Asn Thr Asn Ala Arg Val Thr Arg Val Lys Val Thr Ala
                260                 265                 270

Pro His Thr Ile Lys Ala Asp Pro Ser Gly Ala Thr Ile Thr Thr Ala
                275                 280                 285

Ala Ala Ala Arg Phe Met Ala Asp Val Arg Trp Gly Leu Gly Thr Ala
    290                 295                 300

Glu Asp Gly Glu Ile Gly His Gly Ile Leu Gly Val Leu Phe Asn Leu
305                 310                 315                 320

Ala Asp Thr Val Leu Gly Gly Leu Pro Ser Thr Leu Leu Arg Ala Ala
                325                 330                 335

Ser Gly Gln Tyr Met Tyr Gly Arg Pro Val Gly Asn Ala Asn Gly Glu
                340                 345                 350

Pro Glu Val Lys Leu Tyr Met Ser Val Glu Asp Ala Val Asn Asp Lys
                355                 360                 365

Pro Ile Met Val Pro His Asp Ile Asp Leu Gly Thr Ser Thr Val Thr
    370                 375                 380

Cys Gln Asp Tyr Gly Asn Gln His Val Asp Asp Arg Pro Ser Pro Ala
385                 390                 395                 400

Pro Ala Pro Lys Arg Ala Leu Gly Thr Leu Arg Ser Gly Asp Val Leu
                405                 410                 415

Arg Ile Thr Gly Ser Met Gln Tyr Val Thr Asn Ala Glu Leu Leu Pro
                420                 425                 430

Gln Ser Val Ser Gln Gly Tyr Phe Gly Ala Gly Ser Thr Met Met Val
                435                 440                 445

His Asn Leu Ile Thr Gly Val Arg Ala Pro Ala Ser Ser Val Asp Trp
    450                 455                 460

Thr Lys Ala Thr Val Asp Gly Val Gln Val Lys Thr Val Asp Ala Ser
465                 470                 475                 480

Ser Gly Ser Asn Arg Phe Ala Ala Leu Pro Ala Phe Gly Lys Pro Ala
                485                 490                 495

Val Trp Gly Pro Gln Gly Ala Gly Tyr Phe Tyr Gln Tyr Asn Ser Thr
                500                 505                 510

His Gln Glu Trp Ile Tyr Phe Leu Gln Asn Gly Ser Ser Val Val Trp
                515                 520                 525

Tyr Ala Tyr Thr Asn Met Leu Gly Gln Lys Ser Asp Thr Ser Ile Leu
    530                 535                 540
```

```
Phe Glu Val Arg Pro Ile Gln Ala Ser Asp Gln Pro Trp Phe Leu Ala
545                 550                 555                 560

His His Thr Gly Gly Asp Asp Cys Thr Thr Cys Leu Pro Leu Gly Leu
            565                 570                 575

Arg Thr Cys Cys Arg Gln Ala Pro Glu Asp Gln Ser Pro Glu Thr Arg
        580                 585                 590

Arg Leu Leu Asp Arg Leu Ser Arg Thr Phe Pro Ser Pro Pro
        595                 600                 605

<210> SEQ ID NO 7
<211> LENGTH: 1821
<212> TYPE: DNA
<213> ORGANISM: Hepatitis E virus

<400> SEQUENCE: 7
atgtcgctgt gtagattgtt gctcatgctt gcaatgtgct gcggggtgtc aaggggctcc      60
caaacgctcc cagccggagg caggcgtggc cagcgccgcc gtgacaattc agcccagtgg     120
agcactcaac aacgccccga gggagccgtc ggccccgccc ctctcacaga cgttgtcacc     180
gcggcaggta ctcgcacggt accagatgta gatcaagccg tgccgtgct ggtgcgccag      240 tataatctag tgaccagccc gttaggcctg ccaccttg gtagcaccaa tgccttgctt      300
tatgccgcac cggtgtcacc gttaatgccg cttcaggacg gcacgacgtc taatatcatg     360
agcacggagt ctagcaacta tgctcaatac cgtgtacagg gcctaactgt ccgctggcgc     420
ccagttgtgc caaatgcggt gggcggcttc tctataagca tggcctattg gccccagaca     480
acatccaccc ctacaagcat tgacatgaat tccatcacgt ccactgacgt ccgtgtggtg     540
cttcagccgg gctctgctgg tttgctgact ataccacatg agcgtttggc gtataagaac     600
aatggttggc ggtccgtcga aacggtatcc gtcccacagg aggatgccac gtccggcatg     660
ctcatggttt gtgtccacgg gacccctgg aatagttata ccaatagtgt ttacaccggg      720
ccgcttggta tggttgattt tgccataaag ttacagctaa ggaacttgtc gcccggtaat     780
acaaatgcca gggtcacccg tgtgaaggtg acggccccac ataccatcaa ggctgaccca     840
tctggtgcta ccataacaac agcagctgcg gccaggttta tggcggatgt gcgttggggc     900
ttgggcactg ctgaggatgg cgaaattggt cacggcatcc ttggtgttct gtttaacctg     960
gcggacacag ttttaggtgg cttgccctcg acactgctgc gggcggcgag tggtcagtac    1020
atgtacggcc ggcctgtggg gaacgcgaac ggcgagcctg aggtgaaact gtatatgtcg    1080
gttgaggatg ccgttaacga taaacctatt atggtccccc atgacatcga cctcgggacc    1140
agcactgtca cctgccagga ctatgggaat cagcatgtgg atgaccgccc atccccggcc    1200
ccggccccta agcgagcttt gggcacccta aggtcagggg atgtgttgcg tattactggc    1260
tccatgcagt atgtgactaa cgccgagttg ttaccgcaga gtgtgtcaca ggggtacttt    1320
ggggccggca gcaccatgat ggtgcataat ttgatcactg gtgtgcgcgc ccccgccagt    1380
tcagtcgact ggacgaaggc aacagtggat ggggtccagg tgaagactgt cgatgctagt    1440
tctgggagta taggtttgc agcgttacct gcatttggaa agccagctgt gtggggcgcc     1500
cagggcgctg gtatttcta ccagtataac agcacccacc aggagtggat ttatttctt      1560 cagaatggta gctccgtggt ttggtatgca tatactaata tgttgggcca gaagtcgat     1620 acatccattc ttttttgaggt ccggccaatc caagctagtg atcagccttg gttttggca    1680 caccacactg gcggcgatga ctgtaccacc tgtctgcctc tggggttaag aacatgttgc    1740
cgccaggcgc cagaagacca gtcacctgag acgcgccggc tcctagaccg gcttagtagg   1800
```

```
acattcccct caccaccta a                                                    1821

<210> SEQ ID NO 8
<211> LENGTH: 87
<212> TYPE: PRT
<213> ORGANISM: Hepatitis E virus

<400> SEQUENCE: 8

Met Cys Leu Ser Cys Gln Phe Trp Cys Leu Glu Cys Gln Glu Ser Gly
1               5                   10                  15
Val Gly Cys Arg Cys Val Asp Cys Cys Ser Cys Leu Gln Cys Ala Ala
            20                  25                  30
Gly Cys Gln Gly Ala Pro Lys Arg Ser Gln Pro Glu Ala Gly Val Ala
        35                  40                  45
Ser Ala Ala Val Thr Ile Gln Pro Ser Gly Ala Leu Asn Asn Ala Pro
    50                  55                  60
Arg Glu Pro Ser Ala Pro Pro Leu Ser Gln Thr Leu Ser Pro Arg Gln
65                  70                  75                  80
Val Leu Ala Arg Tyr Gln Met
                85

<210> SEQ ID NO 9
<211> LENGTH: 264
<212> TYPE: DNA
<213> ORGANISM: Hepatitis E virus

<400> SEQUENCE: 9
atgtgcctta gctgccagtt ctggtgtttg gagtgccagg aaagtggggt gggatgtcgc      60
tgtgtagatt gttgctcatg cttgcaatgt gctgcggggt gtcaaggggc tcccaaacgc     120
tcccagccgg aggcaggcgt ggccagcgcc gccgtgacaa ttcagcccag tggagcactc     180
aacaacgccc cgagggagcc gtcggccccg cccctctcac agacgttgtc accgcggcag     240
gtactcgcac ggtaccagat gtag                                            264

<210> SEQ ID NO 10
<211> LENGTH: 30
<212> TYPE: DNA
<213> ORGANISM: Hepatitis E virus

<400> SEQUENCE: 10
gggggatcca gtacatgtac ggccggcctg                                        30

<210> SEQ ID NO 11
<211> LENGTH: 29
<212> TYPE: DNA
<213> ORGANISM: Hepatitis E virus

<400> SEQUENCE: 11
ggggaattct tagggtggtg aggggaatg                                         29

<210> SEQ ID NO 12
<211> LENGTH: 529
<212> TYPE: DNA
<213> ORGANISM: Hepatitis E virus

<400> SEQUENCE: 12
ggggcccgac attcagcgga tgcaggacct tgagcaagcg tgtaaggatt ttgttgcacg      60
tgttgtaact cagggtaaag agatgttgac catccagctt gtggcgggtt attatggtgt     120
```

-continued

```
ggaagttggt atggttgagg tggtttgggg ggctttgaag gcctgcgccg cagcccgcga    180
gaccctagtg accaacaggt tgccggtact aaacttatct aaggaggact gaacaaataa    240
caatcattat gcagtctgcg cgtccatgtg ccttagctgc cagttctggt gtttggagtg    300
ccaggaaagt ggggtgggat gtcgctgtgt agattgttgc tcatgcttgc aatgtgctgc    360
ggggtgtcaa ggggctccca aacgctccca gccggaggca ggcgtggcca gcgccgccgt    420
gacaattcag cccagtggag cactcaacaa cgccccgagg gagccgtcgg ccccgcccct    480
ctcacagacg ttgtcaccgc ggcaggtact cgcacggtac cagatgtag                529
```

<210> SEQ ID NO 13
<211> LENGTH: 127
<212> TYPE: DNA
<213> ORGANISM: Hepatitis E virus

<400> SEQUENCE: 13

```
tgtcgtggtt ttggggtttt aggttgattt tctgtatctg ggcgtaattg cccctatgtt     60
taatttattg tgatttttat aactgttcat ttgattattt atgaaatcct cccatctcgg    120
gcatagt                                                              127
```

<210> SEQ ID NO 14
<211> LENGTH: 24
<212> TYPE: DNA
<213> ORGANISM: Hepatitis E virus

<400> SEQUENCE: 14

```
caatctcgac cagcacccca ccaa                                            24
```

<210> SEQ ID NO 15
<211> LENGTH: 22
<212> TYPE: DNA
<213> ORGANISM: Hepatitis E virus

<400> SEQUENCE: 15

```
acaggcccgg gtggatttat gg                                              22
```

<210> SEQ ID NO 16
<211> LENGTH: 26
<212> TYPE: DNA
<213> ORGANISM: Hepatitis E virus

<400> SEQUENCE: 16

```
gtgcaacagg gtcatccagc gtaaat                                          26
```

<210> SEQ ID NO 17
<211> LENGTH: 25
<212> TYPE: DNA
<213> ORGANISM: Hepatitis E virus

<400> SEQUENCE: 17

```
aaggctacca tccaatcggg catcc                                           25
```

<210> SEQ ID NO 18
<211> LENGTH: 25
<212> TYPE: DNA
<213> ORGANISM: Hepatitis E virus

<400> SEQUENCE: 18

```
atgtcgggcc cccagttctt gtcag                                           25
```

```
<210> SEQ ID NO 19
<211> LENGTH: 23
<212> TYPE: DNA
<213> ORGANISM: Hepatitis E virus

<400> SEQUENCE: 19
cccttgacac cccgcagcac att                                            23

<210> SEQ ID NO 20
<211> LENGTH: 26
<212> TYPE: DNA
<213> ORGANISM: Hepatitis E virus

<400> SEQUENCE: 20
tatagagaag ccgcccaccg catttg                                         26

<210> SEQ ID NO 21
<211> LENGTH: 25
<212> TYPE: DNA
<213> ORGANISM: Hepatitis E virus

<400> SEQUENCE: 21
gaccaatttc gccatcctca gcagt                                          25

<210> SEQ ID NO 22
<211> LENGTH: 25
<212> TYPE: DNA
<213> ORGANISM: Hepatitis E virus

<400> SEQUENCE: 22
accgacatat acagtttcac ctcag                                          25

<210> SEQ ID NO 23
<211> LENGTH: 23
<212> TYPE: DNA
<213> ORGANISM: Hepatitis E virus

<400> SEQUENCE: 23
caataggcca tgcttataga gaa                                            23

<210> SEQ ID NO 24
<211> LENGTH: 29
<212> TYPE: DNA
<213> ORGANISM: Hepatitis E virus

<400> SEQUENCE: 24
gcataccaaa ccacggagct accattctg                                      29

<210> SEQ ID NO 25
<211> LENGTH: 26
<212> TYPE: DNA
<213> ORGANISM: Hepatitis E virus

<400> SEQUENCE: 25
gccgcggtga caacgtctgt gagagg                                         26
```